(12) United States Patent
Mantlo et al.

(10) Patent No.: US 7,507,832 B2
(45) Date of Patent: Mar. 24, 2009

(54) TRIAZOLE PPAR MODULATORS

(75) Inventors: Nathan Bryan Mantlo, Brownsburg, IN (US); Antonio Navarro, Indianapolis, IN (US); Ashraf Saeed, Westfield, IN (US); Douglas Linn Gernert, Indianapolis, IN (US); Tianwei Ma, Carmel, IN (US); Lance Allen Pfeifer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 22 days.

(21) Appl. No.: 10/580,202

(22) PCT Filed: Dec. 21, 2004

(86) PCT No.: PCT/US2004/039775

§ 371 (c)(1),
(2), (4) Date: May 19, 2006

(87) PCT Pub. No.: WO2005/065683

PCT Pub. Date: Jul. 21, 2005

(65) Prior Publication Data

US 2007/0112045 A1 May 17, 2007

Related U.S. Application Data

(60) Provisional application No. 60/532,320, filed on Dec. 22, 2003.

(30) Foreign Application Priority Data

| Jul. 21, 2004 | (EP) | ................................. 04380158 |
| Jul. 21, 2004 | (EP) | ................................. 04380159 |

(51) Int. Cl.
*C07D 249/08* (2006.01)
(52) U.S. Cl. .................................. 548/267.8
(58) Field of Classification Search ............... 548/267.8
See application file for complete search history.

(56) References Cited

U.S. PATENT DOCUMENTS 3,637,672 A 1/1972 Seino et al.

FOREIGN PATENT DOCUMENTS

| EP | 0 453 846 A | 10/1991 |
| JP | 05 202038 A | 8/1993 |
| WO | WO 97/03967 A | 2/1997 |
| WO | WO 02/46174 A | 6/2002 |
| WO | WO 03/084916 A | 10/2003 |

OTHER PUBLICATIONS

Advanced Drug Delivery Reviews 48 (2001) 3-26.*
NINDS Acid Lipase Disease Information Page [online], [retrieved Apr. 9, 2008], Retrieved from the Internet, URL; http://www.ninds.nih.gov/disorders/acid_lipase/acid_lipase.htm.*
Metabolic disorder [online], [retrieved Apr. 9, 2008], Retrieved from the Internet, URL; http://en.wikipedia.org/wiki/Metabolic_disorder.*
Metabolic disorders [online], [retrieved Apr. 9, 2008], Retrieved from the Internet, URL; http://www.nlm.nih.gov/medlineplus/metabolicdisorders.html.*
NINDS Barth Syndrome Information Page [online], [retrieved Apr. 9, 2008], Retrieved from the Internet, URL; http://www.ninds.nih.gov/disorders/barth/barth.htm.*
Meanwell et al. Journal of Medicinal Chemistry, vol. 35, No. 19, 1992, pp. 3498-3512.
Database Beilstein, Nov. 28, 1988, XP002322768 Database accesion No. BRN: 677345 CAS Registry No. 52997-97-4 Chemical Name: 2-(5-phenyl-2H-'1,2,4!triazol-3-ylmethyl)-benzoic acid abstract, Kimoto et al: Yakugaku Zasshi, vol. 94, 1974, pp. 55-60, & other compounds disclosed therein.
Database Beilstein, Nov. 28, 1988, XP002322769 Database accesion No. BRN: 1008075 CAS Registry No. 57712-41-1 Chemical Name: 2-(5-phenyl-'1,3,4!oxadiazol-2-ylmethyl)-benzoic acid abstract, & Takahashi et al, Bull. Chem. Soc. JPN., vol. 48, 1975, pp. 2915-2917, and other compounds disclosed therein.
Database Beilstein, Nov. 28, 1988, XP002322863 Database accesion No. BRN: 1013052 CAS Registry No. 71860-01-0 Chemical Name: 2-(5-phenyl-'1,3,4!thiadiazol-2-ylamoni)-benzoic acid abstract & Russo et al: Farmaco Ed. Sci., vol. 34, 1979, pp. 688-697, & other compounds disclosed therein.

\* cited by examiner

*Primary Examiner*—Rei-Tsang Shiao
*Assistant Examiner*—Shawquia Young
(74) *Attorney, Agent, or Firm*—MaCharri Vorndran-Jones

(57) ABSTRACT

The present invention is directed to compounds represented by the following structural formula, Formula (I): wherein: (a) X is selected from the group consisting of a single bond, O, S, $S(O)_2$ and N; (b) U is an aliphatic linker; (c) Y is selected from the group consisting of O, C, S, NH and a single bond; (d) W is N, O or S; (e) E is C(R3)(R4)A or A and wherein; (f) A is selected from the group consisting of carboxyl, tetrazole, $C_1$-$C_6$ alkylnitrile, carboxamide, sulfonamide and acylsulfonamide. The other substituents are defined in the claims; the compounds are modulators of peroxisome proleferator activated receptors (PPARs) and are useful for the treatment of diabetes and other metabolic disorders.

17 Claims, No Drawings

TRIAZOLE PPAR MODULATORS

This application is a United States national phase entry, pursuant to 35 U.S.C. 371, of PCT/US2004/039775, filed on Dec. 21, 2004, which claims the benefit of U.S. provisional patent application Ser. No. 60/532,320, filed Dec. 22, 2003, and hereby incorporated by reference in their entirety.

Information disclosed and/or claimed in this patent application has been generated pursuant to a joint research agreement among Eli Lily and Company and Ligand Pharmaceuticals, Inc.

BACKGROUND OF THE INVENTION

Peroxisome Proliferator Activated Receptors (PPARs) are members of the nuclear hormone receptor superfamily, a large and diverse group of proteins that mediate ligand-dependent transcriptional activation and repression. Three subtypes of PPARs have been isolated: PPARα, PPARγ and PPARδ.

The expression profile of each isoform differs significantly from the others, whereby PPARα is expressed primarily, but not exclusively in liver; PPARγ is expressed primarily in adipose tissue; and PPARδ is expressed ubiquitously. Studies of the individual PPAR isoforms and ligands have revealed their regulation of processes involved in insulin resistance and diabetes, as well as lipid disorders, such as hyperlipidemia and dyslipidermia. PPARγ agonists, such as pioglitazone, can be useful in the treatment of non-insulin dependent diabetes mellitus. Such PPARγ agonists are associated with insulin sensitization.

PPARα agonists, such as fenofibrate, can be useful in the treatment of hyperlipidemia. Although clinical evidence is not available to reveal the utility of PPARδ agonists n humans, several preclinical studies suggest that PPARδ agonists can be useful in the treatment of diabetes and lipid disorders.

The prevalence of the conditions that comprise Metabolic Syndrome (obesity, insulin resistance, hyperlipidemia, hypertension and atherosclerosis) continues to increase. New pharmaceutical agents are needed to address the unmet clinical needs of patients.

PPARδ agonists have been suggested as a potential treatment for use in regulating many of the parameters associated with Metabolic Syndrome and Atherosclerosis. For example, in obese, non-diabetic rhesus monkeys, a PPARδ agonist reduced circulating triglycerides and LDL, decreased basal insulin levels and increased HDL (Oliver, W. R. et al. Proc Natl Acad Sci 98:5306-5311; 2001). The insulin sensitization observed with the use of a PPARδ agonist is thought to be in part due to decreased myocellular lipids (Dressel, U. et al. Mol Endocrinol 17:2477-2493; 2003).

Further, atherosclerosis is considered to be a disease consequence of dyslipidemia and may be associated with inflammatory disease. C-reactive protein (CRP) production is part of the acute-phase response to most forms of inflammation, infection and tissue damage. It is measured diagnostically as a marker of low-grade inflammation. Plasma CRP levels of greater than 3 mg/L have been considered predictive of high risk for coronary artery disease (J. Clin. Invest 111: 1085-1812, 2003).

PPARδ agonists are believed to mediate anti-inflammatory effects. Indeed, treatment of LPS-stimulated macrophages with a PPARδ agonist has been observed to reduce the expression of iNOS, IL-12, and IL-6 (Welch, J. S. et al. Proc Natl Acad Sci 100:6712-67172003).

It may be especially desirable when the active pharmaceutical agent selectively modulates a PPAR receptor subtype to provide an especially desirable pharmacological profile. In some instances, it can be desirable when the active pharmacological agent selectively modulates more than one PPAR receptor subtype to provide a desired pharmacological profile.

SUMMARY OF THE INVENTION

The present invention is directed to compounds represented by the following structural Formula I:

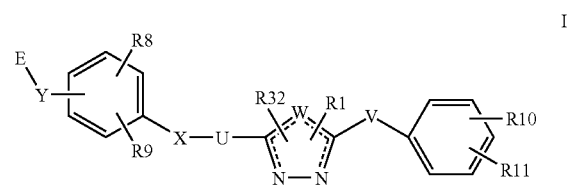

and stereoisomers, pharmaceutically acceptable salts, solvates and hydrates thereof, wherein:
(a) R1 is selected from the group consisting of hydrogen, $C_1$-$C_8$ alkyl, $C_1$-$C_8$ alkenyl, $C_1$-$C_8$ heteroalkyl, aryl-$C_{0-4}$-alkyl, aryl-$C_{1-4}$-heteroalkyl, heteroaryl-$C_{0-4}$-alkyl, and $C_3$-$C_6$ cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, $C_3$-$C_6$ cycloalkylaryl-$C_{0-2}$-alkyl are each optionally substituted with from one to three substituents independently selected from R1';
(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C (O)R19, NR20SO$_2$R21, SR22, S(O)R23, S(O)$_2$R24, and S(O)$_2$N(R25)$_2$; R12, R13, R14, R15, R16, R17, R18, R19, R20, R2, R22, R23, R24 and R25 are each independently selected from the group consisting of hydrogen, $C_1$-$C_6$ alkyl and aryl;
(c) V is selected from the group consisting of $C_0$-$C_8$ alkyl and $C_{1-4}$-heteroalkyl;
(d) X is selected from the group consisting of a single bond, O, S, S(O)$_2$ and N;
(e) U is an aliphatic linker wherein one carbon atom of the aliphatic linker is optionally replaced with O, NH or S, and wherein such aliphatic linker is optionally substituted with from one to four substituents each independently selected from R30;
(f) W is N, O or S;
(g) Y is selected from the group consisting of C, O, S, NH, and a single bond;
(h) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
  (ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with from one to three substituents each independently selected from R26;

(i) R8 is selected from the group consisting of hydrogen, $C_1$-$C_4$ alkyl, $C_1$-$C_4$ alkylenyl, and halo;

(j) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(k) R10, R11 are each independently selected from the group consisting of hydrogen, hydroxy, cyano, nitro, halo, oxo, $C_1$-$C_6$ alkyl, $C_1$-$C_6$ alkylenyl, $C_1$-$C_6$ alkyl-COOR12", $C_0$-$C_6$ alkoxy, $C_1$-$C_6$haloalkyl, $C_1$-$C_6$ haloalkyloxy, $C_3$-$C_7$ cycloalkyl, aryl-$C_{0\text{-}4}$-alkyl, aryl-$C_{1\text{-}4}$-heteroalkyl, heteroaryl-$C_{0\text{-}4}$-alkyl, C3-C6 cycloalkylaryl-$C_{0\text{-}2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0\text{-}4}$-alkyl, aryl-$C_{1\text{-}4}$-heteroalkyl, heteroaryl-$C_{0\text{-}4}$-alkyl, and C3-C6 cycloalkylaryl-$C_{0\text{-}2}$-alkyl are each optionally substituted with from one to three independently selected from R28; and wherein R10 and R11 optionally combine to form a 5 to 6 membered fused bicyclic ring with the phenyl to which they are bound;

(l) R12', R12", R13', R14', R15', R16', R17', R18', R19', R20', R21', R22', R23', R24', and R25' are each independently selected from the group consisting of hydrogen, $C_1$-$C_6$ alkyl and aryl;

(m) R30 is selected from the group consisting of $C_1$-$C_6$ alkyl, aryl-$C_{0\text{-}4}$-alkyl, aryl-$C_{1\text{-}4}$-heteroalkyl, heteroaryl-$C_{0\text{-}4}$-alkyl, and C3-C6 cycloalkylaryl-$C_{0\text{-}2}$-alkyl, and wherein $C_1$-$C_6$ alkyl, aryl-$C_{0\text{-}4}$-alkyl, aryl-$C_{1\text{-}4}$-heteroalkyl, heteroaryl-$C_{0\text{-}4}$-alkyl, and C3-C6 cycloalkylaryl-$C_{0\text{-}2}$-alkyl are each optionally substituted with from one to three substituents each independently selected from R31;

(n) R32 is selected from the group consisting of a hydrogen, halo, $C_1$-$C_6$ alkyl, $C_1$-$C_6$ haloalkyl, and $C_1$-$C_6$ alkyloxo; and (o) ---- is optionally a bond to form a double bond at the indicated position.

A further embodiment of the present invention is a compound of the Formula Ia:

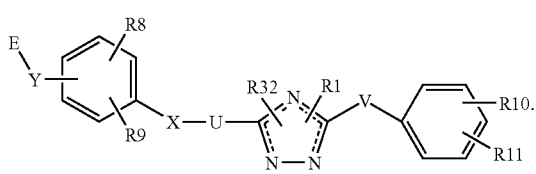

Ia

A further embodiment of the present invention is a compound of the Formula Ib:

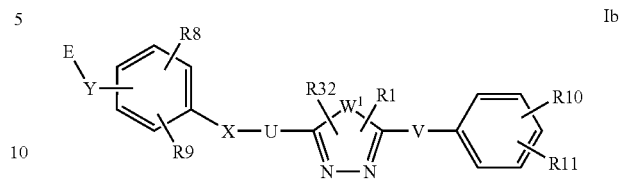

Ib wherein $W^1$ is O or S.

A further embodiment of the present invention is a compound of the Formula Ic:

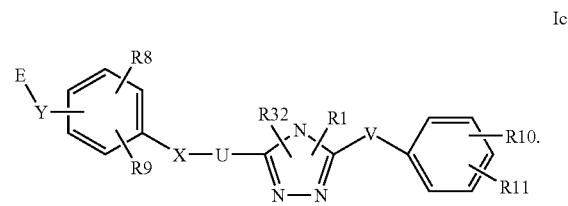

Ic

A further embodiment of the present invention is a compound of the Formula II:

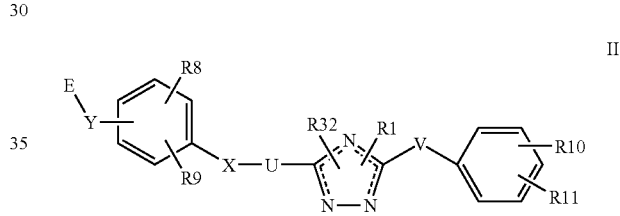

II and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, aryl-$C_{0\text{-}4}$-alkyl, aryl-$C_{1\text{-}4}$-heteroalkyl, heteroaryl-$C_{0\text{-}4}$-alkyl, and C3-C6 cycloalkylaryl-$C_{0\text{-}2}$-alkyl, and, wherein $C_1$-$C_8$ alkyl, $C_1$-$C_8$ alkenyl, aryl-$C_{0\text{-}4}$-alkyl, aryl-$C_{1\text{-}4}$-heteroalkyl, heteroaryl-$C_{0\text{-}4}$-alkyl, C3-C6 cycloalkylaryl-$C_{0\text{-}2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0\text{-}4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) V is selected from the group consisting of $C_0$-$C_8$ alkyl and $C_{1\text{-}4}$-heteroalkyl;

(d) X is selected from the group consisting of a single bond, O, S, S(O)$_2$ and N;

(e) U is an aliphatic linker wherein one carbon atom of the aliphatic linker is optionally replaced with O, NH or S, and wherein such aliphatic linker is substituted with from one to four substituents each independently selected from R30;

(f) Y is selected from the group consisting of C, O, S, NH and a single bond;

(g) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
  (II) each $R^7$ is independently selected from the group consisting of hydrogen, $C_1$-$C_6$haloalkyl, aryl $C_0$-$C_4$ alkyl and $C_1$-$C_6$ alkyl;
  (iii) R3 is selected from the group consisting of hydrogen, $C_1$-$C_5$ alkyl, and $C_1$-$C_5$ alkoxy; and
  (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with from one to three substituents each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkylenyl, $C_1$-$C_6$ alkyl-COOR12", $C_0$-$C_6$ alkoxy, $C_1$-$C_6$haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28; and wherein R10 and R11 optionally combine to form a 5 to 6 membered fused bicyclic ring with the phenyl to which they are bound;

(k) R12', R12", R13', R14', R15', R16', R17', R18', R19', R20', R21', R22', R23', R24', and R25' are each independently selected from the group consisting of hydrogen, $C_1$-$C_6$ alkyl and aryl;

(l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(m) R32 is selected from the group consisting of a bond, hydrogen, halo, $C_1$-$C_6$ alkyl, $C_1$-$C_6$haloalkyl, and $C_1$-$C_6$ alkyloxo; and (n) ---- is optionally a bond to form a double bond at the indicated position.

Another embodiment of the present invention is a compound of the Formula III:

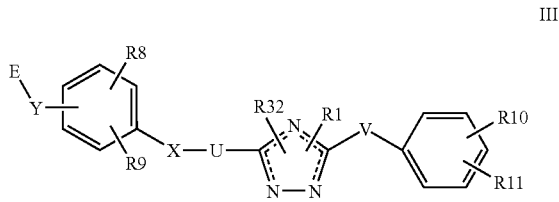

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, $C_1$-$C_8$ heteroalkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-akyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) V is selected from the group consisting of $C_0$-$C_8$ alkyl and $C_{1-4}$-heteroalkyl;

(d) X is selected from the group consisting of a single bond, O, S, S(O)$_2$ and N;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of O, S, NH, C, and a single bond;

(g) E is C(R3)(R4)A; wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
  (II) each $R^7$ is independently selected from the group consisting of hydrogen, $C_1$-$C_6$haloalkyl, aryl $C_0$-$C_4$ alkyl and $C_1$-$C_6$ alkyl;
  (iii) R3 is selected from the group consisting of $C_1$-$C_5$ alkyl, and $C_1$-$C_5$ alkoxy; and
  (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with from one to three substituents each independently selected from R26;

with the proviso that when Y is O then R4 is selected from the group consisting of $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkylenyl, $C_1$-$C_6$ alkyl-COOR12'', $C_0$-$C_6$ alkoxy, $C_1$-$C_6$haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28; and wherein R10 and R11 optionally combine to form a 5 to 6 membered fused bicyclic ring with the phenyl to which they are bound;

(k) R12', R12'', R13', R14', R15', R16', R17', R18', R19', R20', R21', R22', R23', R24', and R25' are each independently selected from the group consisting of hydrogen, $C_1$-$C_6$ alkyl and aryl;

(l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(m) R32 is selected from the group consisting of a bond, hydrogen, halo, $C_1$-$C_6$ alkyl, $C_1$-$C_6$haloalkyl, and $C_1$-$C_6$ alkyloxo; and (n) ---- is optionally a bond to form a double bond at the indicated position.

In one embodiment, the present invention also relates to pharmaceutical compositions comprising at least one compound of the present invention, or a pharmaceutically acceptable salt, solvate, hydrate, or stereioisomer thereof, and a pharmaceutically acceptable carrier.

In another embodiment, the present invention relates to a method of selectively modulating a PPAR delta receptor comprising contacting the receptor with at least one compound represented by Structural Formula I, or a pharmaceutically acceptable salt, solvate, hydrate, or stereioisomer thereof.

In another embodiment, the present invention relates to a method of modulating one or more of the PPAR alpha, beta, gamma, and/or delta receptors.

In a further embodiment, the present invention relates to a method of making a compound represented by Structural Formula I.

The compounds of the present invention are believed to be effective in treating and/or preventing Metabolic Disorder, Type II diabetes, hyperglycemia, hyperlipidemia, obesity, coagaulopathy, hypertension, atherosclerosis, and other disorders related to Metabolic Disorder and cardiovascular diseases. Further, compounds of this invention can be useful for lowering fibrinogen, increasing HDL levels, treating renal disease, controlling desirable weight, treating demyelinating diseases, treating certain viral infections, and treating liver disease. In addition, the compounds can be associated with fewer clinical side effects than compounds currently used to treat such conditions.

DETAILED DESCRIPTION OF THE INVENTION

The terms used to describe the instant invention have the following meanings.

As used herein, the term "aliphatic linker" or "aliphatic group" is a non-aromatic, consisting solely of carbon and hydrogen and may optionally contain one or more units of unsaturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl"). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like. Such aliphatic linker is optionally substituted with from one to four substituents each independently selected from R30. It can be preferred that aliphatic linker is substituted with from zero to two substituents each independently selected from R30. Further, it may be preferred that one carbon of the alphatic linker is replaced with an O, NH, or S. Finally, it may be preferred that the aliphatic linker is purely alkyl, with no carbon replaced with an O, NH, or S.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" or "alkylenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a means a straight or branched hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$).

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). "Aryl" as defined above may be optionally substituted with a designated number of substituents as set forth in the embodiment recited above.

The term "arylalkyl" refers to an aryl alkyl group which is linked to the parent molecule through the alkyl group, which may be further optionally substituted with a designated number of substituents as set forth in the embodiment recited above. When arylalkyl is arylCoalkyl, then the aryl group is bonded directly to the parent molecule. Likewise, arylheteroalkyl means an aryl group linked to the parent molecule through the heteroalkyl group.

The term "acyl" refers to alkylcarbonyl, arylcarbonyl, and heteroarylcarbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated number of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

When "----" is optionally a bond that forms a double bond in the five-membered heterocycle, the possible heterocycles include:

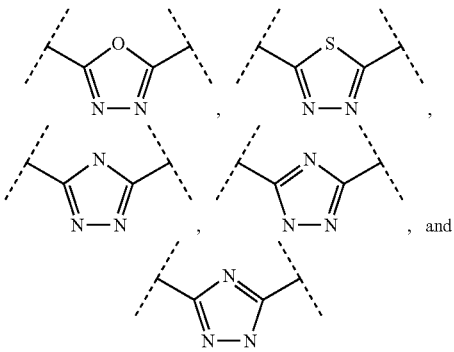

As used herein, the phrase "selectively modulate" means a compound whose $EC_{50}$ for the stated PPAR receptor is at least ten fold lower than its $EC_{50}$ for the other PPAR receptor subtypes.

PPARδ has been proposed to associate with and dissociate from selective co-repressors (BCL-6) that control basal and stimulated anti-inflammatory activities (Lee, C-H. et al. Science 302:453-4572003). PPARδ agonists are thought to be useful to attenuate other inflammatory conditions such as inflammation of the joints and connective tissue as occurs in rheumatoid arthritis, related autoimmune diseases, osteoarritis, as well as myriad other inflammatory diseases, Crohne's disease, and psoriasis.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I which are considered to be acceptable for clinical and/or veterinary use. Typical pharmaceutically-acceptable salts include those salts prepared by reaction of the compounds of the present invention with a mineral or organic acid or an organic or inorganic base. Such salts are known as acid addition salts and base addition salts, respectively. It will be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to the skilled artisan.

The term, "active ingredient" means the compounds generically described by Structural Formula I as well as the sterioisomers, salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well-known and readily available ingredients.

"Preventing" refers to reducing the likelihood that the recipient will incur or develop any of the pathological conditions described herein. The term "preventing" is particularly applicable to a patient that is susceptible to the particular pathological condition.

"Treating" refers to mediating a disease or condition and preventing, or mitigating, its further progression or ameliorate the symptoms associated with the disease or condition.

"Pharmaceutically-effective amount" means that amount of active ingredient that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition. Generally, the effective amount of a Compound of Formula I will be between 0.02 through 5000 mg per day. Preferably the effective amount is between 1 through 1,500 mg per day. Preferably the dosage is from 1 through 1,000 mg per day. A most preferable the dose can be from 1 through 100 mg per day.

The desired dose may be presented in a single dose or as divided doses administered at appropriate intervals.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

Further, the compound and compositions of the present invention may reduce the incidence of undesired cardiac events in patients. The physician of ordinary skill will know how to identify humans who will benefit from administration of the compounds and compositions of the present invention.

The compounds and compositions of the present invention can also be useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective amount of active ingredient, as defined herein, to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Metabolic Disorder, diabetes, treating obesity, lowering triglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

When used herein Metabolic Syndrome includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis. In addition, the methods and treatments mentioned herein include the above and encompass the treatment and/or prophylaxis of any one of or any combination of the following inflammatory and autoimmune diseases: adult respiratory distress syndrome, rheumatoid arthritis, demyelinating disease, Chrohne's disease, asthma, systemic lupus erythematosus, psoriasis, and bursitis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I, a stereoisomer, salt, solvate and/or hydrate thereof ("Active Ingredient") and one or more additional active agents, as well as administration of a compound of Active Ingredient and each active agent in its own separate pharmaceutical dosage formulation. For example, an Active Ingredient and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein an Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agent.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredients of the present invention, have valuable pharmacological properties and can be used in pharmaceutical compositions containing a therapeutically effective amount of Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical formulations typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient of the present invention, calculated to produce the desired therapeutic effect, in association with one or more pharmaceutically-acceptable excipients. The quantity of active ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

The following pharmaceutical formulations 1 and 2 are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some preferred characteristics of compounds of formula I are:
(a) R3 is methyl;
(b) R4 is hydrogen;
(c) R3 and R4 are each hydrogen;
(d) R3 and R4 are each methyl;
(e) A is carboxyl;
(f) X is —O—;
(g) X is —S—;
(h) X is a single bond;
(i) U is CH(R30);
(j) U is CH$_2$CH(R30);
(k) U is CH2CH(R30)CH2;
(l) U is CH$_2$N(R30)CH$_2$;
(m) U is CH$_2$OCH$_2$;
(n) U is CH$_2$CH$_2$CH$_2$;
(o) U is CH$_2$;
(p) U is CH$_2$NHCH$_2$;
(q) U is CH$_2$N(CH$_3$)CH$_2$;
(r) U is CH$_2$N(CH(CH$_3$)$_2$)CH$_2$;
(s) U is CH$_2$N(CH$_2$CH$_2$CH$_3$)CH$_2$;
(t) U is CH$_2$N(CH$_2$CH$_3$)CH$_2$;
(u) W is N;
(v) W is O;
(w) W is S;
(x) R30 is CH$_3$;
(y) R30 is phenyl;
(z) R30 is CH$_2$CH$_2$CH$_2$CH$_3$;
(aa) R30 is CH$_2$CH$_2$CF$_3$;
(bb) R30 is CH$_2$CH=CH$_2$;
(cc) R30 is CH(CH$_3$)$_2$;
(dd) R30 is CH$_2$CH$_2$CH$_3$;
(ee) R30 is CH$_2$CH$_3$;
(ff) R9 is methyl;
(gg) R9 is hydrogen;
(hh) R9 is C$_1$-C$_3$ alkyl;
(ii) R8 is methyl;
(jj) R8 and R9 are each hydrogen;
(kk) R10 is CF$_3$;
(ll) R10 is haloalkyl;
(mm) R10 is haloalkyloxy;
(nn) R11 is hydrogen
(oo) R10 and R11 are each hydrogen;
(pp) R11 is haloalkyl;
(qq) R10 and R11 combine to form a fused bicyclic;
(rr) R10 and R11 combine to form a naphtyl substituent with the phenyl to which they are attached;
(ss) R1 is optionally substituted C$_2$-C$_3$ arylalkyl;
(tt) R1 is substituted C$_2$ arylalkyl;
(uu) R1 is C$_1$-C$_8$heteroalkyl;
(vv) R1 is heteroalkyl wherein one of the carbon atoms is replaced with an oxygen;

(ww) R1 is heteroalkyl wherein two of the carbon atoms is replaced with an oxygen;
(xx) R1 is substituted with one R1';
(yy) R1 is C$_1$-C$_3$ alkenyl;
(zz) R1 is C$_1$-C$_4$ alkyloxo;
(aaa) R1 is C$_1$-C$_4$ alkyl;
(bbb) R32 is hydrogen;
(ccc) ---- in the five membered ring each form a double bond at the designated position in Formula I;
(ddd) V is a bond;
(eee) V is C$_1$-C$_3$ alkyl;
(fff) V is CH$_2$;
(ggg) V is CH$_2$CH$_2$;
(hhh) V is CH$_2$CH$_2$CH$_2$;
(iii) Y is O;
(jjj) Y is S;
(kkk) Y is C;
(lll) Y is C, NH, or a bond;
(mmm) E is C(R3)(R4)A;
(nnn) R3 is hydrogen;
(ooo) R3 is C$_1$-C$_2$ alkyl;
(ppp) R4 is C$_1$-C$_2$ alkyl;
(qqq) R3 and R4 are each hydrogen;
(rrr) R3 and R4 are each methyl;
(sss) A is COOH;
(ttt) Aliphatic linker is saturated;
(uuu) Aliphatic linker is substituted with C$_1$-C$_3$ alkyl;
(vvv) Aliphatic linker is substituted with from one to three substituents each independently selected from R30;
(www) Aliphatic linker is substituted with from one to two substituents each independently selected from R30;
(xxx) Aliphatic linker is C$_1$-C$_3$ alkyl;
(yyy) Aliphatic linker is C$_1$-C$_2$ alkyl;
(zzz) Aliphatic linker is C$_1$-C$_3$ alkyl and one carbon is replaced with an —O—;
(aaaa) A compound of Formula IV:

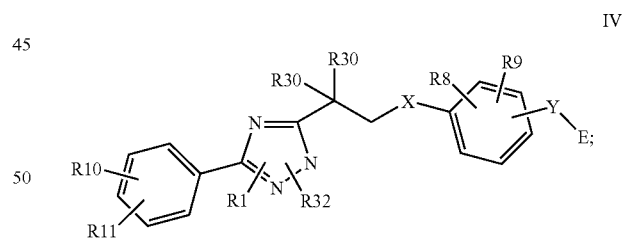

(bbbb) A compound of Structural Formula V:

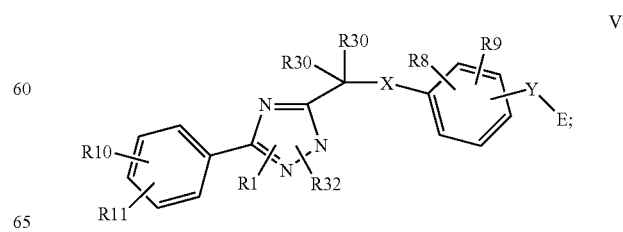

(cccc) A compound of Structural Formula VI:

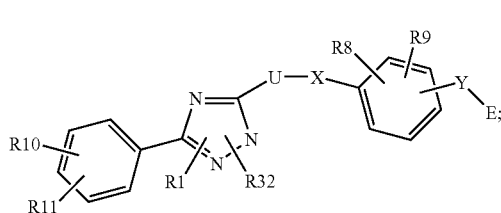

(dddd) A compound of Structural Formula VII:

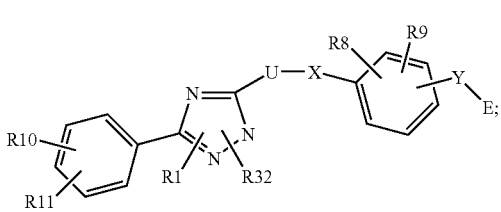

(eeee) A compound of Structural Formula VIII:

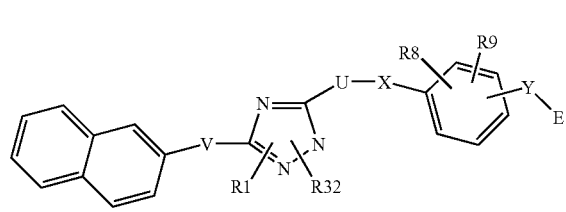

(ffff) A compound of Structural Formula VIIIa:

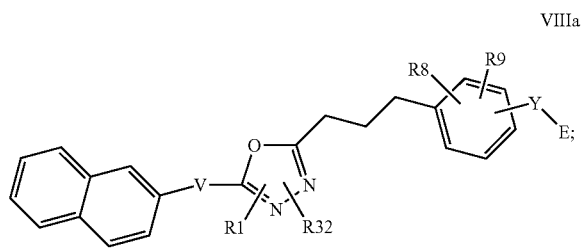

(gggg) A compound of Structural Formula IX:

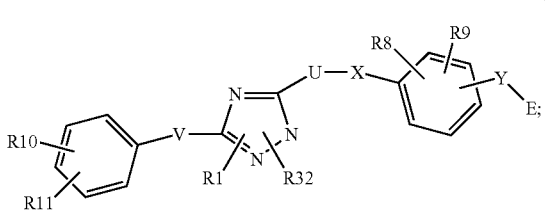

(hhhh) A compound of Structural Formula X:

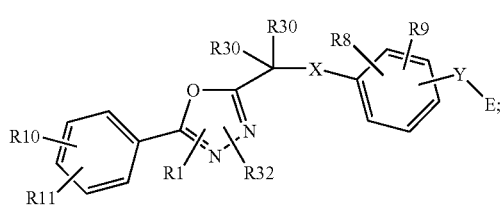

(iiii) A compound of Structural Formula XI:

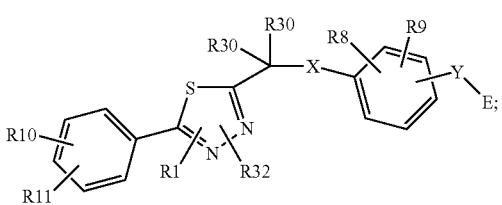

(jjjj) A compound of Structural Formula XII:

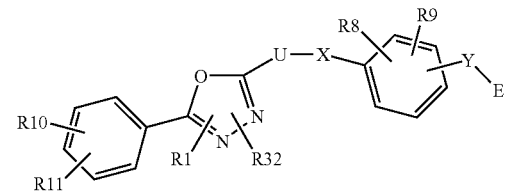

(kkkk) A compound of Structural Formula XIII:

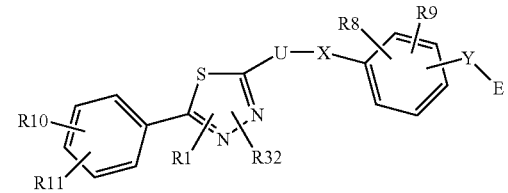

(llll) Aryl is a phenyl group;
(mmmm) Aryl is a naphthyl group;
(nnnn) A compound of Formula I that selectively modulates a delta receptor;
(oooo) An Active Ingredient, as described herein, that is a PPAR coagaonist that modulates a gamma receptor and a delta receptor;
(pppp) An Active Ingredient, as described herein, for use in the treatment of cardiovascular disease;
(qqqq) An Active Ingredient, as described herein, for use in the treatment of Metabolic Disorder;
(rrrr) An Active Ingredient for use in the control of obesity;
(ssss) An Active Ingredient for use in treating diabetes;
(tttt) An Active Ingredient that is a PPAR receptor agonist;
(uuuu) A compound of Formula I selected from the group consisting of 2-Methyl-2-{4-[3-(5-naphthalen-2-ylmethyl-2H-[1,2,4]triazol-3-yl)-phenoxy}proprionic acid.

Scheme 1
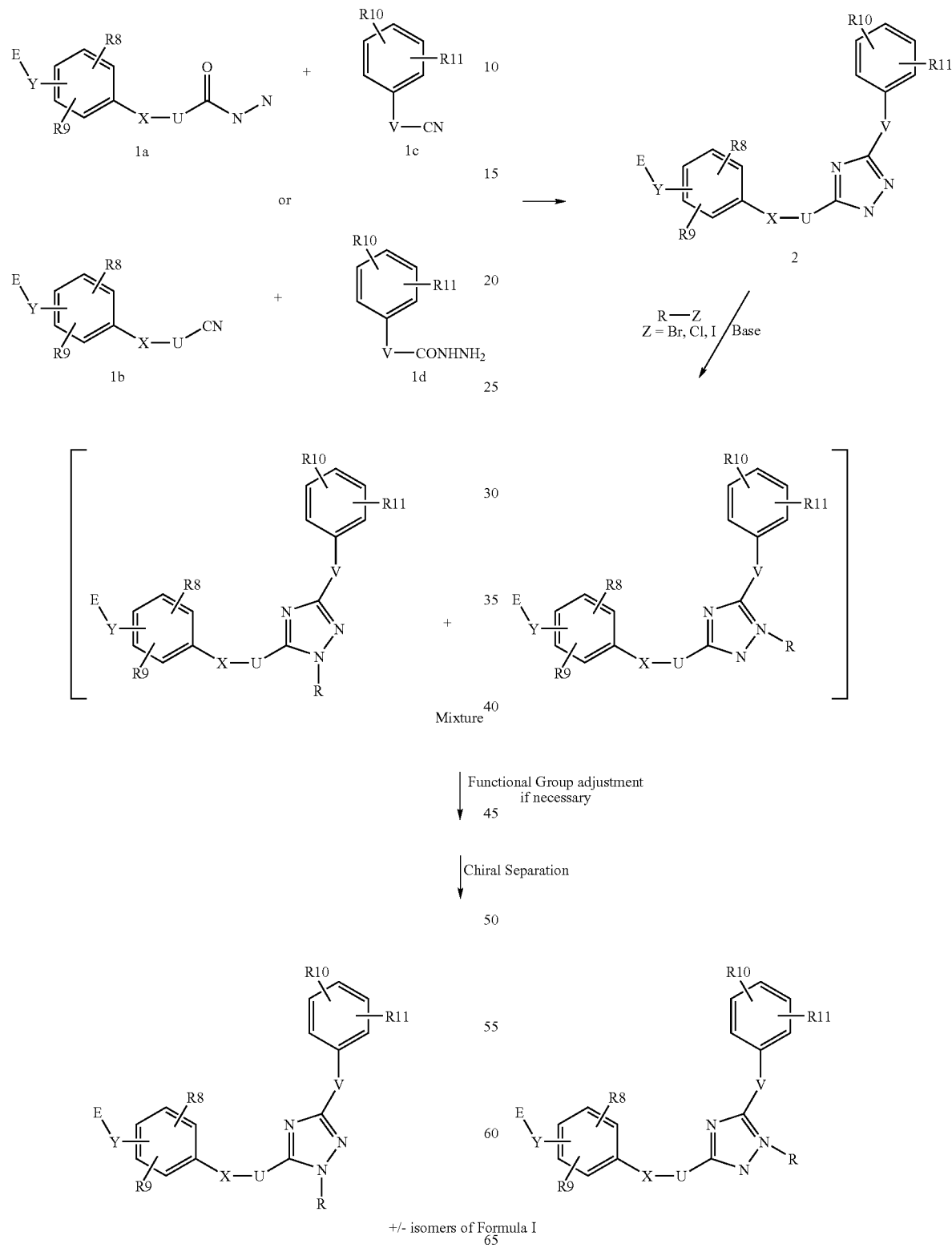

Compounds of Formula I are prepared by the reaction of either a carbonyl hydrazone 1a in the presence of a carbonitrile 1b or of a carbonyl hydrazone 1d in the presence of a carbonitrile 1c to give intermediates 2. The reaction to form the triazole core 2 occurs in the presence of a strong base, e.g., sodium, lithium, or potassium alkoxides or sodium, lithium or potassium hydroxides in a polar protic solvent such as lower molecular weight alkanols, e.g., methanol, ethanol, or n- or i-propanol at reaction temperatures from room temperature to the reflux temperature of the mixture. Compound 2 is alkylated with a primary or secondary alkyl halide R-Z, where R includes the definition of both R32 and R1 in the presence of a base, e.g., sodium, lithium, or potassium bicarbonate or carbonate in a polar aprotic solvent, e.g., acetonitrile, acetone, or DMF at from room temperature to the reflux temperature of the mixture. Catalytic KI may be added to facilitate the overall alkylation by in situ replacement of R-Z, if Z is Cl or Br, to the more reactive R-I alkyation reagent. The alkylation with R give a mixture of regio and therefore optical isomers of Formula I.

Since racemic mixtures of Formula I are separated and isolated by chiral chromatography to pure isomers, at times, the racemic mixtures of Formula I are required to have functional group adjustments, perhaps, lending the mixtures to optimum separation in the chiral chromatography procedure. Functional group adjustments anticipated here and appreciated by one skilled in manipulations of organic reactions include manipulations of carboxylic acid derivatives, if applicable, to either esters of low molecular weight such as methyl or ethyl esters or to esters with steric hindrance such as t-butyl esters. Alternately as appreciated by one skilled in the execution of synthetic methodologies, ester functionalities, if applicable, my be adjusted to the free carboxylic acids by saponification of lower molecular weight esters with sodium, lithium or potassium hydroxides in a polar protic solvents, such as, methanol or ethanol, or strong acid hydrolysis of hindered esters, e.g., t-butyl esters with TFA in a weakly polar aprotic solvent such as methylene chloride or dichloroethane.

Other functional group manipulations include the conversion of ketones or aldehydes, if applicable, to ketals and acetals, with lower molecular weight alkane-diols and strong acid, e.g., tosic acid and sulfuric acid. Alternately, acetals and ketals, if present, may be converted to the corresponding carbonyl compound with strong acid and hydrated lower alkanols or with BBr3 in dichloromethane or dichloroethane.

The starting materials for the above scheme may often be commercially available, particularly, for carbonitrile compounds 1c and 1b. Other carbonitriles of formula 1c and 1b may be prepared, as is common to one skilled in the art of organic manipulations, from 1) commercially available or known carboxylic acids by conversion to primary amides followed by dehydration with a Vilsmeier reagent or 2) commercially available or known carboxaldehydes by conversion to oximes followed by dehydration with a Vilsmeier reagent.

Hydrazones of the formula 1a and 1d are prepared from the corresponding carboxylic acids or acid halides and hydrazine in dichloromethane or dichloroethane in the presence of base such as, pyridine, triethylamine, or sodium, lithium, or potassium bicarbonate or carbonate. A particularly useful reference for the preparation of 1a or 1d is Xu, Yanping, et. al. J. Med. Chem. 46(24)(2003) p. 5121-5124, where analogous reactions may be applied to the synthesis of 1a or 1d using commercially available or known carboxylic acids.

Preparation 1 (Compound 1)

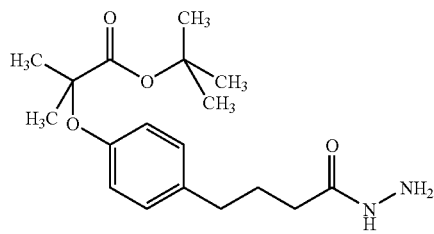

EXAMPLE 2A

Compound 2A

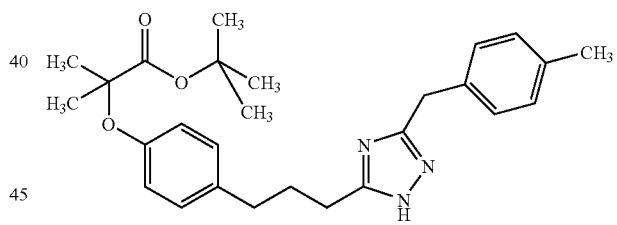

Take up the compound or preparation 1 [Xu, et. al. Loc. Sit. (2003)] (1.34 gm, 4 mmol) in methanol (30 mL). To this solution, add 4-methylbenzylnitrile (1.04 gm, 8 mmole), followed by sodium methoxide (75 mg). Heat the reaction at reflux (~80° C.) with stirring for 24 h. Dilute the mixture with ethyl acetate (50 mL). Wash the ethyl acetate with water (3×60 mL), dried (Na$_2$SO$_4$), and concentrate on a rotovap to give an oily residue. Purify the residue on a silica column to give Example 2A as an oil (670 mg). m/z: M+1450.

EXAMPLES 2B-2D

Synthesize Examples 2B to 2D shown in the following Table according to the procedure for example 2A, from preparation 1 using appropriate nitrile shown in Table below.

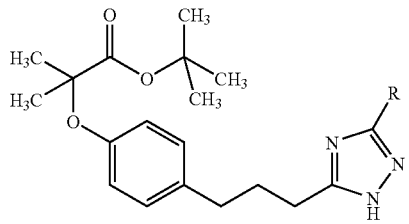

| Example | R | Nitrile Used | (m/z) M + 1 |
|---|---|---|---|
| 2B | Phenethyl | 2-Phenylpropionitrile | 450 |
| 2C | Naphthylmethyl | 2-Naphthylacetonitrile | 486 |
| 2D | 3-(4-Chlorophenyl)-3-ethoxypropyl | 4-(4-Chlorophenyl)-4-ethoxybutyronitrile | 542 |

EXAMPLE 3A

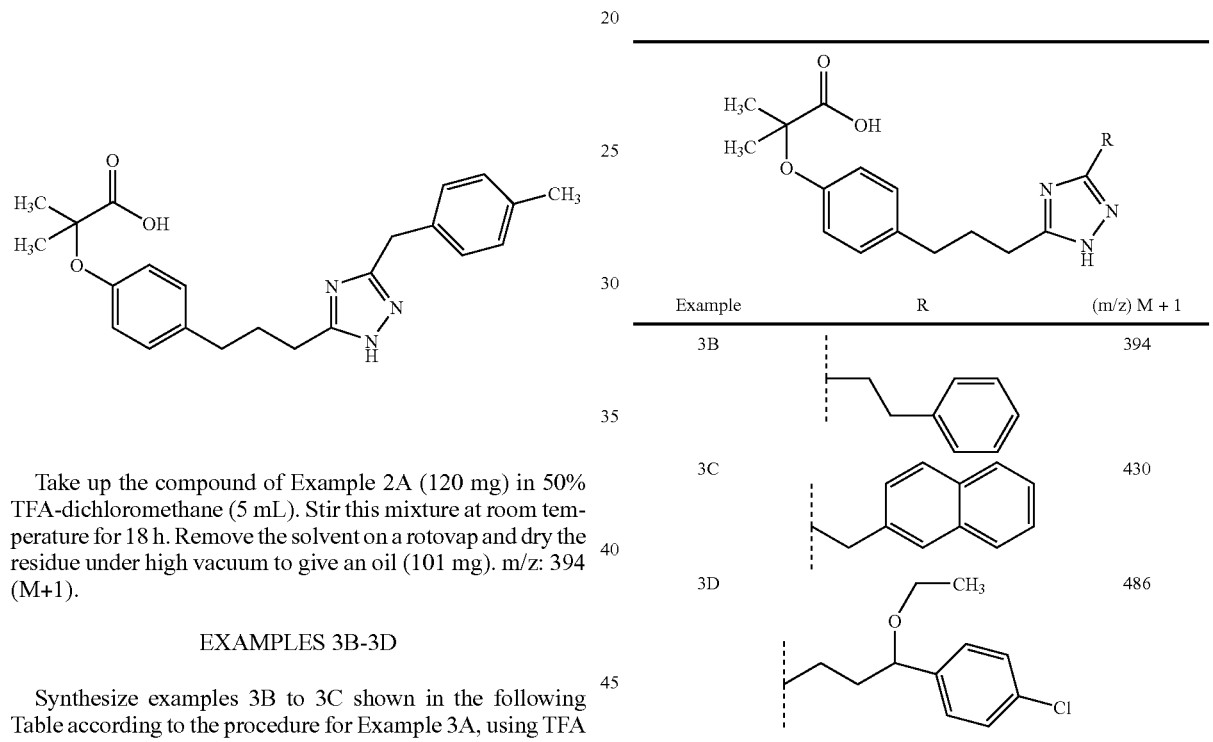

Take up the compound of Example 2A (120 mg) in 50% TFA-dichloromethane (5 mL). Stir this mixture at room temperature for 18 h. Remove the solvent on a rotovap and dry the residue under high vacuum to give an oil (101 mg). m/z: 394 (M+1).

EXAMPLES 3B-3D

Synthesize examples 3B to 3C shown in the following Table according to the procedure for Example 3A, using TFA mediated hydrolysis of appropriate t-butyl esters of Examples 2B to 2D.

EXAMPLE 4A

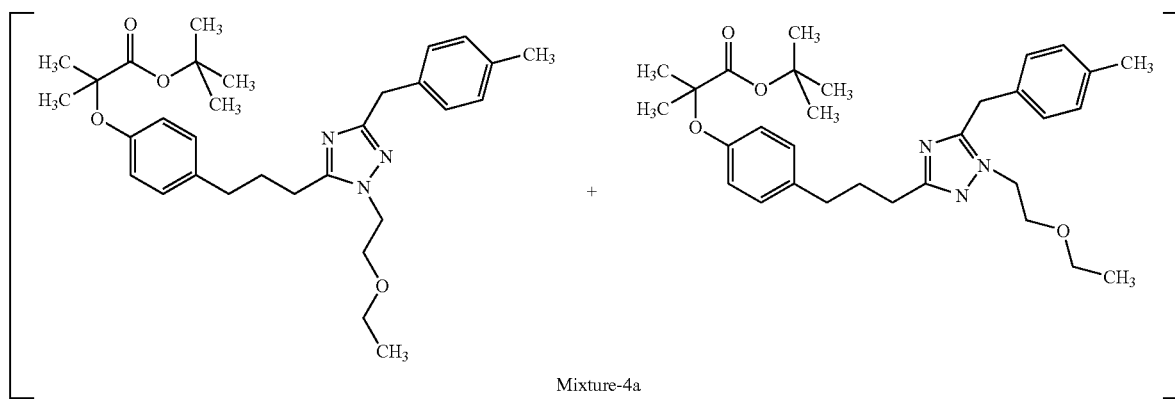

Mixture-4a

Add 2-ethoxyethylbromide (0.1 mL) to a solution of 2A (70 mg) in anhydrous DMF (1.5 mL) followed by anhydrous powdered K$_2$CO$_3$. Heat the reaction mixture at 50° C. with stirring for 18 h. Dilute the mixture with ethyl acetate (30 mL) and wash the ethyl acetate with water (3×30 mL). Dry the ethyl acetate layer (Na$_2$SO$_4$) and concentrate on a rotovap to give an oily residue. Purify the residue on a silica column to give approximate 40-60 regio-isomeric mixture of Example 4A as an oil (62 mg). m/z: 522 (M+1).

EXAMPLES 4B TO 4F

Synthesize Compounds 4B to 4F shown in the following Table according to the procedure for 4A from 2A using appropriate alkylbromide as shown in Table below.

Take up the triazole mixture Example 4A (61 mg) in 50% TFA-dichloromethane (4 mL). Stir this mixture at room temperature for 4 h. Remove the solvent on a rotovap and dry the residue under high vacuum to give regioisomeric mixture Example 5A an oil (30 mg). m/z: 466 (M+1)

EXAMPLES 5B TO 5F

Synthesize Example 5B to 5F shown in the following Table according to the procedure for 5A, by TFA mediated hydrolysis of tert-butyl esters Examples 4E to 4C.

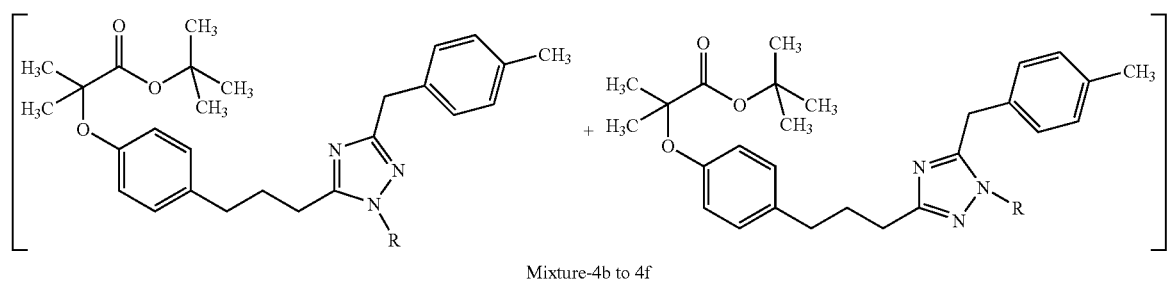

Mixture-4b to 4f

| Example | R | Alkylbromide Used | (m/z) M + 1 |
|---|---|---|---|
| 4B | 2-(2-methoxy)ethoxyethyl | 2-(2-methoxy)ethoxyethylbromide | 552 |
| 4C | 3-tetrahydropyranoxypropyl | 3-tetrahydropyranoxypropylbromide | 592 |
| 4D | 6-tetrahydropyranoxyhexyl | 6-tetrahydropyranoxyhexylbromide | 634 |
| 4E | 4-t-butylbenzyl | 4-t-butylbenzylbromide | 596 |
| 4F | 2-Oxobutyl | 1-Bromobutan-2-one | 520 |

EXAMPLE 5A

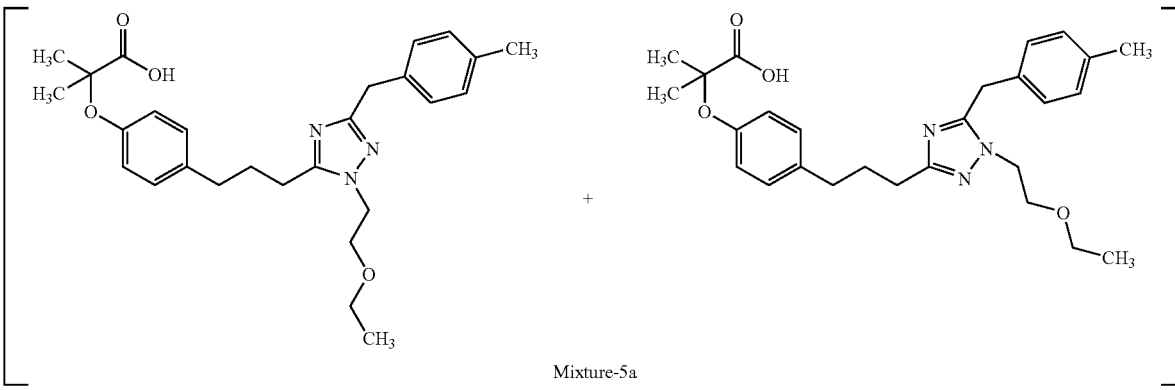

Mixture-5a

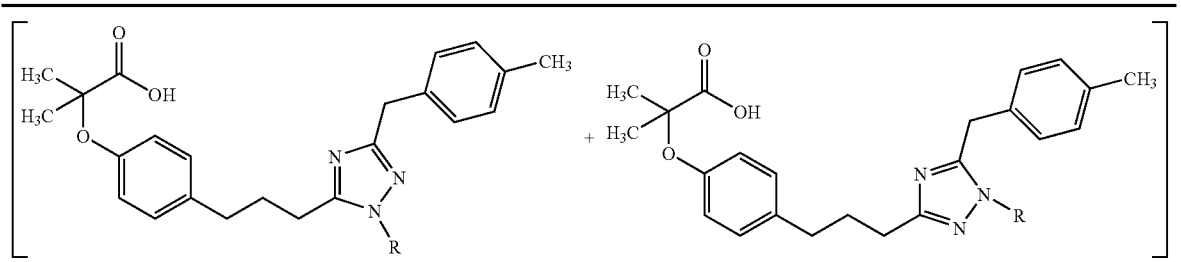

Mixture examples 5B to 5F

| Example | R | (m/z) M + 1 |
|---|---|---|
| 5B | -CH2CH2-O-CH2CH2-O-CH3 | 496 |
| 5C | -(CH2)3-OH | 452 |
| 5D | -(CH2)6-OH | 494 |
| 5E | -CH2-C6H4-C(CH3)3 | 540 |
| 5F | -CH2-C(=O)-CH2CH3 | 464 |

EXAMPLES 6 AND 7

Add conc. H$_2$SO$_4$ to a solution of mixture Example-5A (70 mg) in methanol (25 mL). Stir the reaction mixture at room temperature for 18 h. Remove the solvent to a small volume and dilute the residue with ethyl acetate (30 mL). Wash the ethyl acetate layer with water (3×30 mL), dry (Na$_2$SO$_4$), and concentrate on a rotovap to give an oily residue (71 mg). Purify the residue on a chiral HPLC column to give pure examples 6 and 7.

EXAMPLE 6

(15 mg), m/z: 480 (M+1).

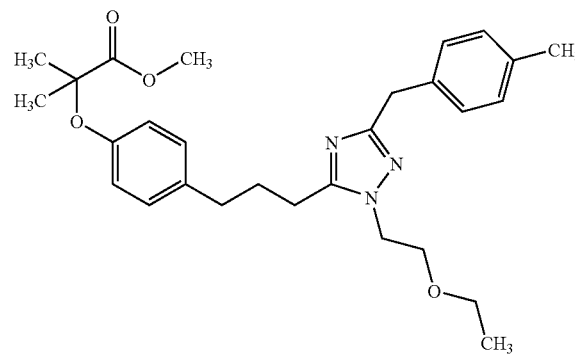

EXAMPLE 7

(19 mg), m/z: 480 (M+1).

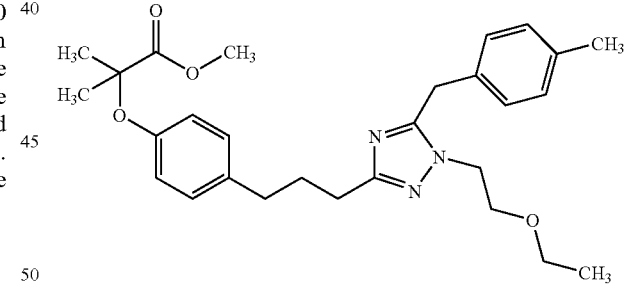

EXAMPLE 8

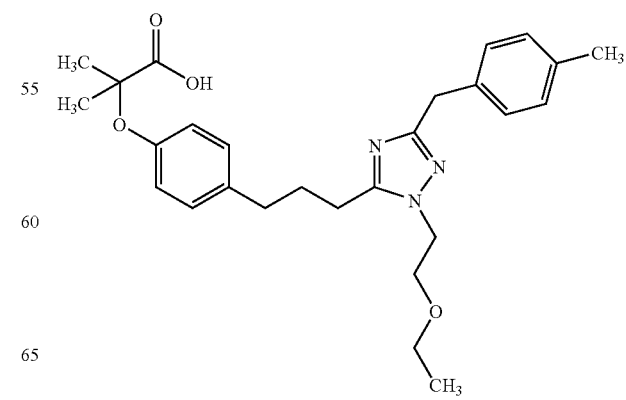

Take up the triazole ester Example 6 (15 mg) in methanol (2 mL). Add 2 N aqueous NaOH (1 mL) to this solution. Stir the mixture at room temperature for 2 h. Evaporate the solvent on the rotovap and dissolve the residue in water (5 mL). Acidify the solution to pH ~3 with 0.1 M aqueous HCl to give a milky solution. Extract the mixture with $CH_2Cl_2$ (3×10 mL). Dry the combined $CH_2Cl_2$ layers ($Na_2SO_4$), concentrate on a rotovap, and then dry under high vacuum to give Example 8 (11 mg). m/z: 466 (M+1).

EXAMPLE 9

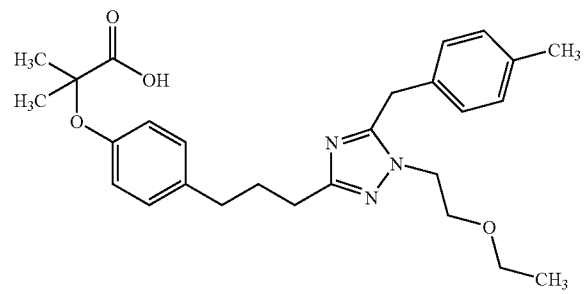

Synthesize example 9 according to the procedure for example 8 by NaOH mediated hydrolysis of ester example 6. m/z: 466 (M+1).

EXAMPLE 9a

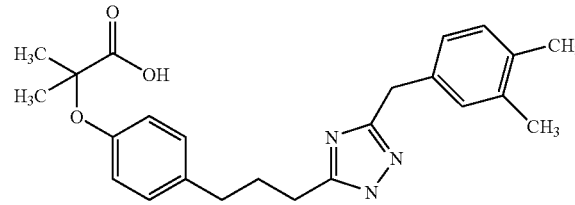

Synthesize Example 9a using the general method for Example 3A and Scheme I. m/z: 436.3.

EXAMPLE 10

2-Methyl-2-(4-{3-[5-(4-trifluoromethyl-phenyl)-2H-[1,2,4]triazol-3-yl]-propyl}-phenoxy)-propionic acid tert-butyl ester

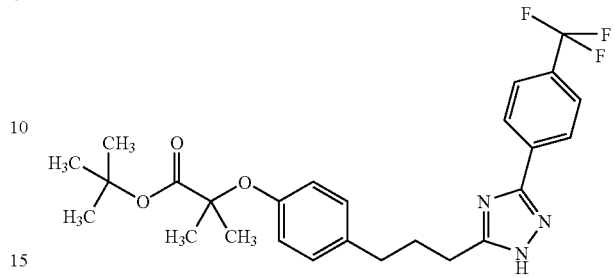

Add 4-(trifluoromethyl)benzonitrile (0.51 g, 3.0 mol) and potassium tert-butoxide (0.023 g, 0.21 mmol) to a solution of 2-[4-(3-Hydrazinocarbonyl-propyl)-phenoxy]-2-methyl-propionic acid tert-butyl ester (0.5 g, 1.5 mmol) in MeOH (5 mL). Stir the mixture at reflux overnight. Add an additional 0.2 equivalents of potassium tert-butoxide and stir the reaction for 24 h. Quench the crude with water, remove the MeOH in vacuo, and extract the aqueous layer with EtOAc. Separate the organic layer, dry with $MgSO_4$, and concentrate in vacuo. Purify the crude by Biotage (Hexane/EtOAc 4:1) yielding 0.32 g (44%) of the title compound, example 10 as a pale yellow oil. MS Data ($ES^+$) m/z 490.6 [M+H]

EXAMPLE 11

2-Methyl-2-(4-{3-[5-(4-trifluoromethyl-phenyl)-2H-[1,2,4]triazol-3-yl]-propyl}-phenoxy)-propionic acid

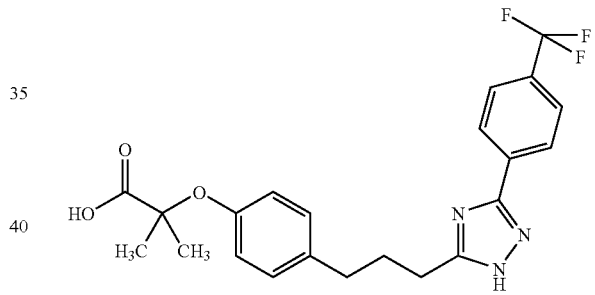

Add TFA (0.31 mL, 3.98 mmol) to a solution of example 10 (0.65 g, 1.33 mmol) in $CH_2Cl_2$ (6.5 ml). Stir the mixture at room temperature overnight. By TLC, a significant amount of starting material remains. Remove the solvent and residual TFA in vacuo. Purify the crude material by flash column chromatography (Hexane/EtOAc 2:1 and 1:1) yielding 0.16 g (28%) of example 10 as a white solid, and 0.4 g of the starting material recovered. MS Data ($ES^+$) m/z 434.3 [M+H].

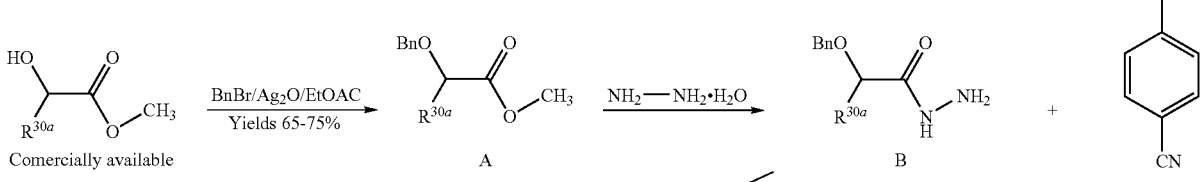

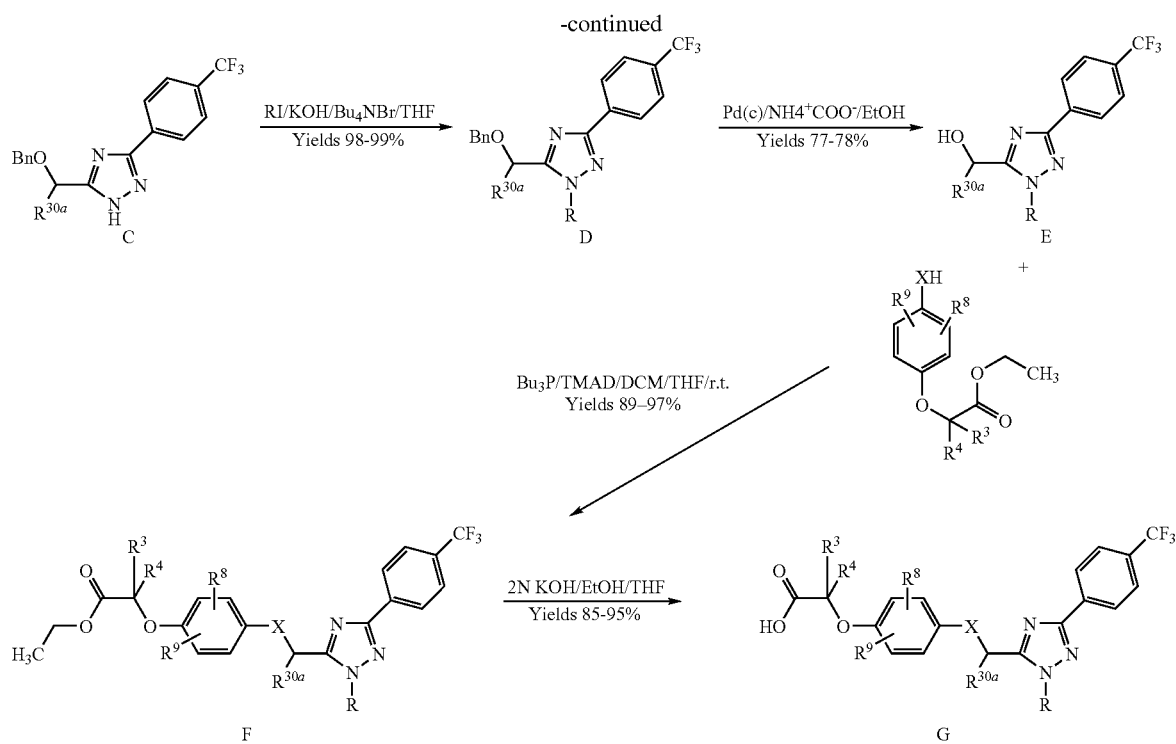

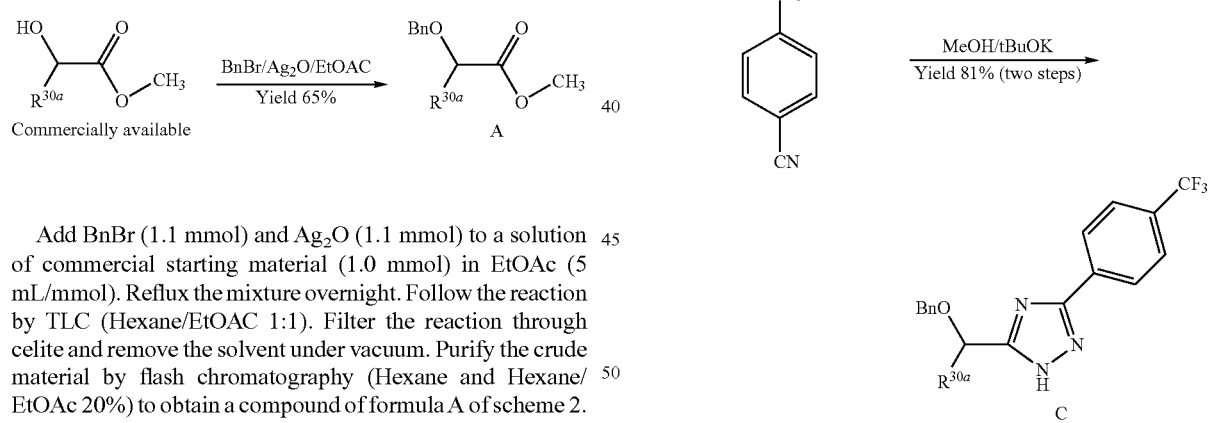

General Procedure for Scheme 2

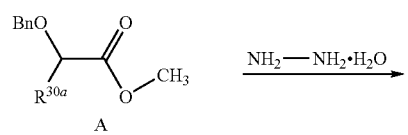

Add BnBr (1.1 mmol) and Ag₂O (1.1 mmol) to a solution of commercial starting material (1.0 mmol) in EtOAc (5 mL/mmol). Reflux the mixture overnight. Follow the reaction by TLC (Hexane/EtOAC 1:1). Filter the reaction through celite and remove the solvent under vacuum. Purify the crude material by flash chromatography (Hexane and Hexane/EtOAc 20%) to obtain a compound of formula A of scheme 2.

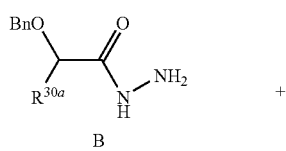

Dissolve the benzyl derivative compound of formula A of scheme 2 (1.0 mmol) in EtOH (0.8 M). Then, add hydrazine monohydrate (3.0 mmol). Stir the mixture at room temperature overnight. Follow the reaction by TLC (hexane/EtOAc 4:1). Remove the solvent under vacuum. Dissolve the residue in EtOAc and wash with water. Dry and concentrate the organic layer. Use the crude material without further purification. Add 4-(trifluoromethyl)benzonitrile (2.0 mol) and potassium tert-butoxide (0.6 mmol) to a solution of acylhydrazine a compound of formula B of scheme 2 (1.0 mmol) in MeOH (2.4 M). Stir the mixture at reflux 24 h. Follow the reaction by TLC (Hexane/EtOAc 4:1). Quench the crude material with water, remove the MeOH in vacuo and extract the aqueous layer with EtOAc. Separate the organic layer, dry with MgSO$_4$, and concentrate in vacuum. Purify the crude material by Biotage (Hexane/EtOAc 4:1) to obtain a compound of formula C of scheme 2.

organic layer, dry with MgSO$_4$, and concentrate in vacuum. Purify the crude material by Biotage (Hexane/EtOAc 7:1 and 4:1) to obtain a compound of formula D of scheme 2.

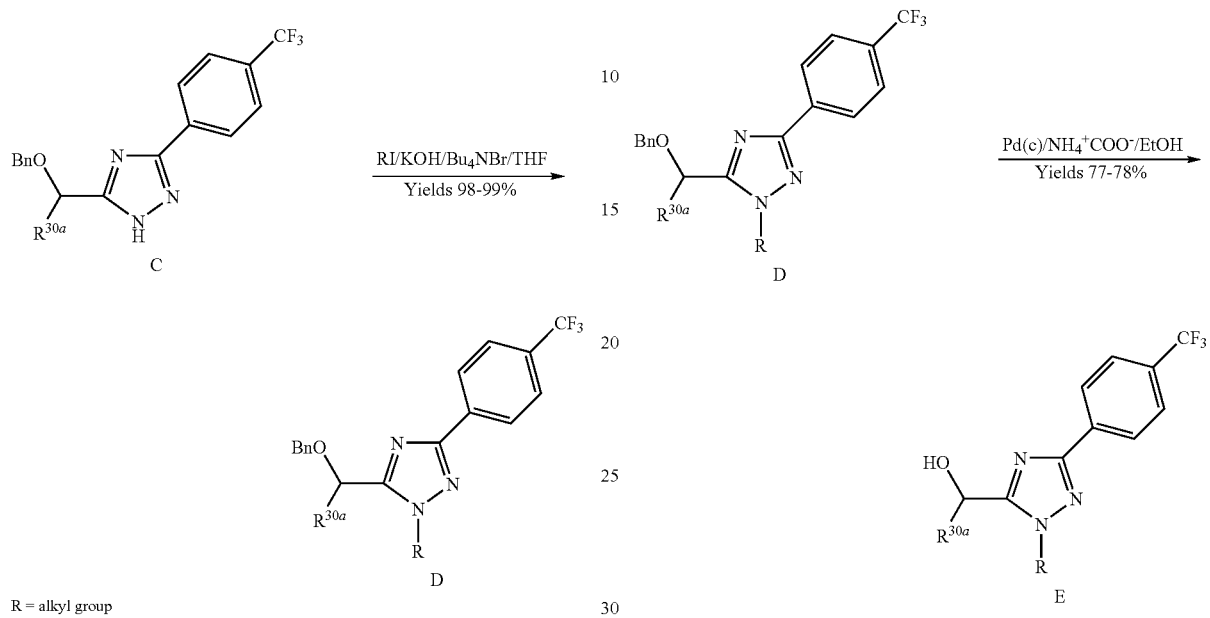

R = alkyl group

Triazole alkylation: Add powdered KOH (2.2 mmol), R—I (Br)(2.0 mmol) and Bu$_4$NBr (0.2 mmol) to a solution of the corresponding triazole derivate compound C of scheme 2 (1.0 mmol) in THF (5 mL/mmol). Stir the mixture at room temperature overnight. Follow the reaction by TLC (Hexane/EtOAc 4:1). Quench the crude with water and add EtOAc. Extract the aqueous layer with EtOAc (2×). Separate the Add Pd (C)(10-20% in weight) and NH$_4$$^+$COO$^-$ (10-20 mmol) to a solution of triazole compound of formula D of scheme 2 (1.0 mmol) in EtOH (5 mL/mmol). Stir the mixture at 80° C. overnight. Follow the reaction by TLC. Filter the reaction through celite and remove the solvent under vacuum. Purify the crude material by Biotage (Hexane/EtOAc 1:1) to obtain a compound of formula E of scheme 2.

Scheme 2A

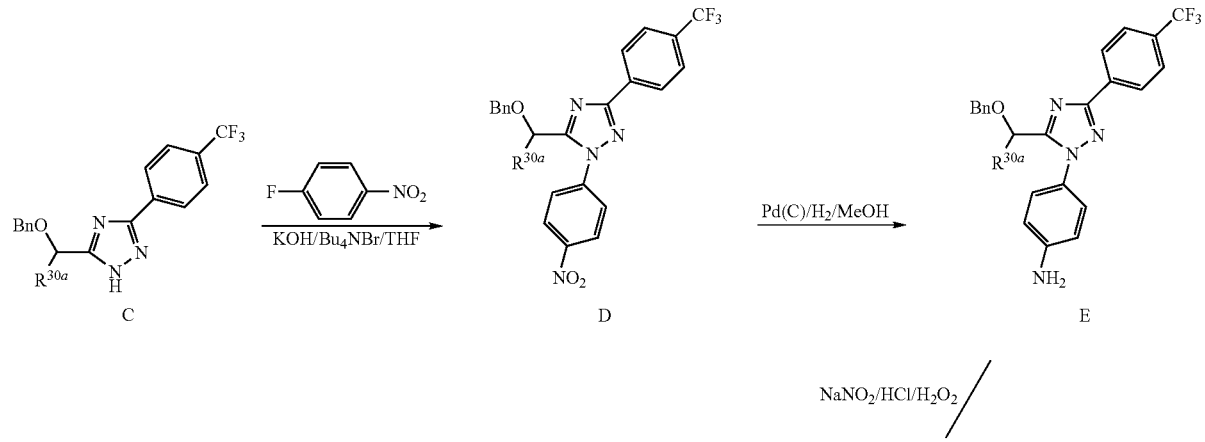

-continued

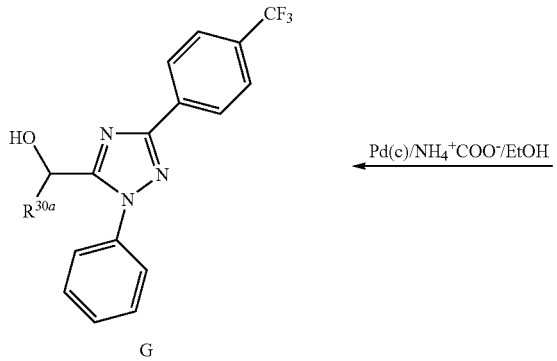

G

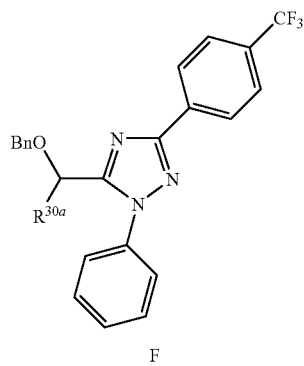

F

Add K$_2$CO$_3$ (1.1 mmol) and 4-fluoro-nitrobenzene (1.0 mmol) to a solution of the corresponding triazole derivate (C) of scheme 2a (1.0 mmol) in DMSO (20 mL/mmol) and stir the mixture to 90° C. overnight. Follow the reaction by TLC (Hexane/EtOAc 4:1). Quench the reaction with ice/water and add DCM. Extract again with 20% DCM/MeOH. Combine the organic layers and dry with MgSO$_4$, and concentrate in vacuum. Purify the crude by flash chromatography (Hexane/EtOAc 9:1) to obtain formula D of scheme 2A.

Add Pd (C)(10% in weight) to a solution of the triazole derivate formula D of scheme 2a (1.0 mmol) in EtOH (5 mL/mmol). Stir the mixture with and in an atmosphere of hydrogen overnight. Follow the reaction by TLC. Filter the solution mixture through celite and the remove the solvent under vacuum. Purify the crude (formula E of scheme 2A) without further purification.

Add 2N HCl solution (10.0 mmol) to a solution of the corresponding triazole derivate formula E of scheme 2A (1.0 mmol) in a mixture solvent (THF/CH$_3$COOH 8:1) (8 mL/mmol) at 0° C. and stir the mixture for 5 minutes at this temperature. Then, add NaNO$_2$ (1.0 mmol) in water (0.32 M) and then 3% H$_2$O$_2$ solution. Stir the reaction at 0° C. for 30 minutes and then for 1 hour at room temperature. Then, add EtOAc and extract the mixture with water. Dry the organic layers with MgSO$_4$ and concentrate in vacuum. Purify the crude by Biotage (Hexane/EtOAc 9:1) to obtain compound of formula F of scheme 2A (Yield 17%).

Add Pd (C)(10-20% in weight) and NH$_4$$^+$COO$^-$ (10-20 mmol) to a solution of a compound of formula F of scheme 2A (1.0 mmol) in EtOH (5 mL/mmol). Stir the mixture at 80° C. overnight. Follow the reaction by TLC. Filter the reaction through celite and remove the solvent under vacuum. Purify the crude by Biotage (Hexane/EtOAc 1:1) to obtain compound F of scheme 2a.

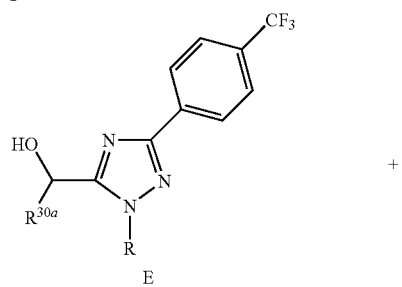

E

+

-continued

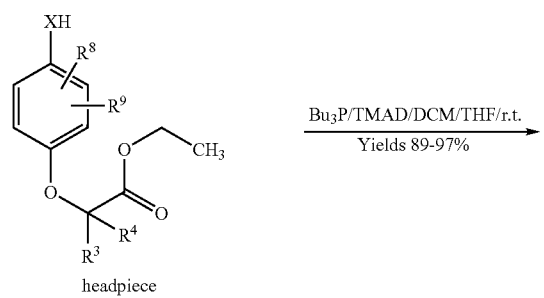

headpiece

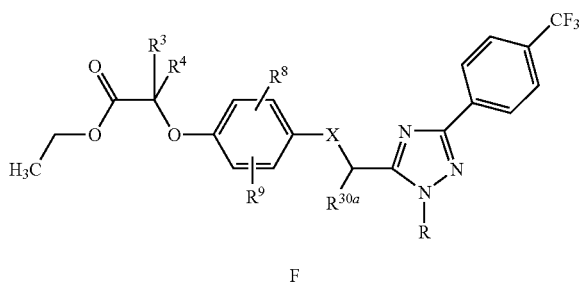

F

Mitsounobu reaction: Add the head piece (2 mmol), Bu$_3$P (2.0 mmol) and TMAD (2.0 mmol) to a solution of triazole derivate compound E of scheme 2 (1.0 mmol) in THF/DCM mixture (1:1)(10 mL/mmol). Stir the mixture at room temperature for 10-20 min. Follow the reaction by TLC. Remove the solvent under vacuum and then, add water and diethyl ether. Separate the organic layer and stir with a 2N NaOH solution for 10 min. Extract the mixture, dry the organic layer with MgSO$_4$, and concentrate in vacuum. Purify the crude by Biotage (Hexane/EtOAc 9:1) to obtain compound F of scheme 2.

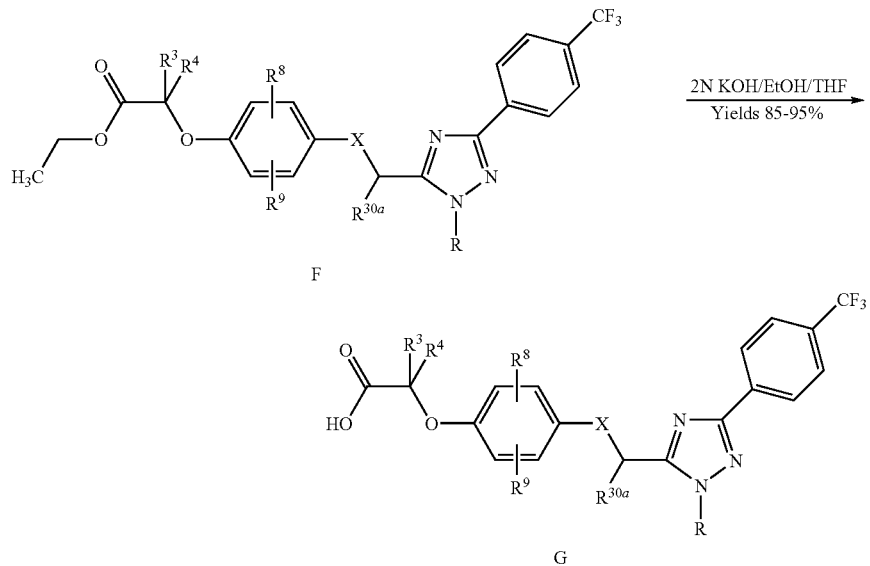

F

G

Add 2N KOH solution (10 mmol) to a solution of triazole derivate compound F of scheme 2 (1.0 mmol) in EtOH/THF mixture (1:1)(10 mL/mmol) and stir the mixture at room temperature overnight. Follow the reaction by TLC. Remove the solvent under vacuum and then, add water and EtOAc. Add 1N HCl solution until the pH is 5-7. Extract the mixture, wash the organic layer with water, separate, dry with MgSO$_4$, and concentrate in vacuum. Obtain the compound G of scheme 2.

SYNTHESIS OF EXAMPLE 13

Preparation 2

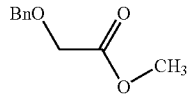

Add BnBr (72.7 mL, 0.61 mol, 1.1 eq) and Ag$_2$O (141.6 g, 0.61 mol, 1.1 eq) to a solution of methyl glycolate (50 g, 0.56 mol) in EtOAc (300 mL) and stir the mixture to reflux overnight. Follow the reaction by TLC (Hexane/EtOAC 1:1). Filter the reaction through celite and remove the solvent under vacuum. The oil is passed adsorbed onto flash silica. Place on top of a pad of flash silica (500 g) and elute with 20% ethyl acetate/hexane to give 75.8 g (75% yield) of a colorless oil.

Preparation 3

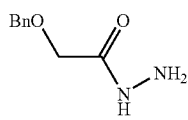

Dissolve preparation 2 (7.5 g, 41.6 mmol) in EtOH (100 mL). Then, add hydrazine monohydrate (6.05 mL, 124.9 mmol) and stir the mixture at room temperature overnight. Follow the reaction is by TLC (hexane/EtOAc 4:1). Remove the solvent under vacuum and dissolve the residue in EtOAc and wash with water. Dry the organic layer and concentrate and use the crude without further purification.

Preparation 4

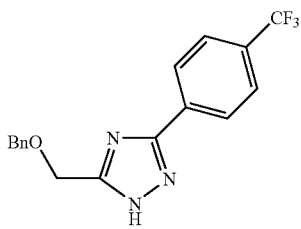

Add 4-(trifluoromethyl)benzonitrile (14.2 g, 83.2 mmol) and potassium tert-butoxide (2.8 g, 25 mmol) to a solution of preparation 3 in MeOH (100 mL) and stir mixture is at reflux for 24 h. Follow the reaction by TLC (Hexane/EtOAc 4:1). Quench the crude with water, remove the MeOH in vacuum, and extract the aqueous layer with EtOAc. Separate the organic layer, dry with MgSO$_4$, and concentrate in vacuum. Purify the crude by flash chromatography (Hexane/EtOAc 4:1) to obtain 11.2 g (81% yield) of preparation 4 as a white solid.

Preparation 5

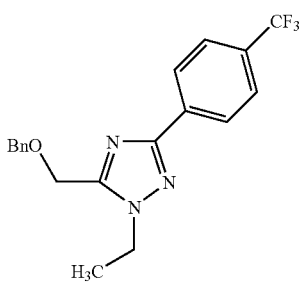

Add powdered KOH (0.37 g, 6.6 mmol), EtI (0.48 mL, 6.0 mmol) and Bu$_4$NBr (0.19 g, 0.6 mmol) to a solution of preparation 4 (1.0 g, 3.0 mmol) in THF (15 mL), and stir the mixture at room temperature overnight. Follow the reaction by TLC (hexane/EtOAc 4:1). Quench the crude with water and add EtOAc. Extract the aqueous layer with EtOAc (2×). Separate the organic layer, dry with MgSO$_4$, and concentrate in vacuo. Purify the crude by flash chromatography (Hexane/EtOAc 9:1) to obtain 1.09 g (99% yield) of preparation 5 as a white solid.

Preparation 6

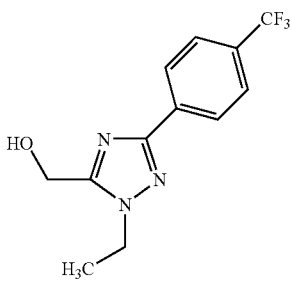

Add Pd (C)(20% in weight) and NH$_4$$^+$COO$^-$ (1.83 g, 10.0 mmol) to a solution of preparation 5 (1.05 g, 2.9 mmol) in EtOH (25 mL) and stir the mixture at 80° C. for 6 hours. Follow the reaction by TLC (Hexane/EtOAc 4:1). Filter the reaction through celite and remove the solvent under vacuum to obtain 0.88 g of preparation 6 as a white solid that is used without further purification.

Preparation 7

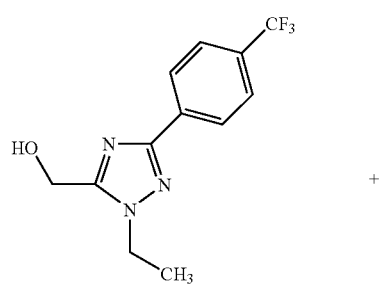

+

-continued

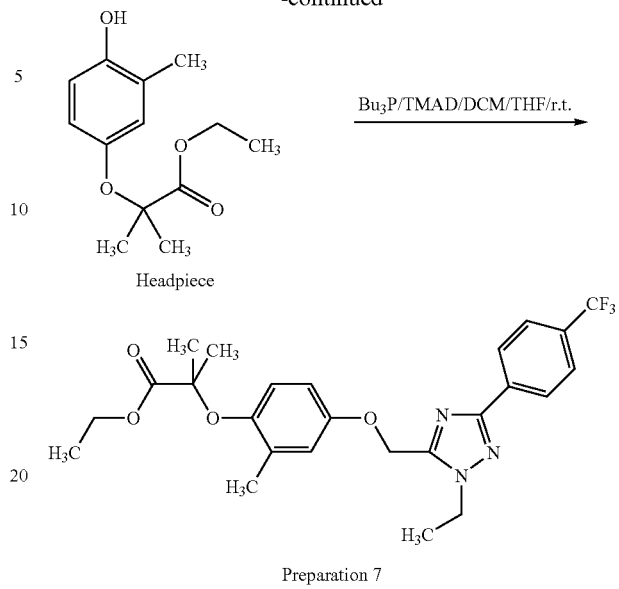

Headpiece

Preparation 7

Add the headpiece (1.38 g, 5.8 mmol), Bu$_3$P (1.44 mL, 5.8 mmol) and TMAD (0.99 g, 5.8 mmol) to a solution of preparation 6 (0.88 g, 2.9 mmol) in THF/DCM mixture (1:1)(15+15 mL) and stir the mixture at room temperature for 1 h. Follow the reaction by TLC (Hexane/EtOAc 1:1). Remove the solvent under vacuum. Then, add water and diethyl ether. Separate the organic layer, and stir with 2N NaOH solution for 10 min. Extract the mixture and dry the organic layer with MgSO$_4$, and concentrate in vacuo. Purify the crude by Biotage [40+S] (Hexane/EtOAc 9:1) to obtain 0.99 g (70% yield) of preparation 7 as a white solid. MS Data (ES$^+$) m/z 492.3 [M+H]. 350 mg (fraction B) of impure compound were reserved.

EXAMPLE 13

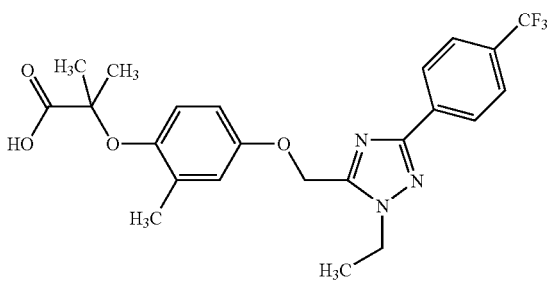

Add 2N KOH solution (10 mL, 19.9 mmol) to a solution of preparation 7 (0.98 g, 1.99 mmol) in EtOH/THF mixture (1:1)(10+10 mL), and stir the mixture at room temperature overnight. Follow the reaction by TLC (Hexane/EtOAc 1:1). Remove the solvent under vacuum. Then, add water and Et$_2$O and stir the mixture for 2 min. Isolate the organic layer and add 1N HCl solution over aqueous phase until pH 5-7. Filter the white solid precipitate and wash with water. Dry under vacuum to obtain: 0.80 g (87% yield) of Example 13 (Purity 97%). MS Data (ES$^+$) m/z 464.2 [M+H].

Prepare Examples 12 and 14-34 by a similar procedure for the preparation of Example 13.

| Example | Structure | LC/MS [M + 1] |
|---|---|---|
| 12 | 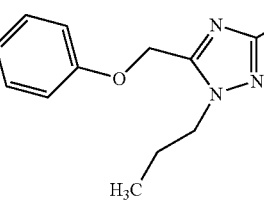 | 464.4 |
| 13 | 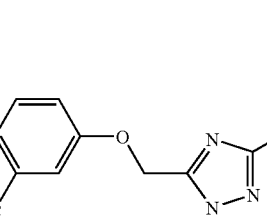 | 464.2 |
| 14 | 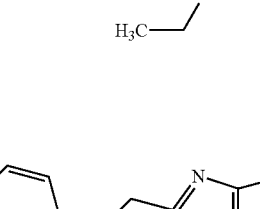 | 478.1 |
| 15 | 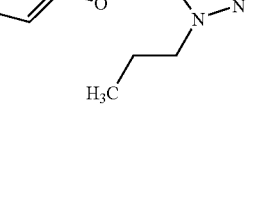 | 450.4 |
| 16 | 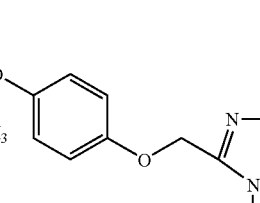 racemic | 478.3 |

-continued
| Example | Structure | LC/MS [M + 1] |
|---|---|---|
| 17 | 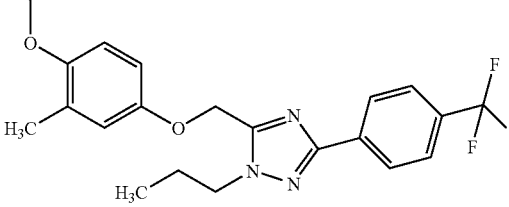 | 450.0 |
| 18 | 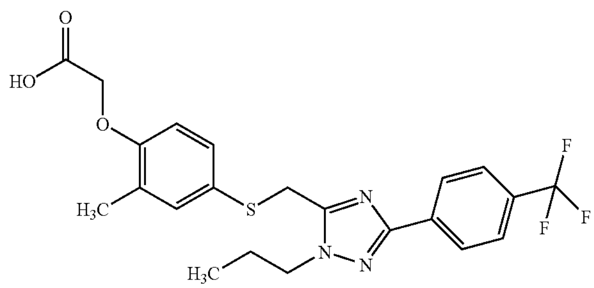 | 466.0 |
| 19 | 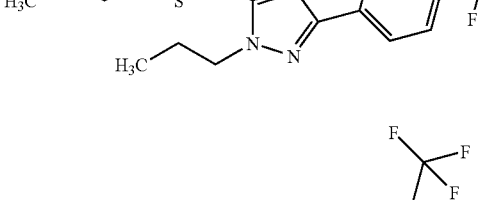 | 498.0 |
| 20 | 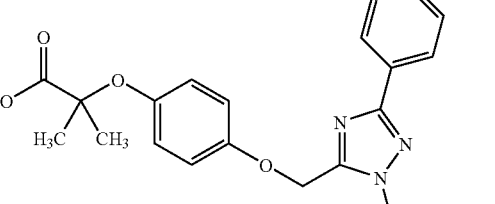 | 436.1 |

-continued
| Example | Structure | LC/MS [M + 1] |
|---------|-----------|---------------|
| 21 | 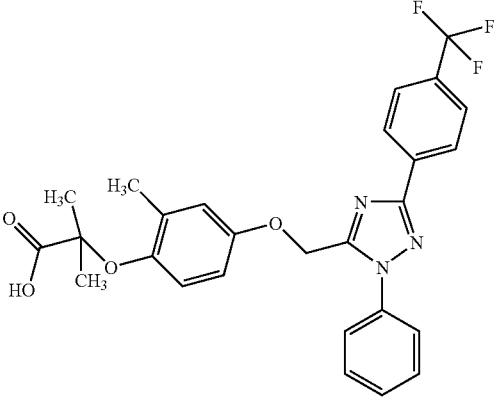 | 511.9 |
| 22 | 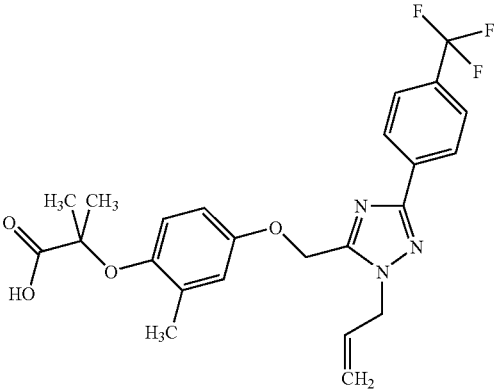 | 475.9 |
| 23 | 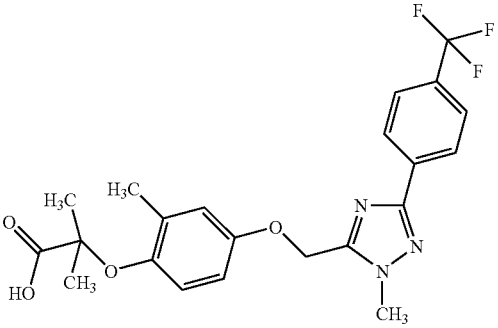 | 450.1 |
| 24 | 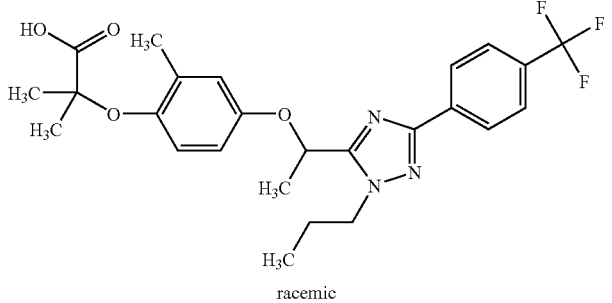
racemic | 492.3 |

-continued

| Example | Structure | LC/MS [M + 1] |
|---|---|---|
| 25 | 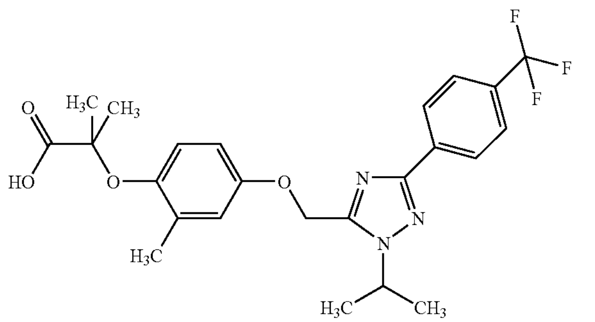 | 478.3 |
| 26 | 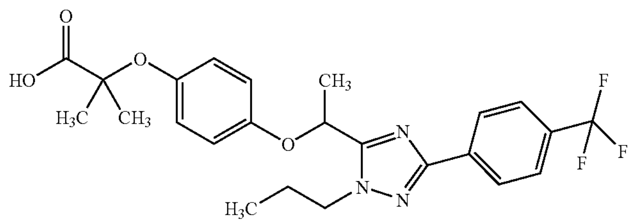 | 478.1 |
| 27 | 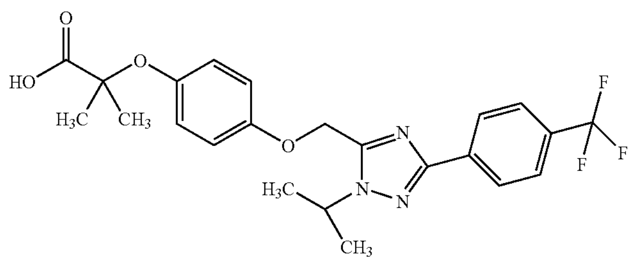 | 464.2 |
| 28 | 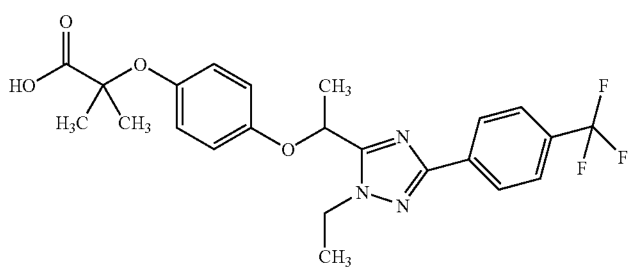 | 464.2 |
| 29 | 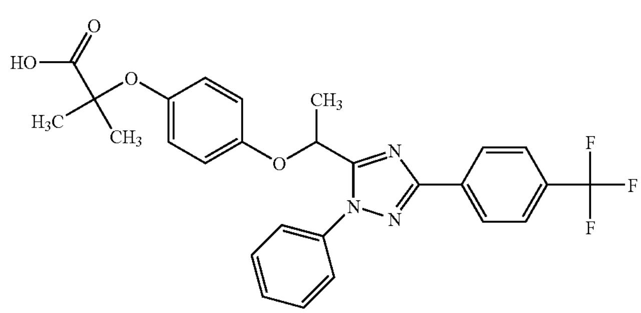 | 512.2 |

-continued
| Example | Structure | LC/MS [M + 1] |
|---------|-----------|---------------|
| 30 | 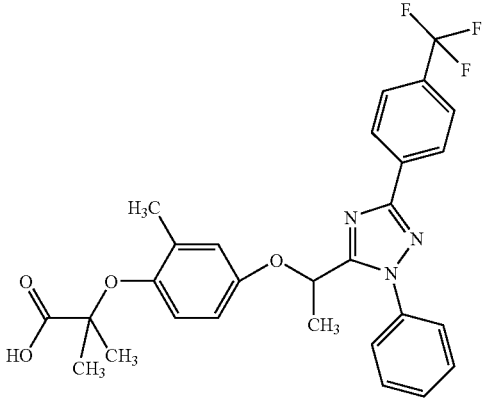 racemic | 526.2 |
| 31 | 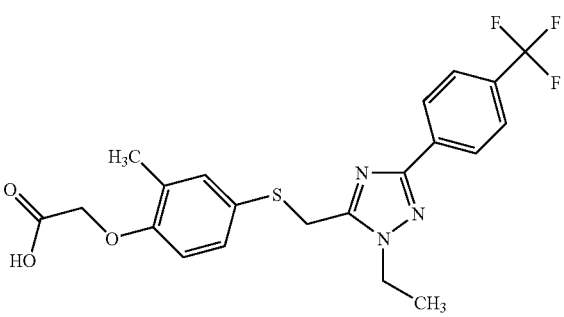 | 452.2 |
| 32 | 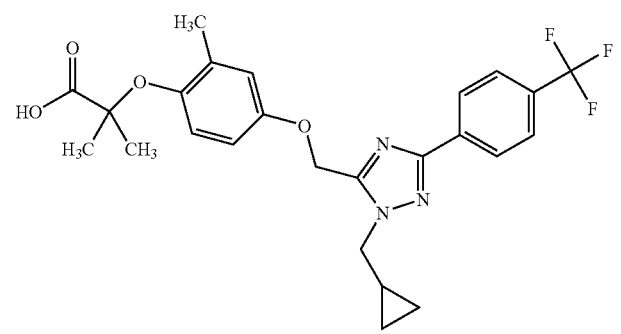 | 490.1 |
| 33 | 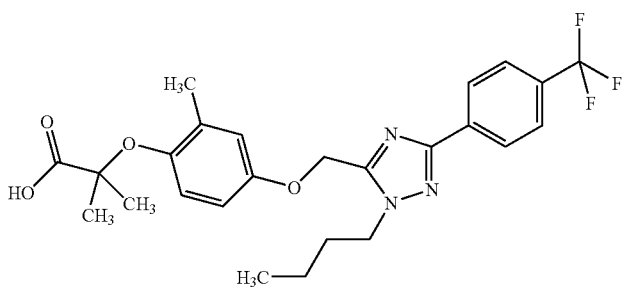 | 492.3 |

-continued
| Example | Structure | LC/MS [M + 1] |
|---------|-----------|---------------|
| 34 | 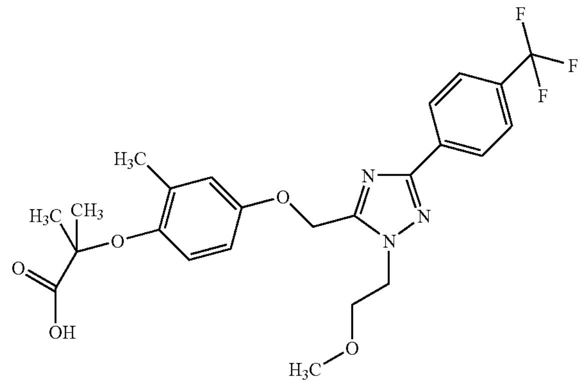 | 494.2 |
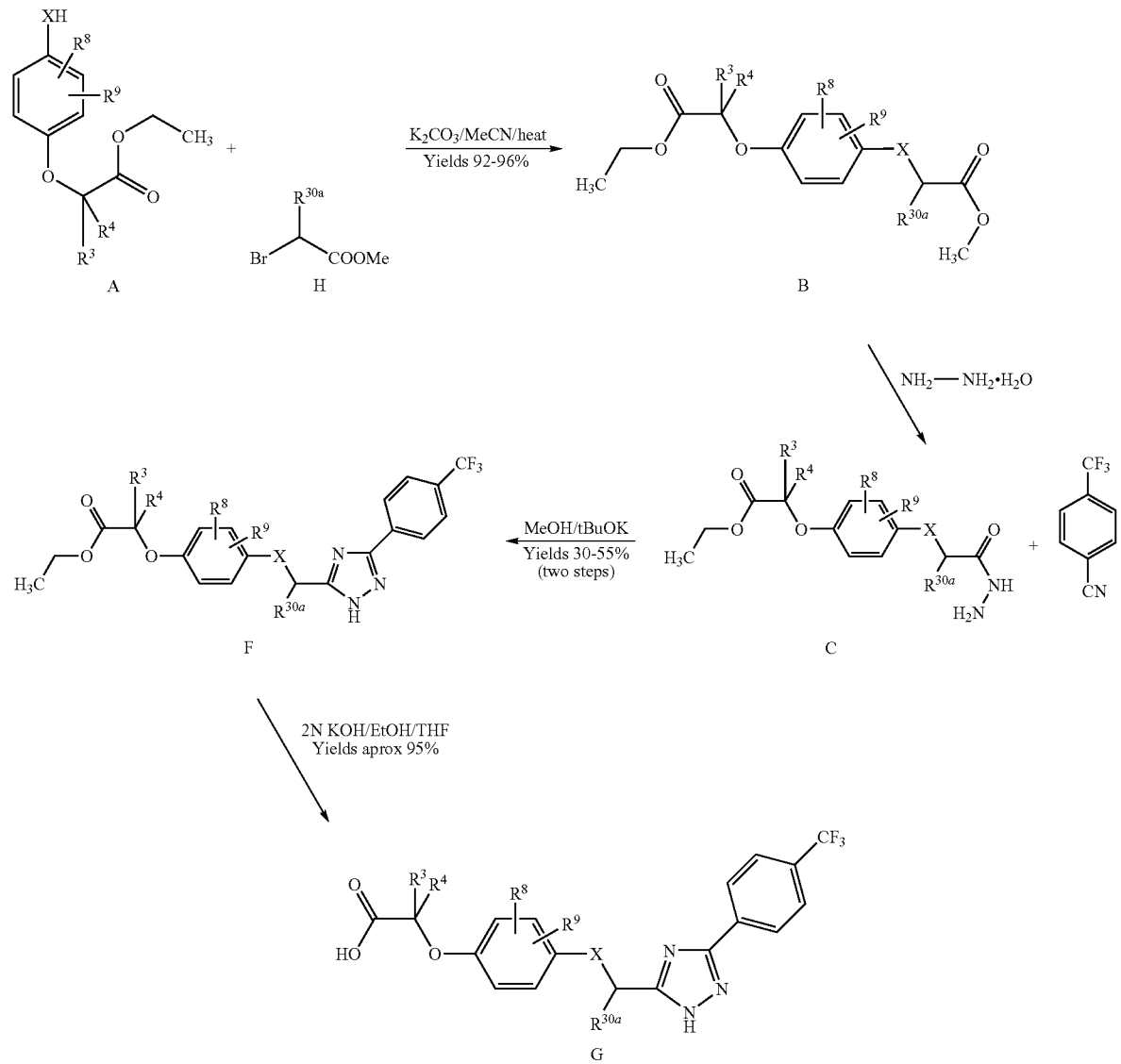

General Procedure for Scheme 3

Add $K_2CO_3$ (3.0 mmol) and compound of formula A of scheme 3 (1.0 mmol) to a solution of the bromoesther derivate (compound of formula H of scheme 3)(1.2 mmol) in MeCN (5 mL/mmol). Stir the mixture at reflux overnight. Follow the reaction by TLC (Hexane/EtOAc 4:1). Remove the solvent under vacuum and then, add water and EtOAc. Extract the mixture, dry the organic layer with $MgSO_4$, and concentrate in vacuum. Purify the crude by flash chromatography (Hexane/EtOAc 6:1) to obtain compound B of scheme 3.

Dissolve ester compound of formula B of scheme 3 (1.0 mmol) in EtOH (0.8 M). Then, add hydrazine monohydrate (3.0 mmol). Stir the mixture at room temperature overnight. Follow the reaction by TLC (hexane/EtOAc 4:1). Remove the solvent under vacuum. Dissolve the residue in EtOAc and wash with water. Dry the organic layer and concentrate. Use the crude without further purification. Add 4-(trifluoromethyl)benzonitrile (2.0 mol) and potassium tert-butoxide (0.6 mmol) to a solution of acylhydrazine compound of formula C of scheme 3 (1.0 mmol) in EtOH (2.4 M). Stir the mixture at reflux 24 hours. Follow the reaction by TLC (hexane/EtOAc 4:1). Quench the crude with water, remove the MeOH in vacuo, and extract the aqueous layer with EtOAc. Separate the organic layer, dry with $MgSO_4$, and concentrate in vacuum. Purify the crude by Biotage (Hexane/EtOAc 6:1) to obtain the compound of formula F of scheme 3 as a colorless oil.

Add 2N KOH solution (10 mmol) to a solution of triazole derivate compound of formula F of scheme 3 (1.0 mmol) in EtOH/THF mixture (1:1)(10 mL/mmol). Stir the mixture at room temperature overnight. Follow the reaction by TLC. Remove the solvent under vacuum. Then, add water and EtOAc. Add 1N HCl solution until pH 5-7. Extract the mixture, wash the organic layer with water, separate, dry with $MgSO_4$, and concentrate in vacuum. Obtain the products of the compound of formula G of scheme 3 as white solids.

SYNTHESIS OF EXAMPLE 36

Preparation 8

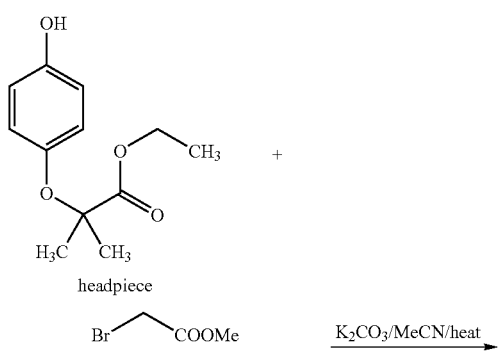

-continued

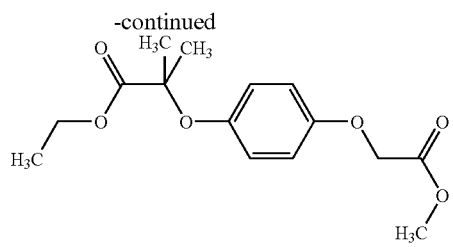

Preparation 8

Add $K_2CO_3$ (9.23 g, 66.9 mmol) and headpiece (5.0 g, 22.3 mmol) to a solution of commercially available bromoesther derivate (2.54 mL, 26.8 mmol) in MeCN (100 mL) and stir the mixture at reflux overnight. Follow the reaction by TLC (Hexane/EtOAc 4:1). Remove the solvent under vacuum. Then, add water and EtOAc. Extract the mixture and dry the organic layer with $MgSO_4$ and concentrate in vacuum. Purify the crude by flash chromatography (Hexane/EtOAc 19:1) to obtain preparation 8 as a colorless oil (6.59 g).

Preparation 9

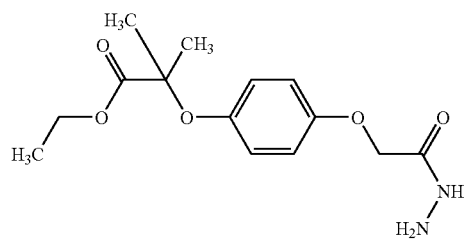

Dissolve preparation 8 (6.59 g, 22.3 mmol) in EtOH (30 mL). Then, add hydrazine monohydrate (4.32 mL, 89.2 mmol) and stir the mixture at room temperature overnight. Follow the reaction by TLC (hexane/EtOAc 4:1). Remove the solvent under vacuum. Dissolve the residue in EtOAc and wash with water. Dry the organic layer and concentrate. Use the crude preparation 9 without further purification.

Preparation 10

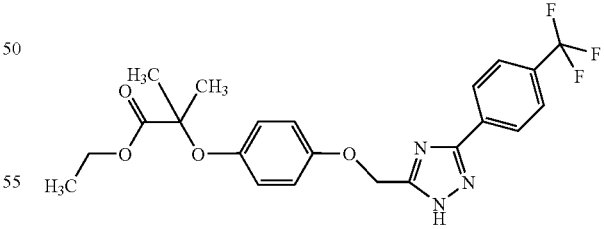

Add 4-(trifluoromethyl)benzonitrile (4.72 g, 27.6 mmol) and potassium tert-butoxide (0.93 g, 8.3 mmol) to a solution of acylhydrazine preparation 9 (3.22 g, 10.9 mmol) in EtOH (50 mL) and stir the mixture at reflux 24 h. Follow the reaction by TLC (Hexane/EtOAc 4:1). Quench the crude with water, remove the MeOH in vacuo and extract the aqueous layer with EtOAc. Separate the organic layer, dry with $MgSO_4$, and concentrate in vacuum. Purify the crude by Biotage (Hexane/EtOAc 9:1 to 6:1) obtain preparation 10 as a white solid (2.28 g obtained, 47% yield two steps).

EXAMPLE 36

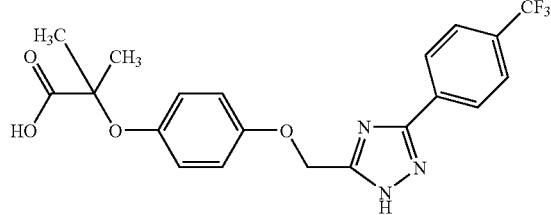

Add 2N KOH solution (2.7 mL, 4.5 mmol) to a solution of preparation 10 (200 mg, 0.45 mmol) in EtOH/H mixture (1:1)(8 mL) and stir the mixture at room temperature overnight. Follow the reaction by TLC. Remove the solvent under vacuum. The, add water and EtOAc. Add 1N HCl solution until pH 5-7. Extract the mixture and wash the organic layer with water, separate, dry with $MgSO_4$, and concentrate in vacuum. Obtain example 36 as white solids (164 mg, 87% yield).

Prepare Examples 35, 37 and 38 by a similar procedure for the preparation of Example 36.

| Example | Structure | LC/MS [M + 1] |
|---|---|---|
| 35 | 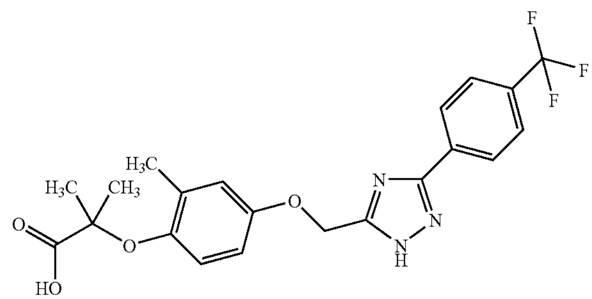 | 436.1 |
| 36 | 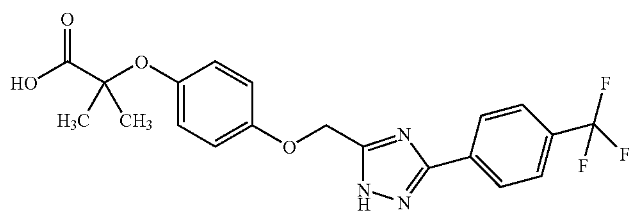 | 421.1 |
| 37 | racemic | 450.2 |
| 38 | racemic | 436.1 |

-continued
| Example | Structure | LC/MS [M + 1] |
|---|---|---|
| 38a | 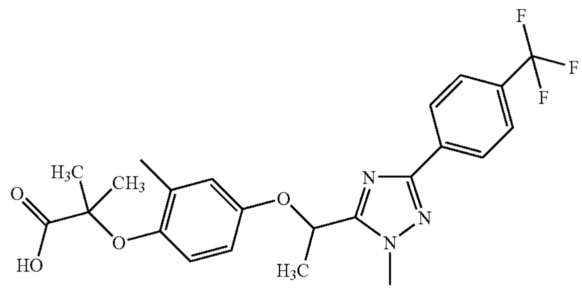 | |
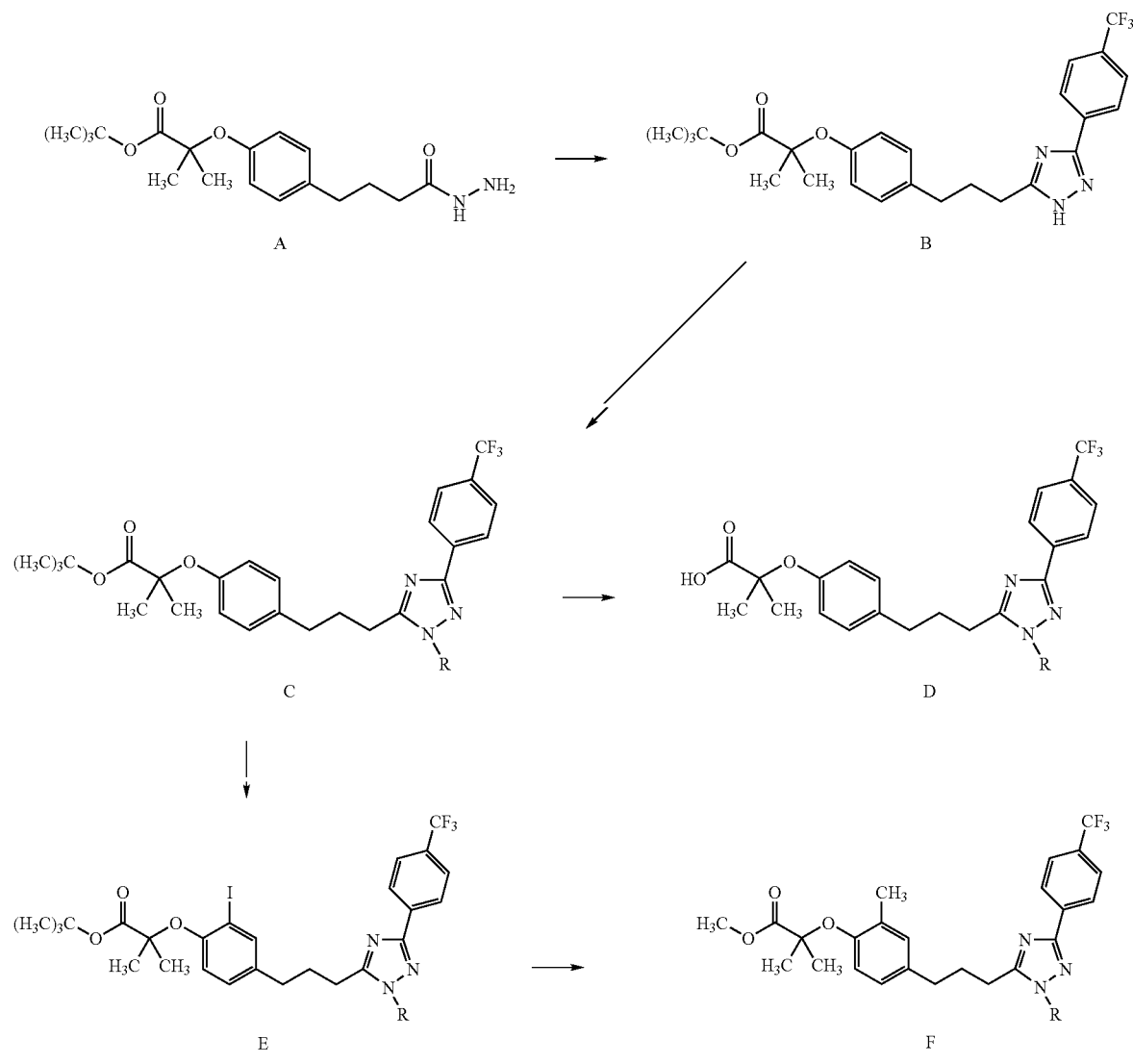
Scheme 4

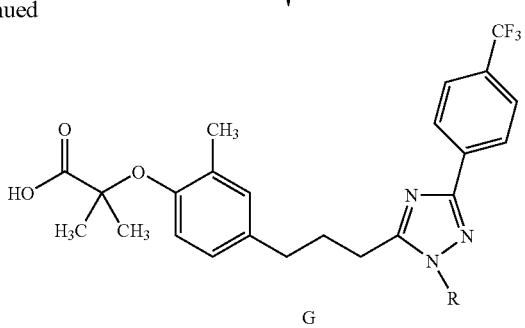

G

General Procedure for Scheme 4

Add 4-(trifluoromethyl)benzonitrile (3.0 mol) and potassium tert-butoxide (0.21 mmol) to a solution of a compound of formula A of scheme 4 (1.5 mmol) in MeOH (5 mL) and stir the mixture at reflux overnight. Add an additional 0.2 equivalents of potassium tert-butoxide and stir the reaction for 24 hours. Quench the crude with water, remove the MeOH in vacuo, and extract the aqueous layer with EtOAc. Separate the organic layer, dry with MgSO$_4$, and concentrate in vacuum. Purify the crude by Biotage (Hexane/EtOAc 4:1) yielding a compound of formula B of scheme 4.

R=Alkyl group

Triazole alkylation: Add powdered KOH (2.2 mmol), R—I (Br)(2.0 mmol) and Bu$_4$NBr (0.2 mmol) to a solution of the corresponding triazole compound of formula B of scheme 4 (1.0 mmol) in THF (5 mL/mmol) and stir the mixture at room temperature overnight. Follow the reaction by TLC (hexane/EtOAc 4:1). Quench the crude with water and add EtOAc. Extract the aqueous layer with EtOAc (2×). Separate the organic layer, dry with MgSO$_4$, and concentrate in vacuum. Purify the crude by Biotage (Hexane/EtOAc 7:1 and 4:1) to obtain a compound of formula C of scheme 4.

R=Aryl group (Ph and p-CF$_3$-Ph)

Coupling reaction: Add aryliodine (1.0 mmol), K$_2$CO$_3$ (2.0 mmol), Cu(OAc)$_2$ (0.01 mmol) and trans-1,2-diaminocyclohexane (0.07 mmol) to a solution of the corresponding triazole derivate compound of formula B of scheme 4 (1.2 mmol) in anhydrous dioxane (5 mL/mmol) under N$_2$. Stir the mixture to 110° C. overnight. Follow the reaction by TLC (Hexane/EtOAc 4:1). Filter the reaction through celite and extract the organic layer with water. Extract the aqueous layer with EtOAc (2×), separate the organic layer, dry with MgSO$_4$, and concentrate in vacuum. Purify the crude by Biotage (Hexane/EtOAc 9:1) to obtain compound of formula C of scheme 4.

Scheme 4a

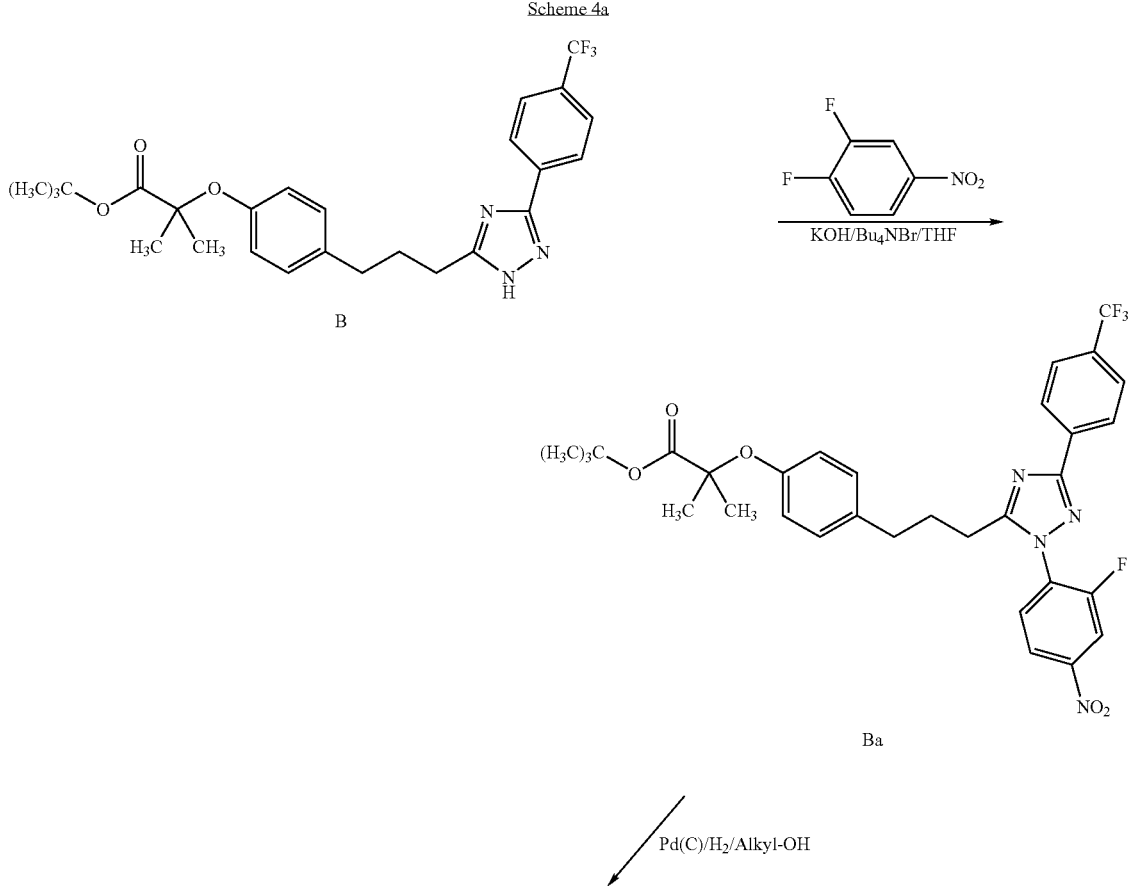

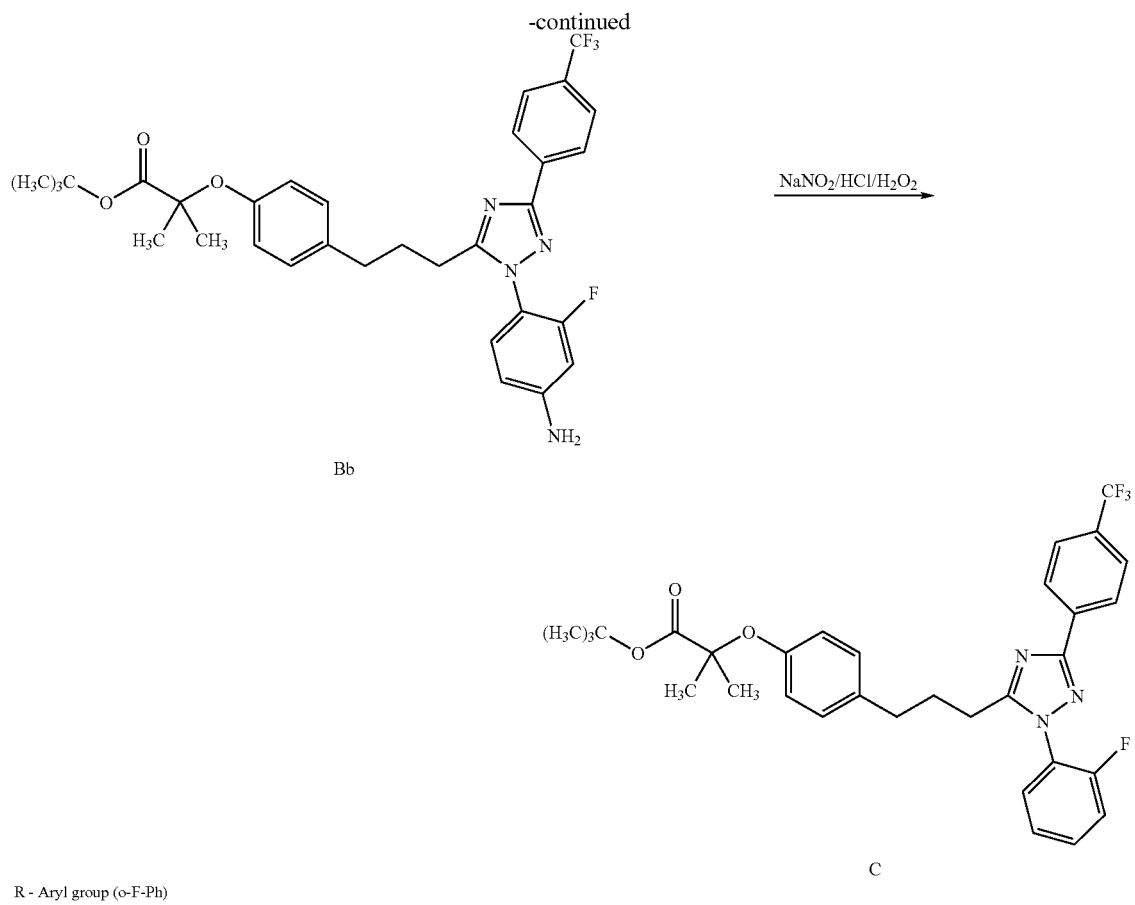

R - Aryl group (o-F-Ph)

Add $K_2CO_3$ (1.1 mmol) and 3,4-difluoro-nitrobenzene (1.0 mmol) to a solution of the corresponding triazole compound of formula B (1.0 mmol) in DMSO (20 mL/mmol) and stir the mixture to 90° C. overnight. Follow the reaction by TLC (Hexane/EtOAc 4:1). Quench the crude with ice/water and add DCM. Extract a second extraction with 20% DCM/MeOH. Combine the organic layers, dry with $MgSO_4$, and concentrate in vacuum. Purify the crude by flash chromatography (Hexane/EtOAc 9:1) to obtain a compound of formula Ba of scheme 4a.

Add Pd (C)(10% in weight) to a solution of triazole derivate (1.0 mmol) in alcohol (5 mL/mmol). Stir the mixture with and in an atmosphere of hydrogen overnight. Follow the reaction by TLC. Filter the solution mixture through celite and remove the solvent under vacuum and use the crude without further purification.

Add 2N HCl solution (10.0 mmol) to a solution of the corresponding triazole compound Bb of scheme 4a (1.0 mmol) in a mixture solvent (THF/$CH_3COOH$ 8:1)(8 mL/mmol) at 0° C. Stir the mixture 5 minutes at this temperature and add $NaNO_2$ (1.0 mmol) in water (0.32 M) and then 3% $H_2O_2$ solution (0.56 mL). Stir the reaction at 0° C. for 30 min and 1 hour at room temperature. Then, add EtOAc and extract the mixture with water. Dry the organic layer with $MgSO_4$ and concentrate in vacuum. Purify the crude by Biotage (Hexane/EtOAc 9:1) to obtain compound C of scheme 4a.

Add TFA (excess) to a solution of compound of formula C of scheme 4 (1.0 mmol) in $CH_2Cl_2$ (5 ml) and stir the mixture at room temperature overnight. Follow the reaction by TLC (Hexane/EtOAc 1:1). Remove the solvent and residual TFA in vacuum. Dissolve the residue in DCM and wash with a saturated solution of $NaHCO_3$. Dry the organic layer with $MgSO_4$ and concentrate in vacuum. Obtain the compound of formula D of scheme 4.

Add $I_2$ (2.0 mmol) and $AgSO_4$ (2.0 mmol) to a solution of the corresponding triazole compound of formula D of scheme 4 (1.0 mmol) in EtOH (8 mL/mmol) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with $MgSO_4$, and concentrate in vacuum. Purify the crude by Biotage (Hexane/EtOAc 7:1 and 4:1) to obtain a compound of formula E of scheme 4.

Add $MeB(OH)_2$ (3.0 mmol), CsF (3.0 mmol) and $PdCl_2$(dppf)(0.16 mmol) to a solution of the corresponding triazole compound of formula E of scheme 4 (1.0 mmol) in anhydrous Dioxane (10 mL/mmol) under $N_2$. Stir the mixture to 80° C. overnight. Follow the reaction by LC/MS. Cool the reaction, filter through celite, and remove the solvent under vacuum. Purify the crude by flash chromatography (Hexane/EtOAc 7:1 and 4:1 mixtures) to obtain a compound formula F of scheme 4.

Add TFA (excess) to a solution of a compound of formula F of scheme 4 (1.0 mmol) in $CH_2Cl_2$ (5 ml) and stir the mixture at room temperature overnight. Follow the reaction by TLC (Hexane/EtOAc 1:1). Remove the solvent and residual TFA in vacuum. Dissolve the residue in DCM and

SYNTHESIS OF EXAMPLE 47

Preparation 11

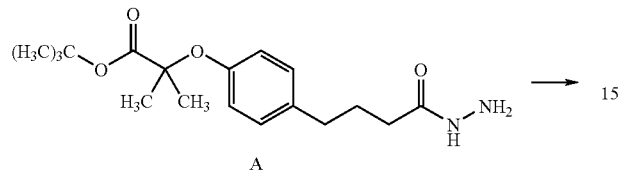

A

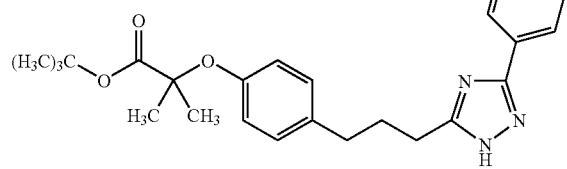

Preparation 11

Add 4-(trifluoromethyl)benzonitrile (0.51 g, 3.0 mol) and potassium tert-butoxide (0.023 g, 0.21 mmol) to a solution of A above (0.5 g, 1.5 mmol) in MeOH (5 mL) and stir the mixture at reflux overnight. Add an additional 0.2 equivalents of potassium tert-butoxide and stir the reaction for 24 h. Quench the crude with water, remove the MeOH in vacuo and extract the aqueous layer with EtOAc. Separate the organic layer, dry with MgSO$_4$, and concentrate in vacuo. Purify the crude by Biotage (Hexane/EtOAc 4:1) yielding 0.32 g (44%) preparation 11 as a pale yellow oil. MS Data (ES$^+$) m/z 490.6 [M+H].

Preparation 12

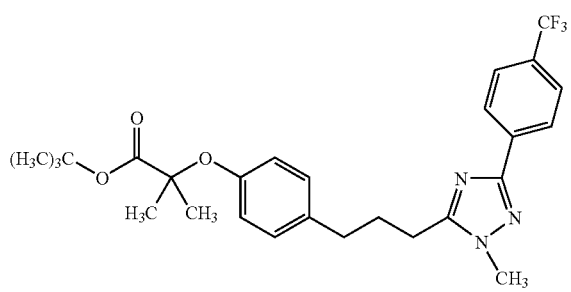

Add powdered KOH (0.14 g, 2.45 mmol), MeI (0.14 mL, 2.3 mmol) and Bu$_4$NBr (0.05 g, 0.15 mmol) to a solution of preparation 11 (0.75 g, 1.5 mmol) in THF (5 mL) and stir the mixture at room temperature overnight. Follow the reaction by TLC (hexane/EtOAc 4:1). Quench the crude with water and add EtOAc. Extract the aqueous layer with EtOAc (2×). Separate the organic layer, dry with MgSO$_4$, and concentrate in vacuo. Purify the crude by flash chromatography (Hexane/EtOAc 9:1) to obtain 0.51 g (66% yield) of preparation 12 a white solid.

Preparation 13

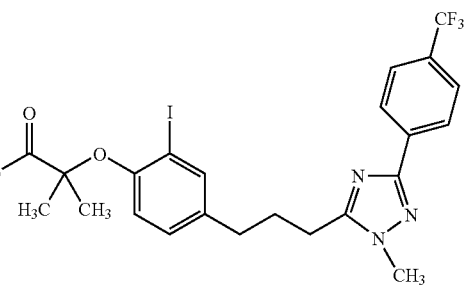

Add I$_2$ (0.2 g, 0.8 mmol) and AgSO$_4$ (0.25 g, 0.8 mmol) to a solution of preparation 12 (0.25 g, 0.5 mmol) in EtOH (5 mL) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with MgSO$_4$, and concentrate in vacuum. Purify the crude by Biotage (Hexane/EtOAc 9:1) to obtain 0.15 g (48% yield) of preparation 13 as a white solid.

Preparation 14

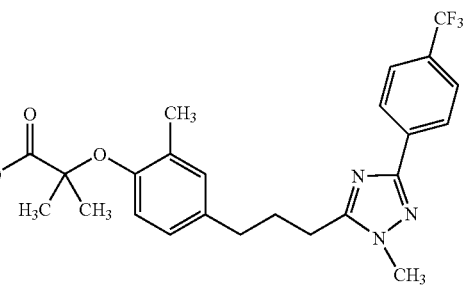

Add MeB(OH)$_2$ (0.04 g, 0.71 mmol), CsF (0.11 g, 0.71 mmol) and PdCl$_2$(dppf) (0.03 g, 0.04 mmol) to a solution of the preparation 13 (0.15 g, 0.24 mmol) in anhydrous Dioxane (2 mL) under N$_2$ and stir the mixture to 80° C. overnight. Follow the reaction by LC/MS. Cool and then filter the reaction through celite and remove the solvent under vacuum. Purify the crude by flash chromatography (Hexane/EtOAc 4:1 mixtures) to obtain 0.09 g (72% yield) of preparation 14 as a white solid.

EXAMPLE 47

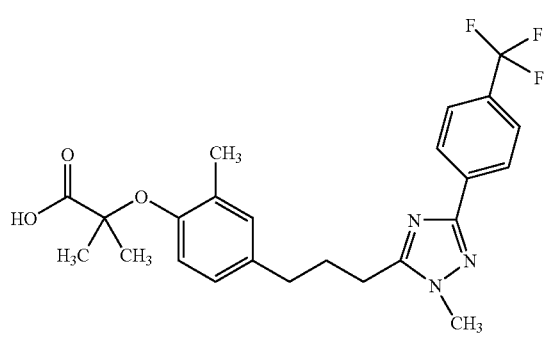

Add TFA (excess) to a solution of preparation 14 (0.09 g, 0.17 mmol) in $CH_2Cl_2$ (5 ml) and stir the mixture at room temperature overnight. Follow the reaction by TLC (Hexane/EtOAc 4:1). Remove the solvent and residual TFA in vacuum. Dissolve the residue in DCM and wash with saturated solution of $NaHCO_3$. Dry the organic layer with $MgSO_4$ and concentrate in vacuum. Obtain example 47 as a solid, 0.05 g (92% yield).

Prepare Examples 39-46 and 48-52 by a similar procedure for the preparation of example 47.

| Example | Structure | LC/MS [M + 1] |
|---|---|---|
| 39 | 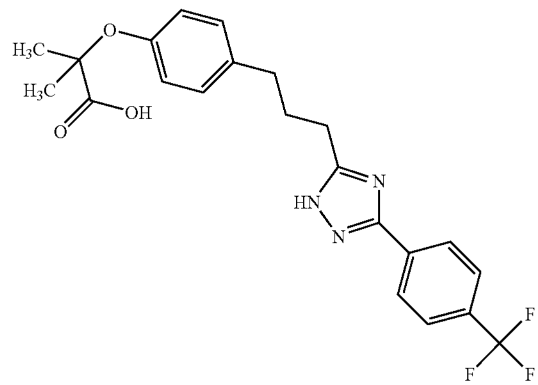 | 434.3 |
| 40 | 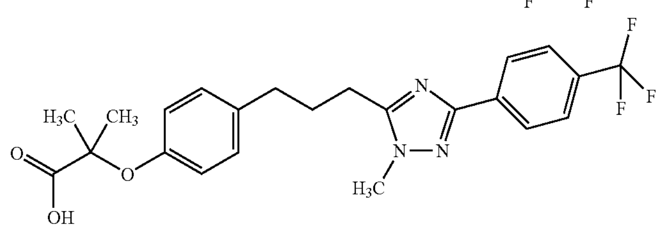 | 448.1 |
| 41 | 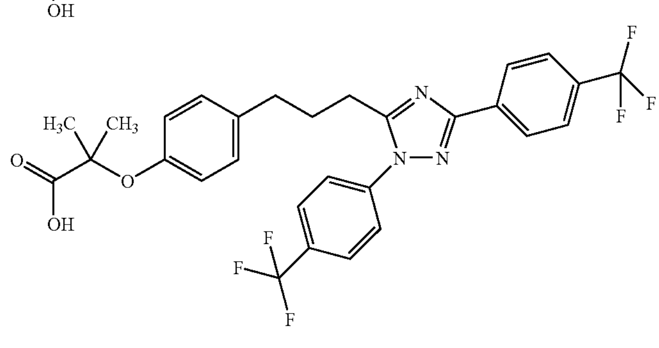 | 578.2 |
| 42 | 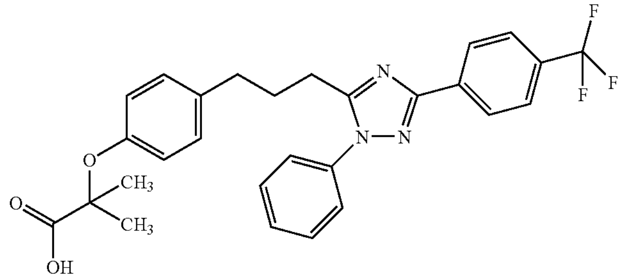 | Confirmed by $^1$H-NMR |

-continued

| Example | Structure | LC/MS [M + 1] |
|---|---|---|
| 43 | 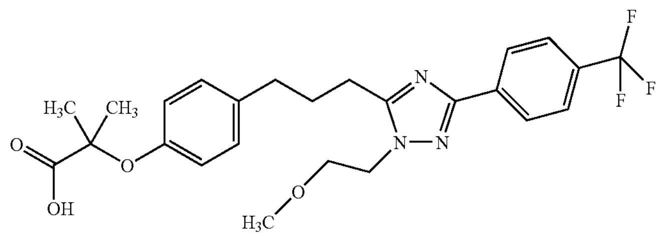 | 492.0 |
| 44 | 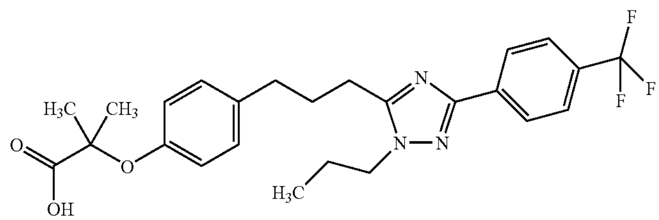 | Confirmed by ¹H-NMR |
| 45 | 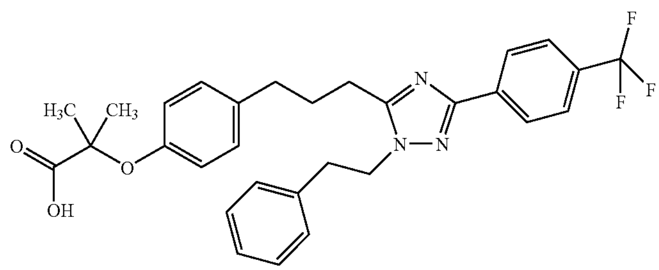 | Confirmed by ¹H-NMR |
| 46 | 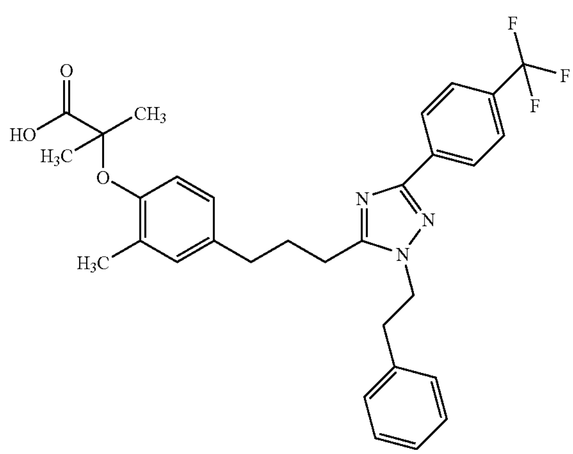 | 552.5 |
| 47 | 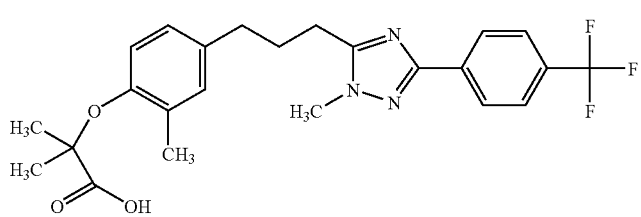 | 528.3 |

-continued

| Example | Structure | LC/MS [M + 1] |
|---|---|---|
| 48 | 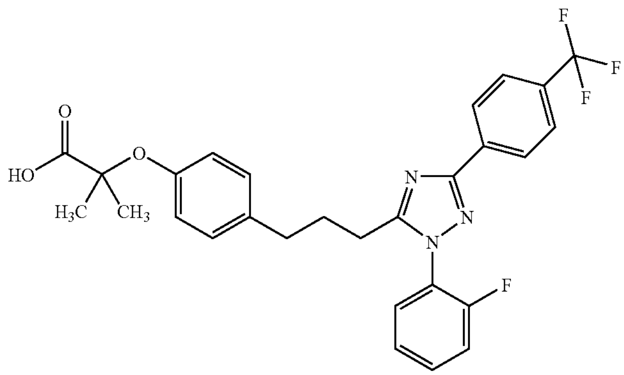 | 528.3 |
| 49 | 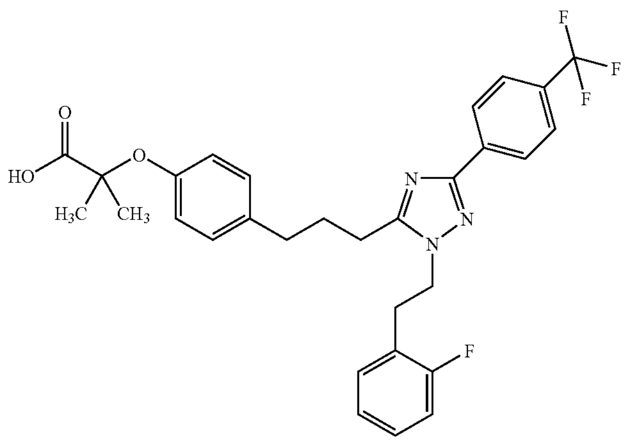 | 556.2 |
| 50 | 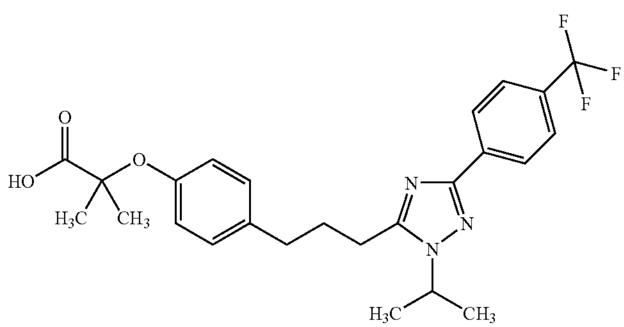 | 476.2 |
| 51 | 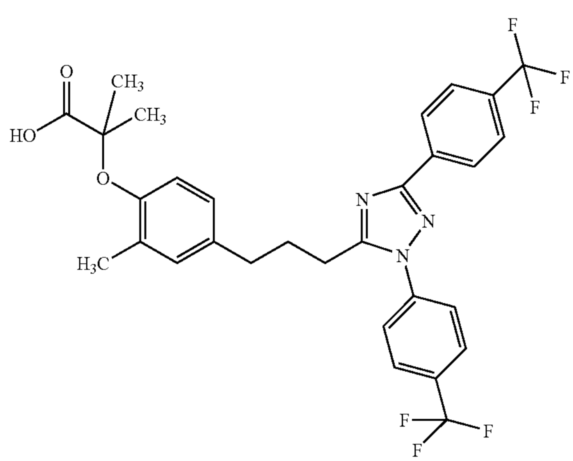 | 592.3 |

| Example | Structure | LC/MS [M + 1] |
|---|---|---|
| 52 | 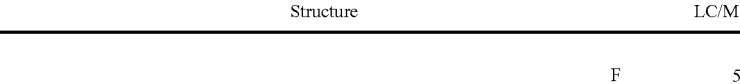 | 524.2 |
Scheme 5
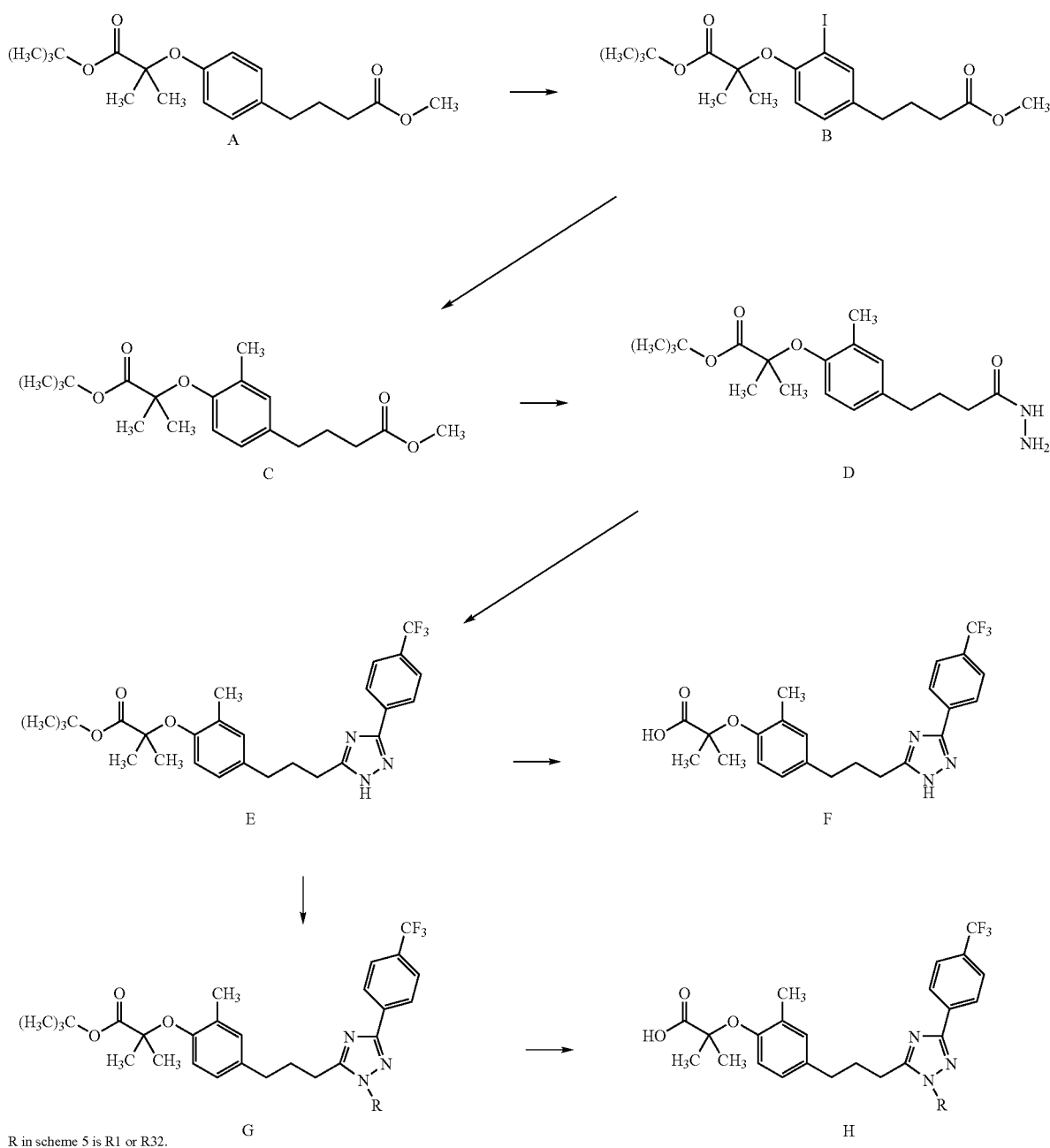
R in scheme 5 is R1 or R32.

General Procedure for Scheme 5

Add I$_2$ (1.1 mmol) and AgSO$_4$ (1.1 mmol) to a solution of a compound of formula A of scheme 5 (1.0 mmol) in EtOH (8 mL/mmol) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with MgSO$_4$, and concentrate in vacuum. Purify the crude by Biotage (Hexane/EtOAc 9:1) to obtain a compound of formula B of scheme 5.

Add MeB(OH)$_2$ (3.0 mmol), CsF (3.0 mmol) and PdCl$_2$(dppf)(0.16 mmol) to a solution of a compound of formula B of scheme 5 (1.0 mmol) in anhydrous Dioxane (10 mL/mmol) under N$_2$ and stir the mixture to 80° C. overnight. Follow the reaction by LC/MS. Cool, filter the reaction through celite, and remove the solvent under vacuum. Purify the crude by flash chromatography (Hexane/EtOAc 19:1 mixtures) to obtain a compound of formula C of scheme 5.

Dissolve the compound of formula C of scheme 5 (1.0 mmol) in EtOH (0.8 M). Then, add hydrazine monohydrate (3.0 mmol) and stir the mixture at room temperature overnight. Follow the reaction by TLC (hexane/EtOAc 4:1). Remove the solvent under vacuum. Dissolve the residue in EtOAc and wash with water. Dry the organic layer and concentrate and use the crude without further purification. Add 4-(trifluoromethyl)benzonitrile (2.0 mol) and potassium tert-butoxide (0.6 mmol) to a solution of acylhydrazine compound of formula D of scheme 5 (1.0 mmol) in MeOH (2.4 M). Stir the mixture at reflux 24 hours. Follow the reaction by TLC (Hexane/EtOAc 4:1). Quench the crude with water, remove the MeOH in vacuo, and extract the aqueous layer with EtOAc. Separate the organic layer, dry with MgSO$_4$, and concentrate in vacuum. Purify the crude by Biotage (Hexane/EtOAc 4:1 and 2:1) to obtain a compound of formula E of scheme 5.

Add TFA (excess) to a solution of compound of formula E of scheme 5 (1.0 mmol) in CH$_2$Cl$_2$ (5 ml) and stir the mixture at room temperature overnight. Follow the reaction by TLC (Hexane/EtOAc 1:1). Remove the solvent and residual TFA in vacuum. Dissolve the residue in DCM and wash with a saturated solution of NaHCO$_3$. Dry the organic layer with MgSO$_4$ and concentrate in vacuum. Obtain the compound of formula F of scheme 5 as a pure solid.

Add powdered KOH (2.2 mmol), R—I (Br)(2.0 mmol) and Bu$_4$NBr (0.2 mmol) to a solution of the corresponding triazole derivate compound of formula E of scheme 5 (1.0 mmol) in THF (5 mL/mmol) and stir the mixture at room temperature overnight. Follow the reaction by TLC (hexane/EtOAc 4:1). Quench the crude with water and add EtOAc. Extract the aqueous layer with EtOAc (2×), separate the organic layer, dry with MgSO$_4$, and concentrate in vacuum. Purify the crude by Biotage (Hexane/EtOAc 7:1 and 4:1) to obtain compound of formula G of scheme 5 as a white solid.

Add TFA (excess) to a solution of compound of formula G of scheme 5 (1.0 mmol) in CH$_2$Cl$_2$ (5 ml) and stir the mixture at room temperature- overnight. Follow the reaction by TLC (Hexane/EtOAc 1:1). Remove the solvent and residual TFA in vacuum. Dissolve the residue in DCM and wash with a saturated solution of NaHCO$_3$. Dry the organic layer with MgSO$_4$ and concentrate in vacuum. Obtain compound of formula H of scheme 5 as a solid.

Synthesis of Example 54

Preparation 15

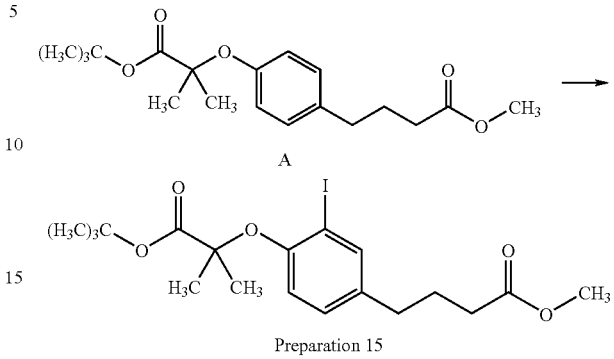

A

Preparation 15

Add I$_2$ (18.2 g, 71.4 mmol), and AgSO$_4$ (22.2 g, 71.4 mmol) to a solution of the corresponding triazole derivate (compound A above)(20 g, 64.4 mmol) in EtOH (65 mL) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with MgSO$_4$, and concentrate in vacuum. Purify the crude by Biotage (Hexane/EtOAc 9:1) to obtain preparation 15 as a white solid (m=15.8 g, Yield 56%).

Preparation 16

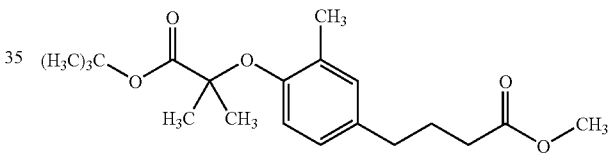

Add MeB(OH)$_2$ (3.48 g, 58.2 mmol), CsF (13.8 g, 91.0 mmol) and PdCl$_2$(dppf) (4.75 g, 5.82 mmol) to a solution of preparation 15 (15.8 g, 36.4 mmol) in anhydrous Dioxane (40 mL4) under N$_2$ and stir the mixture to 80° C. overnight. Follow the reaction by LC/MS. Cool and then filter the reaction through celite and remove the solvent under vacuum. Purify the crude by flash chromatography (Hexane/EtOAc 19:1 mixtures) to obtain 7.75 g (66% yield) of preparation 16 as a white solid.

Preparation 17

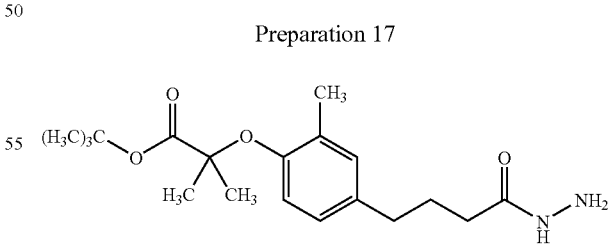

Dissolve preparation 16 (7.75 g, 24.04 mmol) in EtOH (50 mL). Then, add hydrazine monohydrate (4.66 mL, 96.2 mmol). Stir the mixture at room temperature overnight. Follow the reaction by TLC (hexane/EtOAc 9:1). Remove the solvent under vacuum. Dissolve the residue in EtOAc and wash with water. Dry the organic layer and concentrate. Preparation 17 is used without further purification.

Preparation 18

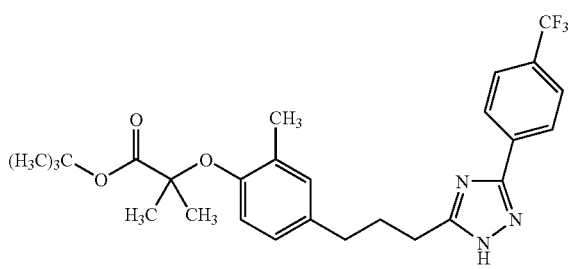

Add 4-(trifluoromethyl)benzonitrile (8.2 g, 48.08 mmol) and potassium tert-butoxide (1.62 g, 14.42 mmol) to a solution of preparation 17 (24.04 mmol) in EtOH (50 mL) and stir the mixture at reflux for 48 hours. Follow the reaction by TLC (Hexane/EtOAc 4:1). Quench the crude with water and remove the MeOH in vacuo and extract the aqueous layer with EtOAc. Separate the organic layer, dry with $MgSO_4$, and concentrate in vacuum. Purify the crude by flash chromatography (Hexane/EtOAc 4:1 and 2:1) to obtain 2.5 g (22% yield) of preparation 18.

Preparation 19

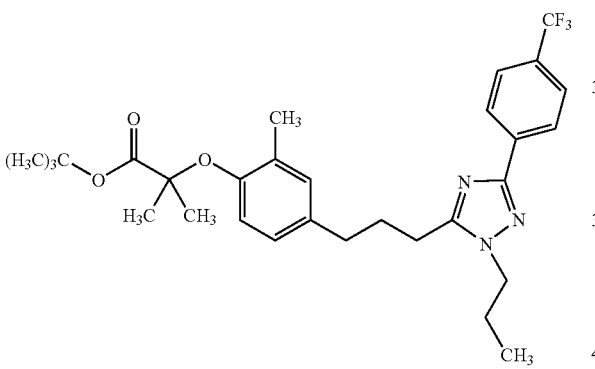

Add powdered KOH (0.065 g, 1.16 mmol), PrI (0.10 mL, 1.04 mmol) and $Bu_4NBr$ (0.033 g, 0.10 mmol) to a solution of preparation 18 (0.25 g, 0.52 mmol) in THF (5 mL) and stir the mixture at room temperature overnight. Follow the reaction by TLC (hexane/EtOAc 4:1). Quench the crude with water and add EtOAc. Extract the aqueous layer with EtOAc (2×). Separate the organic layer, dry with $MgSO_4$, and concentrate in vacuo. Purify the crude by flash chromatography (Hexane/EtOAc 9:1) to obtain 0.13 g (48% yield) of preparation 19.

EXAMPLE 54

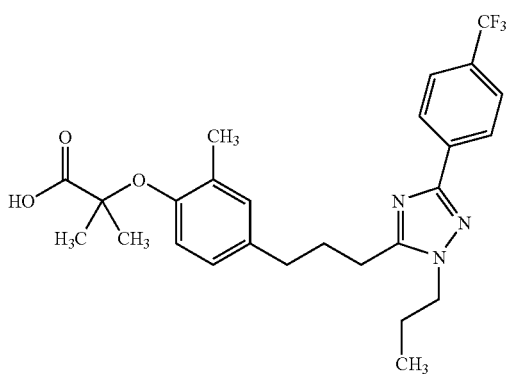

Add TFA (excess) to a solution of preparation 19 (0.09 g, 0.17 mmol) in $CH_2Cl_2$ (5 ml) and stir the mixture at room temperature overnight. Follow the reaction by TLC (Hexane/EtOAc 1:1). Remove the solvent and residual TFA in vacuum. Dissolve the residue is in DCM and wash with a saturated solution of $NaHCO_3$. Dry the organic layer with $MgSO_4$ and concentrate in vacuum. Obtain example 54 as a solid, 0.06 g (72% yield).

Prepare Example 53 by a similar procedure for the preparation of example 54.

| Example | Structure | LC/MS [M + 1] |
|---|---|---|
| 53 | 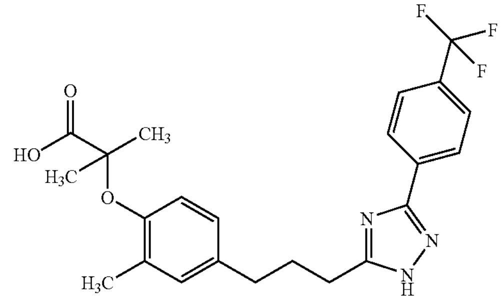 | 448.4 |

-continued
| Example | Structure | LC/MS [M + 1] |
|---------|-----------|---------------|
| 54 | 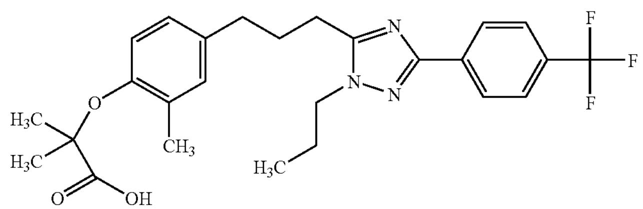 | 490.3 |
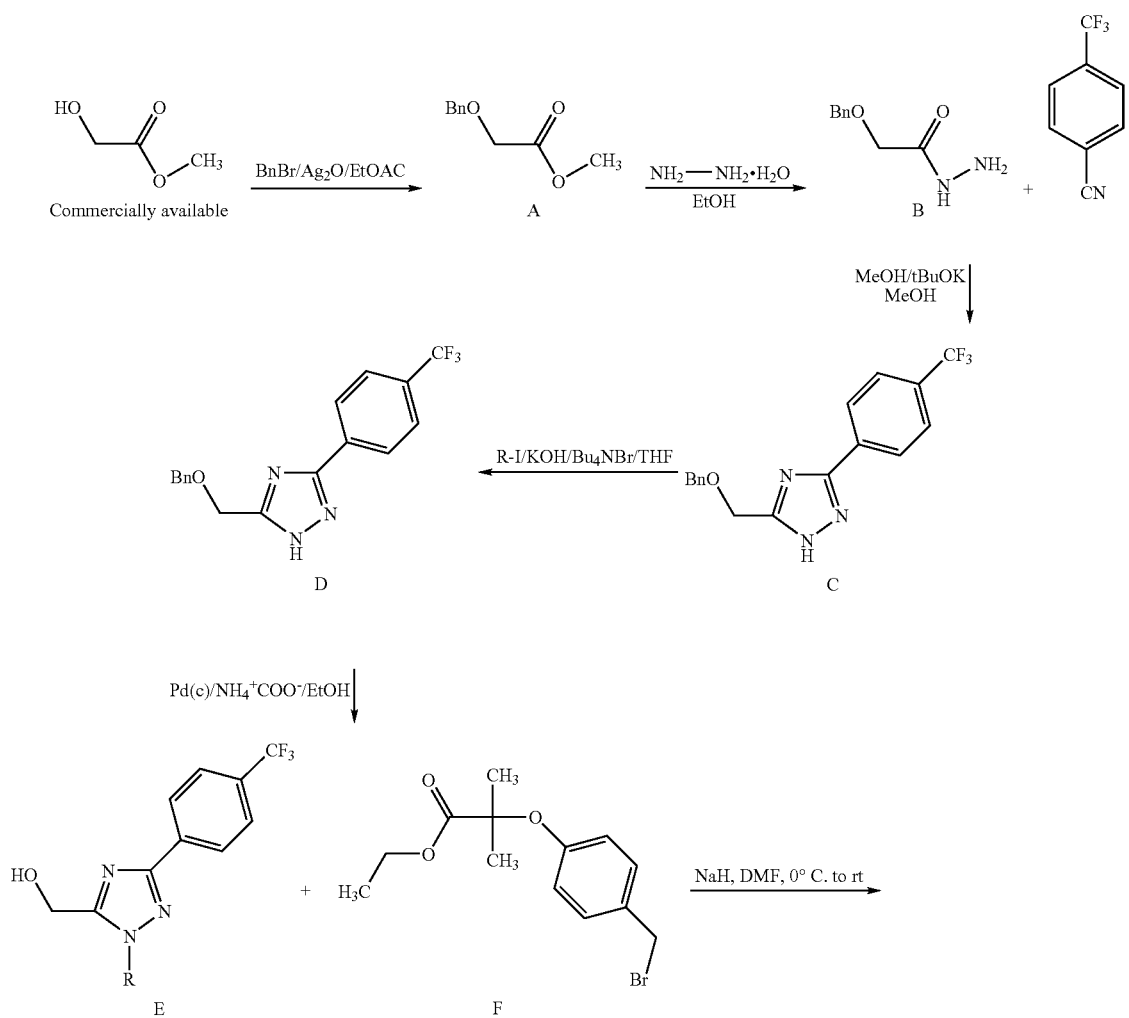
Scheme 6

-continued
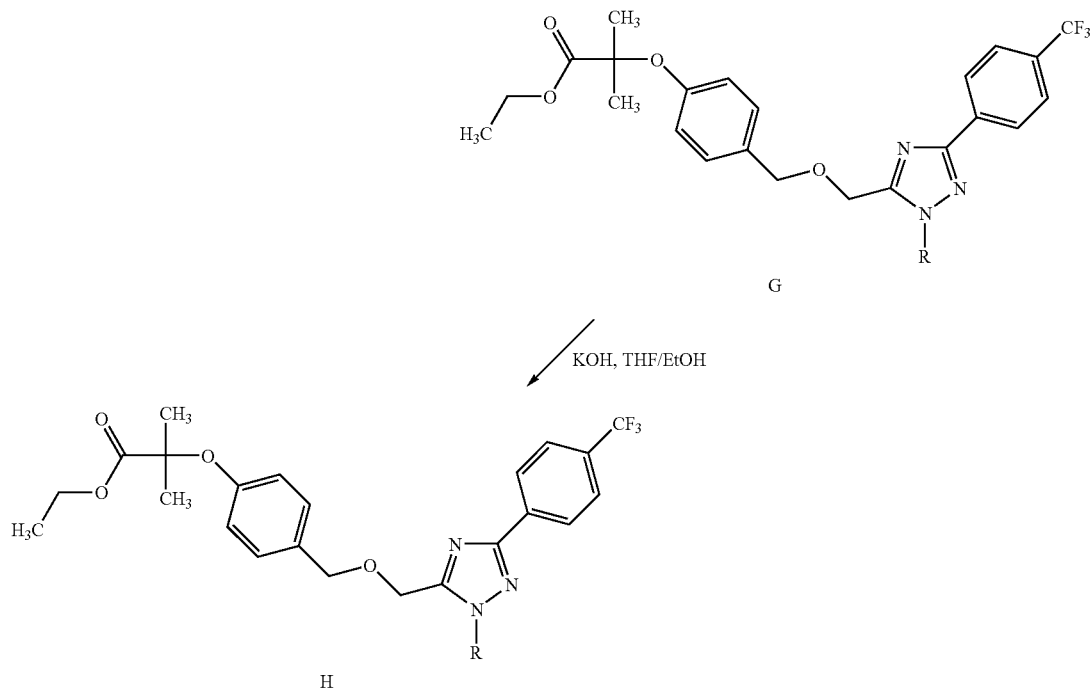
R in scheme 6 is R1 or R32.
Scheme 6a
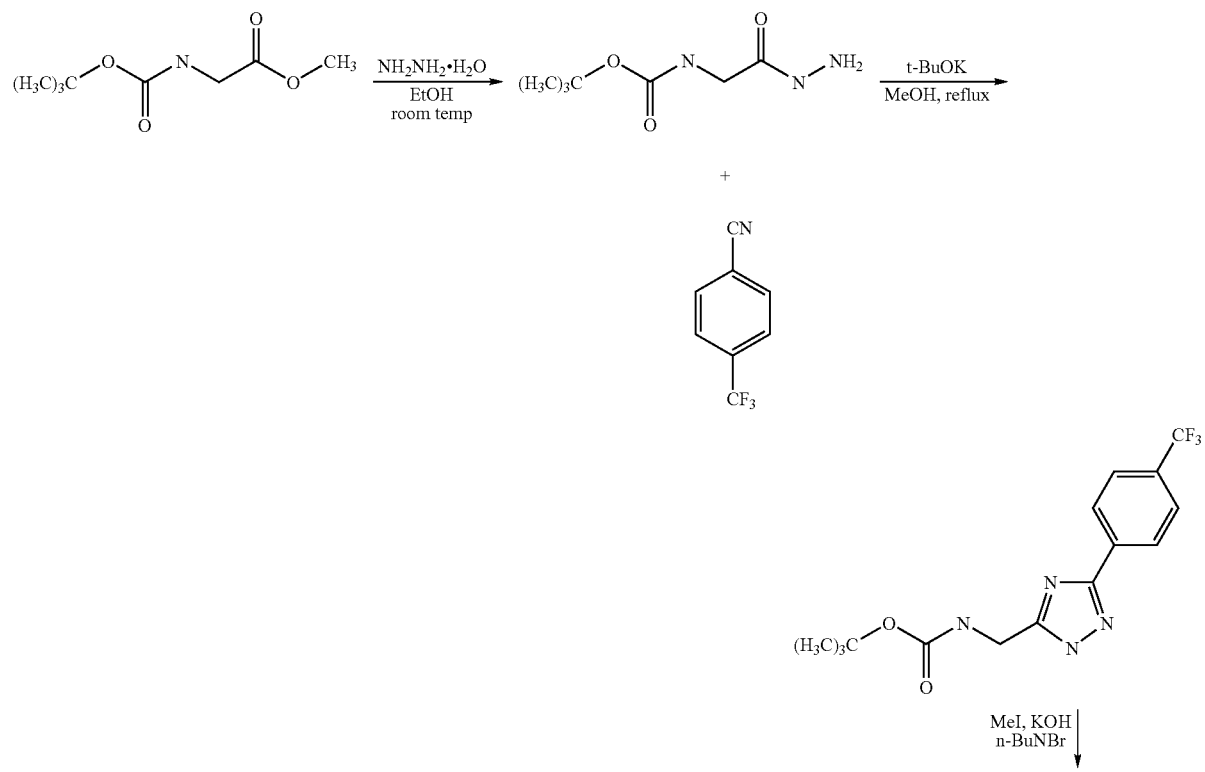

-continued
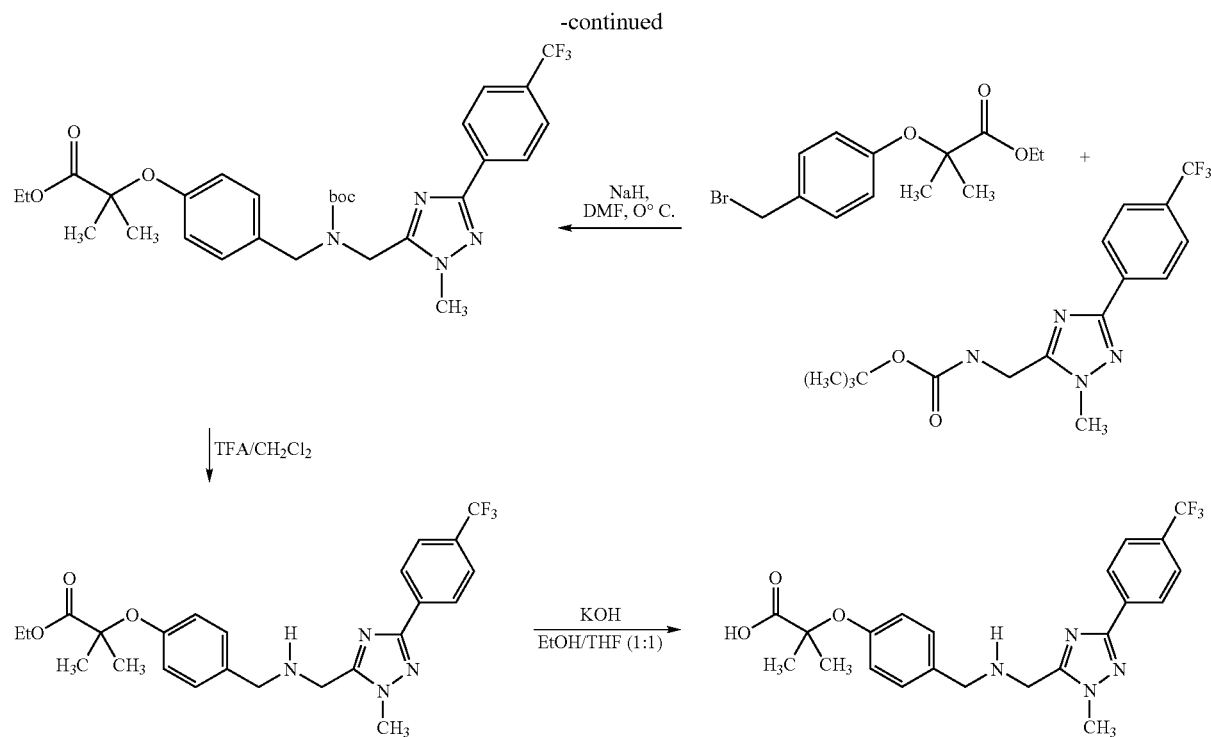
Scheme 6b
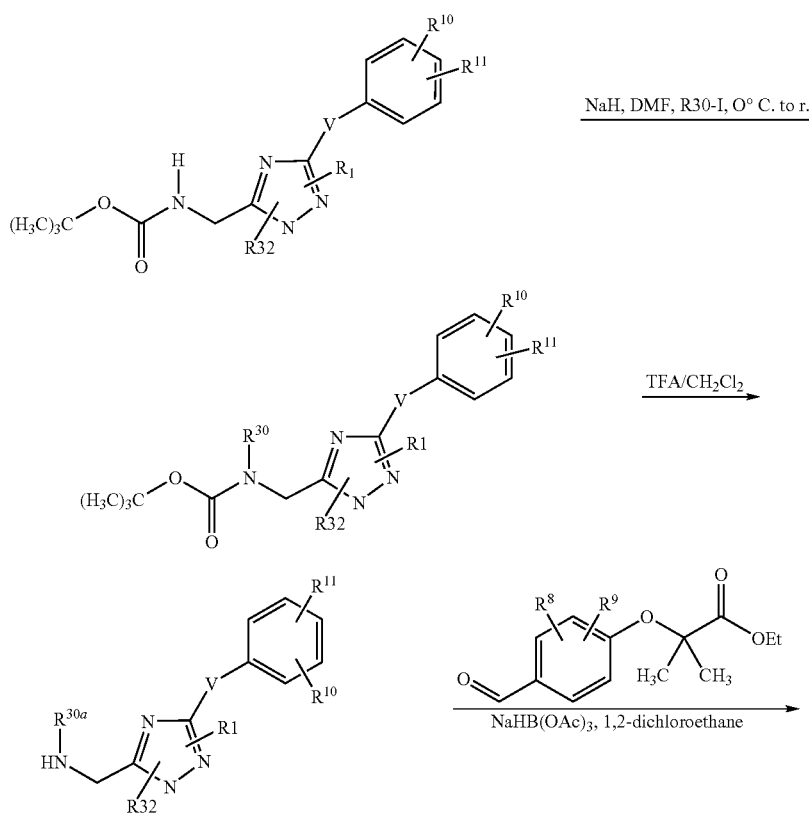

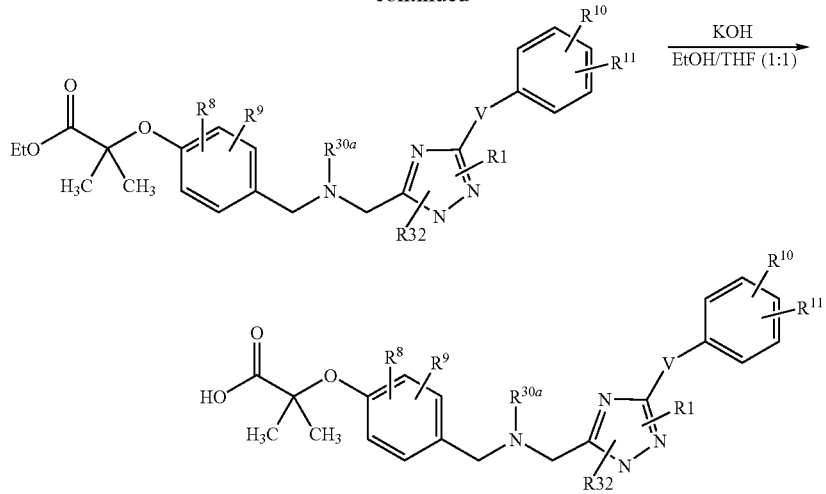

General Procedure for Scheme 6

Add BnBr (72.7 mL, 0.61 mol, 1.1 eq) and $Ag_2O$ (141.6 g, 0.61 mol, 1.1 eq) to a solution of methyl glycolate (50 g, 0.56 mol) in EtOAc (300 mL) and stir the mixture to reflux overnight. Follow the reaction by TLC (Hexane/EtOAC 1:1). Filter the reaction through celite and remove the solvent under vacuum. Pass adsorb the oil onto flash silica and place on top of a pad of flash silica (500 g) and elute with 20% ethyl acetate/hexane to give 75.8 g (75% yield) of compound A of scheme 6.

Dissolve the benzyl derivate compound of formula A of scheme 6 (1.0 mmol) in EtoH (0.8 M) and then add hydrazine monohydrate (3.0 mmol). Stir the mixture at room temperature overnight. Follow the reaction by TLC (Hexane/EtOAc 4:1). Remove the solvent under vacuum. Dissolve the residue in EtOAc and wash with water. Dry the organic layer and concentrate and use the crude without further purification. Add 4-(trifluoromethyl)benzonitrile (2.0 mol) and potassium tert-butoxide (0.6 mmol) to a solution of acylhydrazine compound of formula B of scheme 6 (1.0 mmol) in MeOH (2.4 M) and stir the mixture at reflux for 24 hours. Follow the reaction by TLC (Hexane/EtOAc 4:1). Quench the crude with water, remove the MeOH in vacuum, and extract the aqueous layer with EtOAc. Separate the organic layer, dry with $MgSO_4$, and concentrate in vacuum. Purify the crude by Biotage (Hexane/EtOAc 4:1) and obtain the compound C of scheme 6.

R=Me or $MeOCH_2CH_2$

Triazole alkylation: Add powdered KOH (2.2 mmol), R—I (Br) (2.0 mmol) and $Bu_4NBr$ (0.2 mmol) to a solution of the corresponding triazole compound (C) of scheme 6 (1.0 mmol) in THF (5 mL/mmol) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with $MgSO_4$, and concentrate in vacuum. Purify the crude by Biotage (Hexane/EtOAc 4:1) to obtain compound of formula D of scheme 6.

Add Pd (C) (10-20% in weight) and $NH_4^+COO^-$ (10-20 mmol) to a solution of triazole compound of formula D of scheme 6 (1.0 mmol) in EtOH (5 mL/mmol) and stir the mixture at 80° C. overnight. Follow the reaction by TLC. Filter the reaction through celite and remove the solvent under vacuum. Purify the crude by Biotage (Hexane/EtOAc 1:1) to obtain compound of formula E of scheme 6.

Add NaH (2.1 mmol, 60%) to a solution of triazole derivate compound of formula E of scheme 6 (1.0 mmol) in anhydrous DMF (10 mL) at 0° C., stir the mixture at room temperature for 15 minutes, cool to 0° C., and add the benzyl bromide (compound F of scheme 6) (1.5 mmol) in anhydrous DMF (5 mL). Stir the reaction at room temperature for 30 min, add MeOH, and then add water. Remove the MeOH in vacuum and extract the aqueous layer with EtOAc. Wash the organic layer with water and brine, dry over $MgSO_4$, filter, and concentrate under reduced pressure. Purify the crude by Biotage (Hexane/EtOAc 4:1) to obtain compound of formula G of scheme 6.

Add 2 N KOH solution (10 mmol) to a solution of triazole derivate compound of formula G of scheme 6 (1.0 mmol) in EtOH/THF mixture (1:1) (10 mL/mmol) and stir the mixture at room temperature overnight. Follow the reaction by TLC. Remove the solvent under vacuum and then, add water and EtOAc. Add 1N HCl solution until pH 5-7. Extract the mixture and wash the organic layer with water, separate, dry with $MgSO_4$, and concentrate in vacuum. Obtain the products of compound of formula H of scheme 6 as white solids.

SYNTHESIS OF EXAMPLE 55

Preparation 19

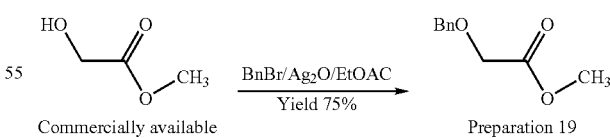

Add BnBr (72.7 mL, 0.61 mol, 1.1 eq) and $Ag_2O$ (141.6 g, 0.61 mol, 1.1 eq) to a solution of methyl glycolate (50 g, 0.56 mol) in EtOAc (300 mL) and stir the mixture to reflux overnight. Follow the reaction by TLC (Hexane/EtOAC 1:1). Filter the reaction through celite and remove the solvent under vacuum. The oil is passed adsorbed onto flash silica. Place on top of a pad of flash silica (500 g) and elute with 20% ethyl acetate/hexane to give 75.8 g (75% yield) of preparation 19 as a colorless oil.

Preparation 20

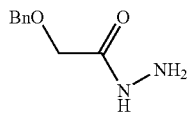

Dissolve preparation 19 (7.5 g, 41.6 mmol) in EtOH (100 mL). Then, add hydrazine monohydrate (6.05 mL, 124.9 mmol) and stir the mixture at room temperature overnight. Follow the reaction by TLC (hexane/EtOAc 4:1). Remove the solvent under vacuum. Dissolve the residue in EtOAc and wash with water. Dry the organic layer and concentrate. Use preparation 20 without further purification.

Preparation 21

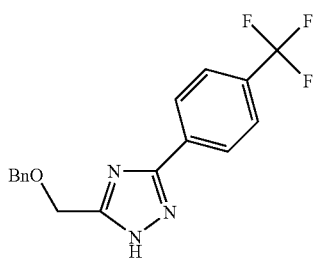

Add 4-(trifluoromethyl)benzonitrile (14.2 g, 83.2 mmol) and potassium tert-butoxide (2.8 g, 25 mmol) to a solution of preparation 20 in MeOH (100 mL) and stir the mixture at reflux for 24 hours. Follow the reaction by TLC (Hexane/EtOAc 4:1). Quench the crude with water, remove the MeOH in vacuum and extract the aqueous layer with EtOAc. Separate the organic layer, dry with $MgSO_4$, and concentrate in vacuum. Purify the crude by flash chromatography (Hexane/EtOAc 4:1) to obtain 11.2 g (81% yield) of preparation 21 as a white solid.

Preparation 22

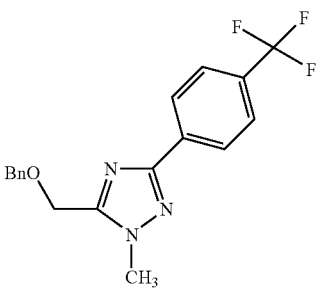

Add powdered KOH (0.27 g, 4.8 mmol), MeI (0.28 mL, 4.5 mmol) and $Bu_4NBr$ (0.09 g, 0.3 mmol) to a solution of preparation 21 (1.0 g, 3.0 mmol) in THF (15 mL) and stir the mixture at room temperature overnight. Follow the reaction by TLC (Hexane/EtOAc 4:1). Quench the crude with water and add EtOAc. Extract the aqueous layer with EtOAc (2×). Separate the organic layer, dry with $MgSO_4$, and concentrate in vacuum. Purify the crude by Biotage (Hexane/EtOAc 4:1) to obtain preparation 22 (1.04 g).

Preparation 23

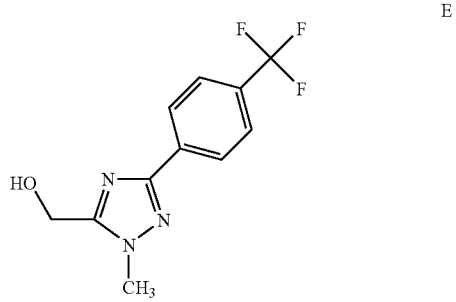

Add Pd (C) (10-20% in weight) and $NH_4^+COO^-$ (1.89 g, 30 mmol) to a solution of preparation 22 (1.04 g, 3.0 mmol) in EtOH (15 mL) and stir the mixture at 80° C. overnight. Follow the reaction by TLC. Filter the reaction through celite and remove the solvent under vacuum. Purify the crude by Biotage (Hexane/EtOAc 1:1) to obtain preparation 23 (0.59 g, 76% yield).

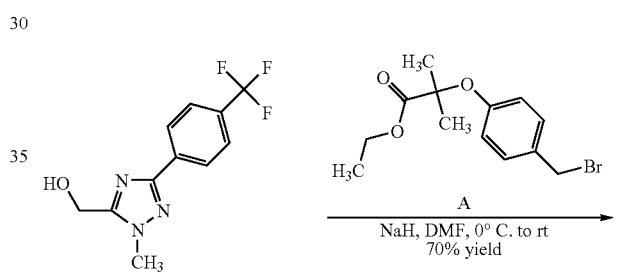

Preparation 23

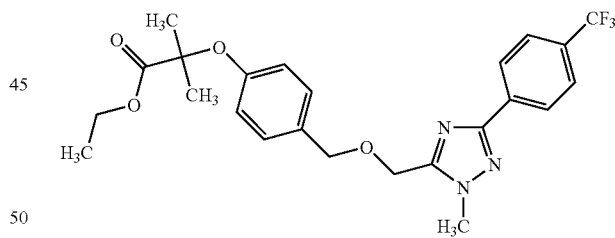

Preparation 24

Add NaH (0.091 g, 2.29 mmol, 60%) to a solution of preparation 23 (0.28 g, 1.09 mmol) in anhydrous DMF (10 mL) at 0° C. and stir the mixture at room temperature for 15 minutes. Cool again at 0° C. and add the benzyl bromide compound A (0.68 g, 1.63 mmol) in anhydrous DMF (5 mL) and stir the reaction at room temperature for 30 min. Add MeOH and then add water. Remove the MeOH in vacuum and extract the aqueous layer with EtOAc. Wash the organic layer with water and brine, dry over $MgSO_4$, filter and concentrate under reduced pressure. Purify the crude by Biotage (Hexane/EtOAc 4:1) to obtain preparation 24 as white solids (0.39 g, 70% yield).

EXAMPLE 55

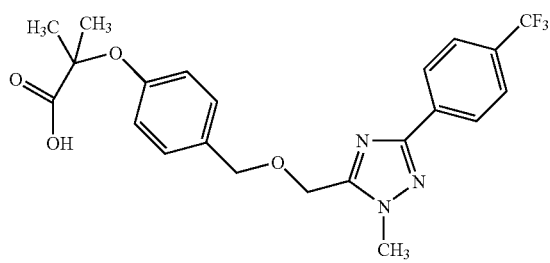

Add 2N KOH solution (1.05 mL, 2.1 mmol) to a solution of preparation 24 (0.1 g, 0.21 mmol) in EtOH/THF mixture (1:1) (2 mL) and stir the mixture at room temperature overnight. Follow the reaction by TLC. Remove the solvent under vacuum and then, add water and EtOAc. Add 1N HCl until pH 5-7. Extract the mixture and wash the organic layer with water, separate, dry with $MgSO_4$, and concentrate in vacuum. Example 55 is obtained as white solids (65 mg, 69% yield).

Prepare Example 56 by a similar procedure for the preparation of example 55.

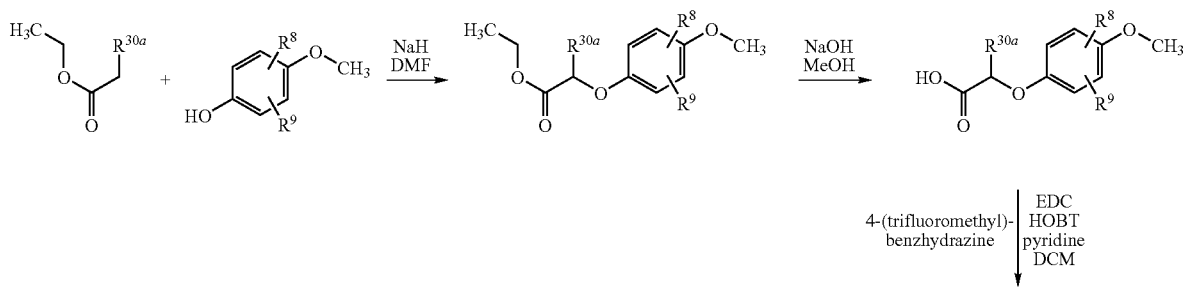

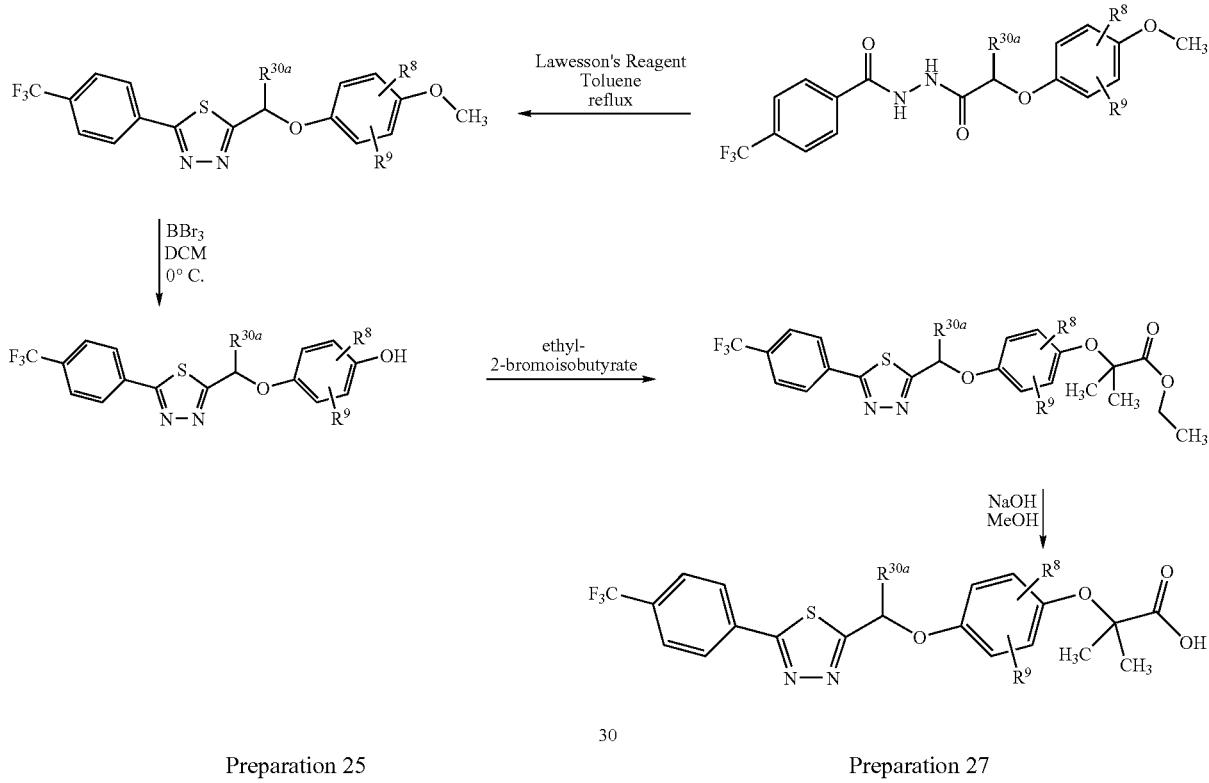

Preparation 25

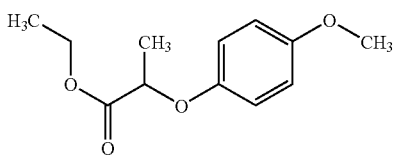

Slurry sodium hydride (369 mg, 9.2 mmol) in DMF (25 ml) at 0° C., and then add 4-methoxyphenol (1.15 g, 9.2 mmol) in one portion. After stirring for 30 min., add ethyl 2-bromopropionate (1.391 g, 7.7 mmol) in one portion and allow the reaction to warm to room temperature overnight. Quench the reaction with 1 N HCl and extract with ethyl acetate. Combine the organic layers, dry over $MgSO_4$, and evaporate. Purify the residue via silica gel chromatography (30% ethyl acetate in hexanes) to give the 983.1 mg of preparation 25 as a thick, clear oil (57.2%). MS=225 $(M+H^+)$; 242 $(M+NH_4^+)$.

Preparation 26

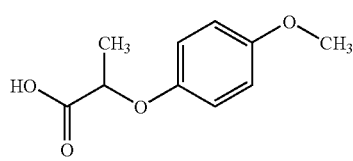

Dissolve preparation 26 (983 mg, 4.4 mmol) in methanol (10 ml) and add to this 1N NaOH (10 ml). Stir at room temperature for 12 hrs. Then, evaporate the solvent, dissolve the residue in 1N HCl (20 ml), and extract with ethyl acetate. Combine the organics, dry over $MgSO_4$, and evaporate. Use this crude product (767.5 mg, 89%) without further purification. MS=195 $(M-H^-)$; 214 $(M+NH_4^+)$.

Preparation 27

Dissolve preparation 26 (100 mg, 0.5 mmol) in dichloromethane (10 ml) and add EDC (117 mg, 0.6 mmol) followed by HOBT (83 mg, 0.6 mmol) and stir for 5 min. Then, add 4-(trifluoromethyl)benzhydrazine (104 mg, 0.5 mmol) in one portion followed by pyridine (0.124 ml, 1.5 mmol) and stir at room temperature overnight. After this time, wash the reaction with saturated sodium bicarbonate solution and 1N HCl. Dry the organics over $MgSO_4$ and evaporate. Purify the residue via silica gel chromatography (50% ethyl acetate in hexanes) to give the 127.8 mg of preparation 27 as white solid (65.6%). MS=383 $(M+H^+)$; 381 $(M-H^-)$.

Preparation 28

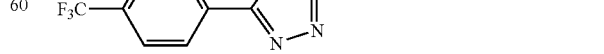

Dissolve the preparation 27 (127 mg, 0.33 mmol) in toluene (5 ml). To this add Lawesson's reagent (134 mg, 0.33 mmol) and the heat the reaction to reflux for 2 hrs. After this time, cool the reaction and dilute with 20 ml of ethyl acetate.

Wash with saturated bicarbonate solution and dry the organics over MgSO₄ and evaporate. Purify. the residue via silica gel chromatography (15% ethyl acetate in hexanes) to give the 103.8 mg of preparation 28 as a white solid (82.2%). MS=381 (M+H⁺).

Preparation 29

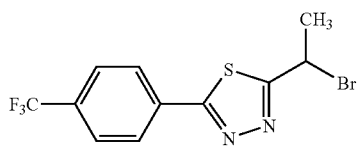

Dissolve preparation 28 (100 mg, 0.26 mmol) in dichloromethane (5 ml). This is then cooled to 0° C. and add boron tribromide (0.788 ml, 0.79 mmol). After 2 hrs, quench the reaction with saturated bicarb and extract with 20 ml of ethyl acetate. The organics are dried over MgSO₄ and evaporated. This gave 87.2 mg of preparation 29 as an off white solid (98.4%). MS=337 & 338 (M+H⁺).

Preparation 30

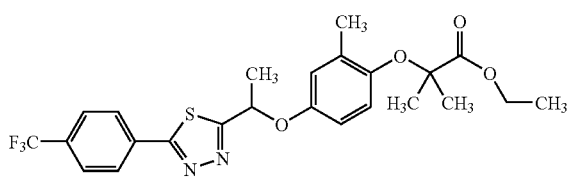

Dissolve 2-(4-hydroxy-2-methyl-phenoxy)-2-methyl-propionic acid ethyl ester (73.6 mg, 0.31 mmol) in DMF. To this add sodium hydride (12.4 mg, 0.31 mmol) and stir at room temperature for 5 min. After this time preparation 29 (87 mg, 0.26 mmol) is added in one portion and the reaction continued for 2 hrs. Quench the reaction with saturated ammonium chloride and extract with ethyl acetate. Dry the organics over MgSO₄ and evaporate. Purify the residue via silica gel chromatography (15% ethyl acetate in hexanes) to give the 59.7 mg of preparation 30 as a clear oil (46.8%). MS=495 (M+H⁺).

EXAMPLE 57

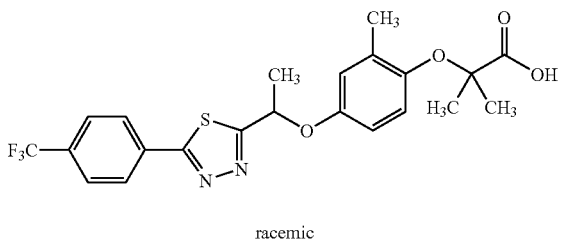

racemic

Dissolve preparation 30 (59 mg, 0.12 mmol) in methanol (2 ml). To this, add 1N NaOH solution (2 ml). After 12 hrs the reaction is brought to pH=6 with 1N HCl solution and extracted ethyl acetate. Dry the organics over MgSO₄ and evaporate. Purify the residue via silica gel chromatography (50% ethyl acetate in hexanes) then reverse phase HPLC (40-90% gradient @ 140 ml/min for 30 min on a 50×250 mm, mm, C18 Symmetry column) to give the 7.1 mg of example 57 as a white solid (12.7%). MS=467 (M+H⁺).

Scheme 8

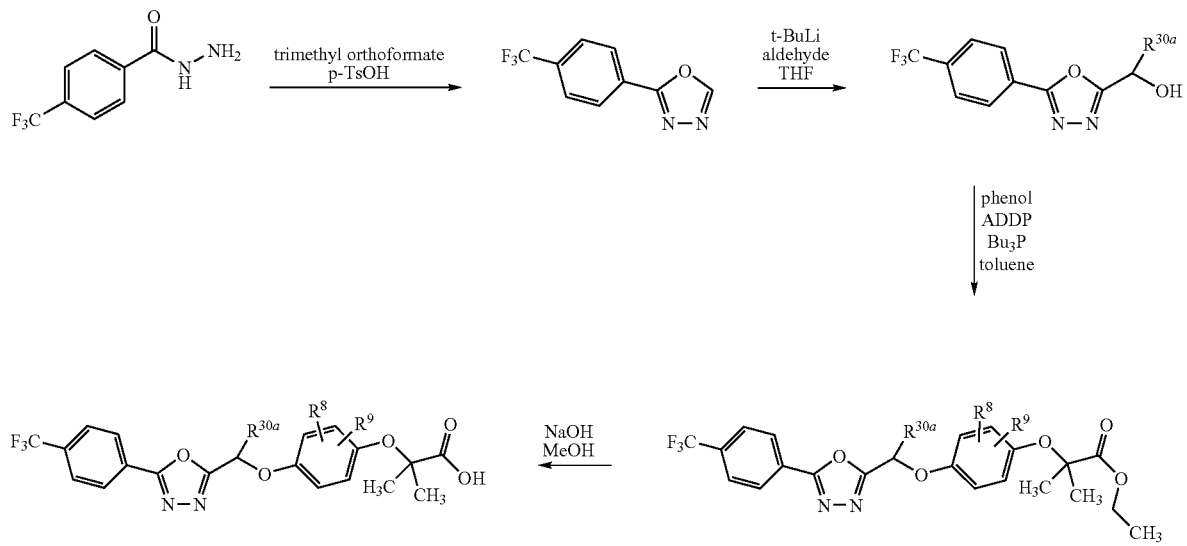

Preparation 31

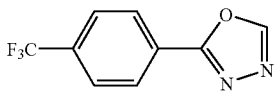

Place 4-(Trifluoromethyl)benzhydrazide (5 g, 24.5 mmol) in a round bottom flasked equipped with a short path reflux condenser. Add to this was trimethyl orthoformate (4 ml, 36.7 mmol) followed by p-toluene sulfonic acid (46.6 mmg, 0.24 mmol). Heat to 100° C. and distill off the methanol. After 2 hrs, no more methanol is collected the pressure of the system is lowered to 300 microns to remove the unused trimethyl orthoformate. Cool the residual solid and dissolve in ethyl acetate. Wash with saturated bicarbonate solution and combine the organics, dry over MgSO$_4$, and evaporate. Use the crude product (5.2 g, 99%) without further purification. MS=215 (M+H$^+$).

Preparation 32

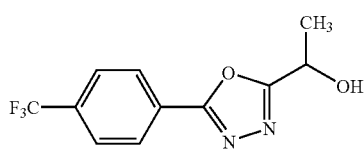

Dissolve preparation 31 (500 mg, 2.3 mmol) in THF and cool to −78° C. To this, add t-BuLi (1.5 ml, 1.7 M soln) and stir for 30 min. After this time, add acetaldehyde (0.157 ml, 2.8 mmol) and allow the reaction to slowly warm to room temperature over 6 hrs. After this time, quench the reaction with saturated ammonium chloride solution and then extract with ethyl acetate. Dry the combined organics over MgSO$_4$ and evaporate. Purify the residue via silica gel chromatography (20% ethyl acetate in hexanes) to give 24 mg of preparation 32 as white solid (3.9%).

Preparation 33

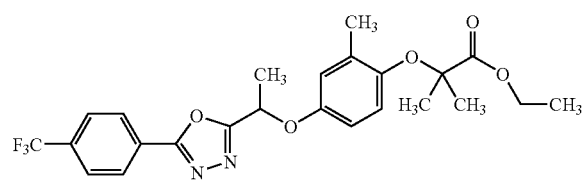

Dissolve preparation 32 (24 mg, 0.09 mmol) in toluene (2 ml) and add 2-(4-hydroxy-2-methyl-phenoxy)-2-methyl-propionic acid ethyl ester (26.5 mg, 0.11 mmol). Bubble nitrogen into this mixture for 15 min. After this time, add ADDP (35.1 mg, 0.135 mmol) followed by Bu3P (0.034 ml, 0.135 mmol) and stir the reaction for 18 hrs at room temperature. After this time, dilute the reaction in 20 ml of ethyl acetate and wash with brine. Dry the organics over MgSO4 and evaporate. Purify the residue via silica gel chromatography (20% ethyl acetate in hexanes) to give 24.4 mg of preparation 33 as a white solid (54.9%). MS=479 (M+H$^+$).

EXAMPLE 58

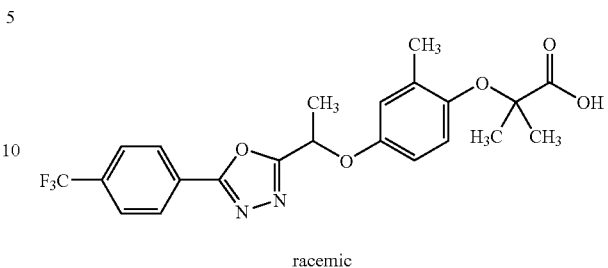

racemic

Dissolve the preparation 33 (59 mg, 0.12 mmol) in methanol (2 ml). To this, add 1N NaOH solution (2 ml). After 12 hrs the reaction is brought to pH=6 with 1N HCl solution and extracted ethyl acetate. Dry the organics over MgSO$_4$ and evaporate. Purify the residue via silica gel chromatography (50% ethyl acetate in hexanes) then reverse phase HPLC (40-90% gradient @ 140 ml/min for 30 min on a 50×250 mm, mm, C18 Symmetry column) to give the 8.6 mg of example 58 as a white solid (9.5%). MS=451 (M+H$^+$).

EXAMPLE 59

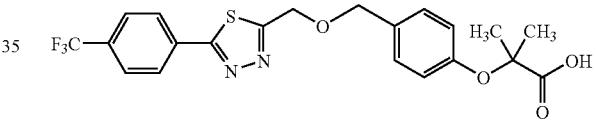

Example 59 can be made by one of ordinary skill in the art using the same procedure as example 57 using 2-(4-hydroxymethyl-phenoxy)-2-methyl-propionic acid ethyl ester (162 mg, 0.67 mmol) as the nucleophile and 2-bromomethyl-5-(4-trifluoromethyl-phenyl)-[1,3,4]thiadiazole (200 mg, 0.62 mmol) as the electrophile (as described in preparation 30) and then doing the saponification as described in example 57. After purification via silica gel chromatography (20% ethyl acetate in hexanes), 60.2 mg (21.5%) of example 59 is obtained as a thick oil. MS=451 (M−H$^-$).

EXAMPLE 60

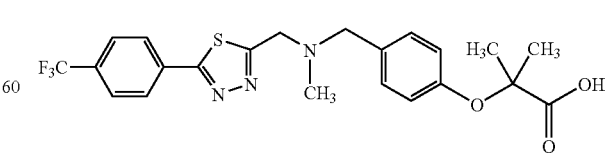

Example 60 can be made by one of ordinary skill in the art using the same procedure as example 57 using 2-Methyl-2-

(4-methylaminomethyl-phenoxy)-propionic acid ethyl ester (171 mg, 0.67 mmol) as the nucleophile and 2-bromomethyl-5-(4-trifluoromethyl-phenyl)-[1,3,4]thiadiazole (200 mg, 0.62 mmol) as the electrophile (as described in preparation 30) and then doing the saponification as described in example 57. After purification via silica gel chromatography (10% methanol in dichloromethane), 75.3 mg (26.3%) of example 60 is obtained as a thick oil. MS=464 (M−H⁻).

EXAMPLE 61

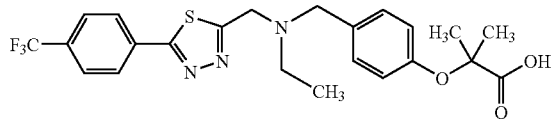

Example 61 can be made by one of ordinary skill in the art using the same procedure as example 57 using 2-(4-Ethylaminomethyl-phenoxy)-2-methyl-propionic acid ethyl ester (180.6 mg, 0.67 mmol) as the nucleophile and 2-bromomethyl-5-(4-trifluoromethyl-phenyl)-[1,3,4]thiadiazole (200 mg, 0.62 mmol) as the electrophile (as described in preparation 30) and then doing the saponification as described in example 57. After purification via silica gel chromatography (10% methanol in dichloromethane), 24.3 mg (8.3%) of example 61 is obtained as a thick oil. MS=478 (M−H⁻).

Preparation 34

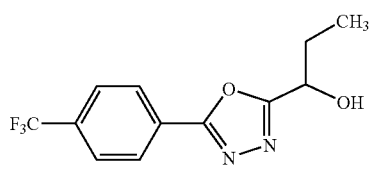

Dissolve preparation 31 (500 mg, 2.3 mmol) in THF and cool to −78° C. To this, add t-BuLi (1.5 ml, 1.7 M soln) and stir for 30 min. After this time, add propianaldehyde (0.202 ml, 2.8 mmol) and allow the reaction to slowly warm to room temperature over 6 hrs. After this time, quench the reaction with saturated ammonium chloride solution and then extract with ethyl acetate. Dry the combined organics over MgSO₄ and evaporate. Purify the residue via silica gel chromatography (20% ethyl acetate in hexanes) to give 99.8 mg of preparation 34 as white solid (15.7%).

Preparation 35

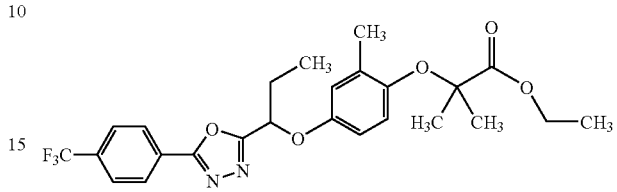

Dissolve preparation 34 (99 mg, 0.36 mnmol) in toluene (5 ml) and add 2-(4-hydroxy-2-methyl-phenoxy)-2-methyl-propionic acid ethyl ester (105 mg, 0.43 mmol). Bubble nitrogen into this mixture for 15 min. After this time, add ADDP (139 mg, 0.54 mmol) followed by Bu₃P (111.5 mg, 0.54 mmol) and stir the reaction for 18 hrs at room temperature. After this time, dilute the reaction in 20 ml of ethyl acetate and wash with brine. Dry the organics over MgSO4 and evaporate. Purify the residue via silica gel chromatography (20% ethyl acetate in hexanes) to give 63.0 mg of preparation 35 as a white solid (34.8%). MS=493 (M+H⁺).

EXAMPLE 62

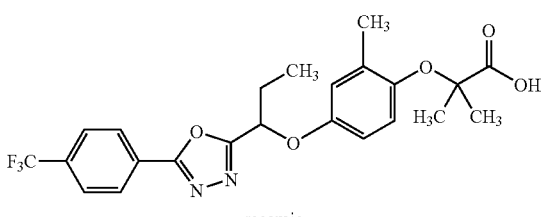

racemic

Racemic

Dissolve the preparation 35 (63 mg, 0.13 mmol) in methanol (2 ml). To this is then added 1N NaOH solution (2 ml). After 12 hrs the reaction is brought to pH=6 with 1N HCl solution and extracted ethyl acetate. The organics are dried over MgSO₄ and evaporated. Purify the residue via silica gel chromatography (50% ethyl acetate in hexanes) then reverse phase HPLC (40-90% gradient @ 140 ml/min for 30 min on a 50×250 mm, mm, C18 Symmetry column) to give the 9.7 mg of example 62 as a white solid (16.3%). MS=465 (M+H⁺).

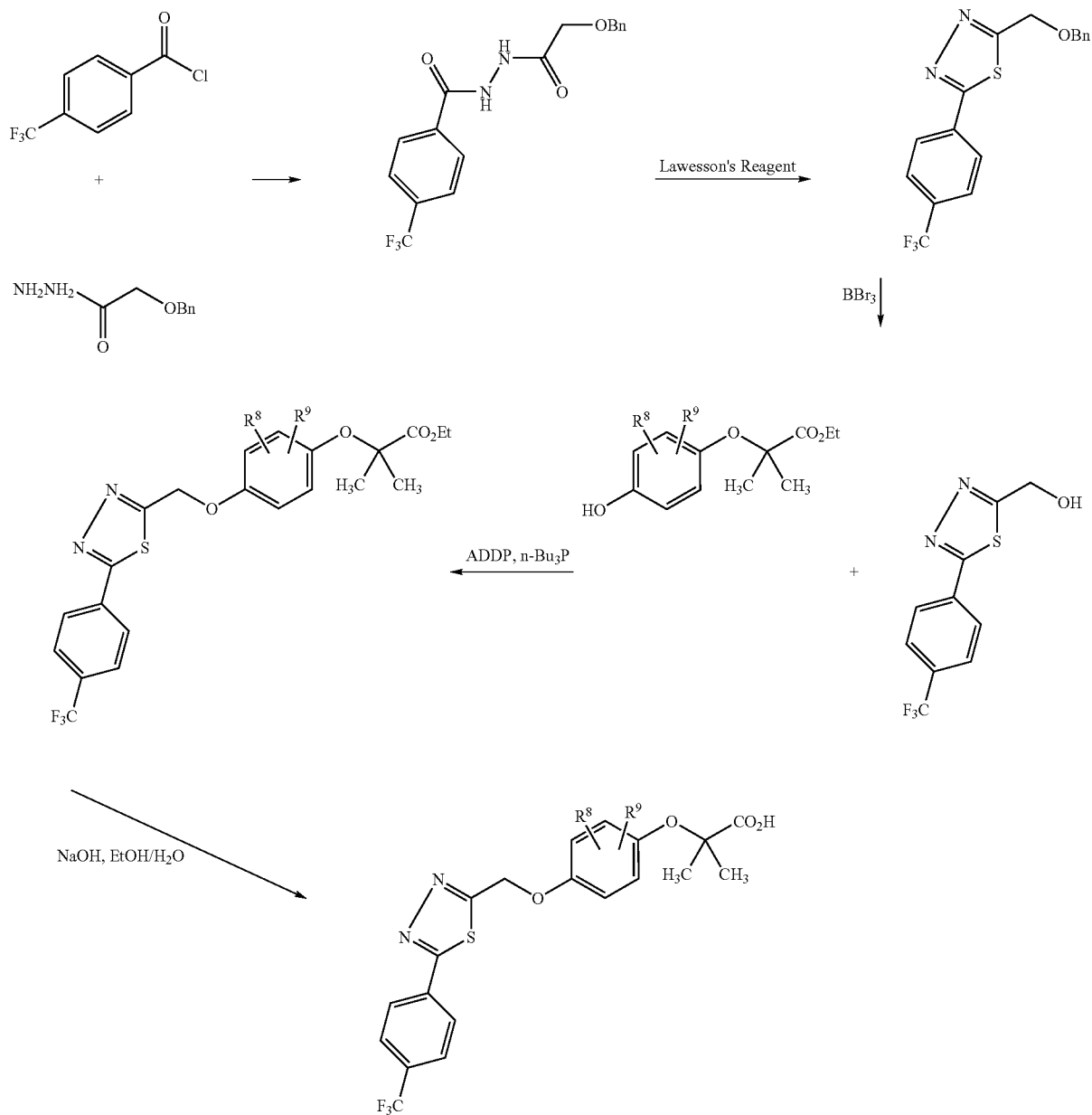
Preparation 36
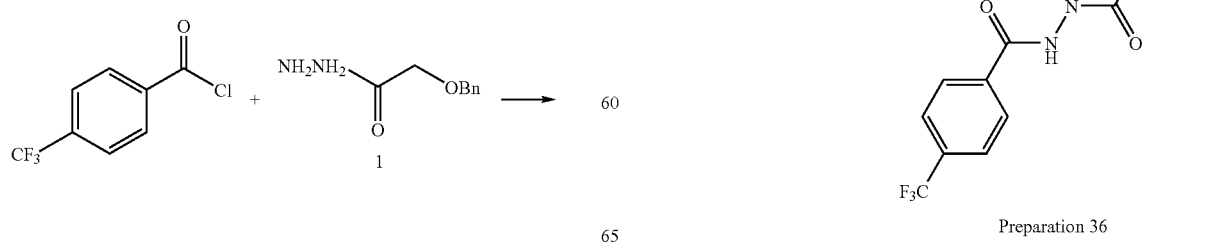
-continued
Preparation 36

Add p-trifluoromethyl benzoyl chloride (11.3 mL, 76 mmol) to a 0° C. solution of the acyl hydrazine (compound 1 above) (13.7 g, 76 mmol) in CH$_2$Cl$_2$ (200 mL) and pyridine (20 mL) over 15 min and stir the reaction for 30 min. Then, pour into 5 N HCl (200 mL). Extract the solution with Et$_2$O (250 mL) and EtOAc (250 mL). Wash the combined organic extracts with H$_2$O (200 mL) followed by brine (200 mL), dry over Na$_2$SO$_4$, filter, and concentrate. Titrate the crude semi-solid with 10% Et$_2$O/hexanes, precipitating out the desired Preparation 36 (23.4 g, 88%) as a white solid. $^1$H NMR (CDCl$_3$) δ 10.64 (s, 1 H), 10.07 (s, 1 H), 8.09 (m, 2 H), 7.93 (m, 2 H), 7.40 (m, 5 H), 4.64 (s, 2 H), 4.11 (s, 2 H).

Preparation 37

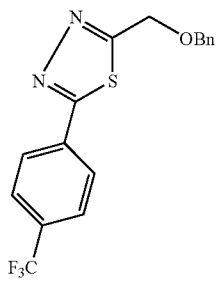

Heat a solution of Preparation 36 (12.0 g, 34.1 mmol) and Lawesson's reagent (16.5 g, 40.9 mmol) in toluene (200 mL) to reflux for 4 hr, then cool to room temperature and pour into H$_2$O (400 mL). Extract the mixture with Et$_2$O (200 mL) and EtOAc (400 mL). Wash the combined organic extracts with brine (250 mL), dry over Na$_2$SO$_4$, filter, and concentrate. Purification of the crude product by MPLC (0% to 10% to 15% to 20% EtOAc/hexanes gradient) affords Preparation 37 (11.2 g, 93%) as a clear oil. $^1$H NMR (CDCl$_3$) δ 8.10 (d, J=8.4 Hz, 2 H), 7.75 (d, J=8.4 Hz, 2 H), 7.37 (m, 5 H), 4.99 (s, 2 H), 4.70 (s, 2 H).

Preparation 38

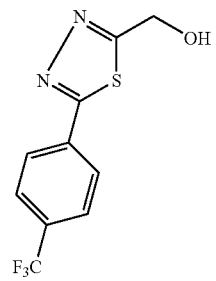

Add a solution of BBr$_3$ (42 mL, 1 M in CH$_2$Cl$_2$, 42 mmol) over 15 min. to a 0° C. solution of Preparation 37 (9.8 g, 27.9 mmol) in CH$_2$Cl$_2$ (120 mL). After an additional 15 min at 0° C., pour the contents into ½ satd. NaHCO$_3$ (500 mL). Extract the mixture with Et$_2$O (250 mL) and EtOAc (300 mL). Wash the combined organic extracts with brine (250 mL), dry over Na$_2$SO$_4$, filter, and concentrate to afford a white solid. Titrate the crude product with 10% Et2O/hexanes, precipitating out the desired Preparation 38 (7.0 g, >95%) as a white solid. $^1$H NMR (CDCl$_3$) δ 8.09 (d, J=8.4 Hx, 2 H), 7.60 (d, J=8.4 Hz, 2 H), 5.16 (s, 2 H), 2.40-2.60 (br s, 1 H).

Preparation 39

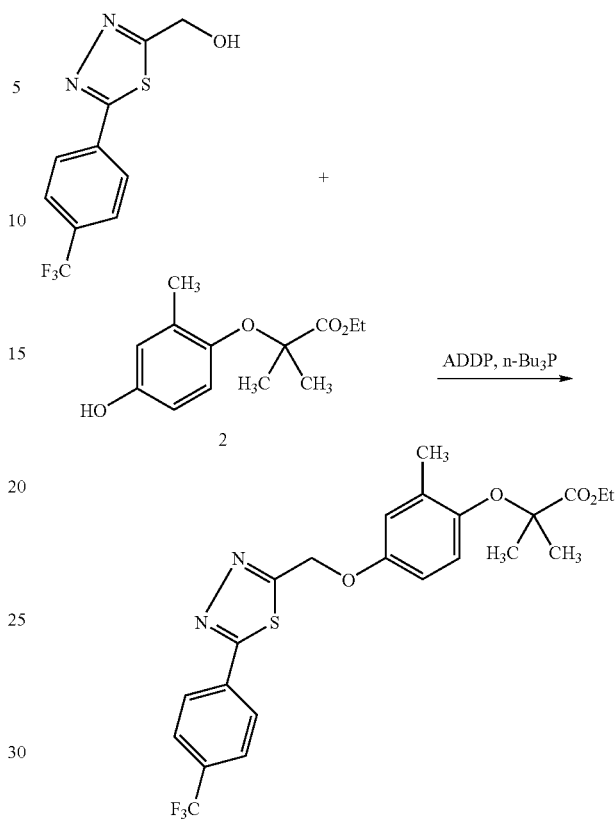

Bubble nitrogen gas through a solution of Preparation 38 (0.125 g, 0.48 mmol) and phenol compound 2 (0.119 g, 0.50 mmol) in toluene (5 mL) for 10 min. Cool the solution to 0° C. and add tri-n-butyl phosphine (0.180 mL, 0.72 mmol) followed by (1,1')-azodicarbonyl-dipiperidine (ADDP) (0.182 g, 0.72 mmol). After 5 min, allow the reaction to warm to room temperature and is stir for 16 hours. Then, pour the reaction mixture into ½ satd. NaHCO$_3$ (25 mL). Extract the mixture with Et$_2$O (25 mL) and EtOAc (25 mL). Wash the combined organic extracts with brine (25 mL), dry over Na$_2$SO$_4$, filter, and concentrate. Purification of the crude product by MPLC (0% to 5% to 8% to 12% EtOAc/hexanes) affords preparation 39 (0.138 g, x %) as a white foam. $^1$H NMR (CDCl$_3$) δ 8.11 (d, J=8.4 Hz, 2 H), 7.77 (d, J=8.4 Hz, 1 H), 6.72 (s, 1 H), 6.65 (m, 1 H), 6.56 (d, J=3.2 Hz, 1 H), 5.48 (s, 2 H), 4.27 (q, J=7.2 Hz, 2 H), 2.19 (s, 3 H), 1.55 (s, 6 H), 1.32 (t, J=7.2 Hz, 3 H).

EXAMPLE 63

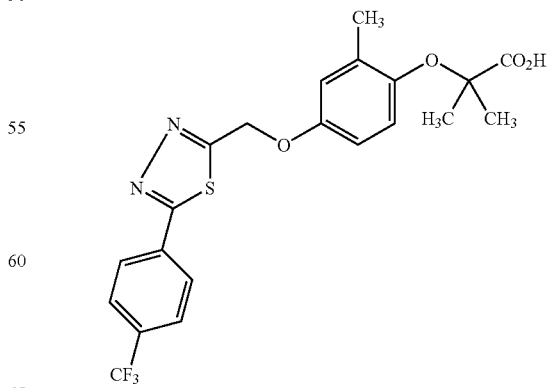

Heat a solution of Preparation 39 (0.138 g, 0.29 mmol) in EtOH (5 mL) and 2 N NaOH (1 mL) to 40° C. for 1 h. Pour the mixture into 1 N HCl (20 mL) and extract with Et$_2$O (20 mL) and EtOAC (2×20 mL). Wash the combined organic extracts with brine (25 mL), dry over Na$_2$SO$_4$, filter, and concentrate. Purification of the crude product by column chromatography (35% EtOAc/2% HOAc in hexanes) affords example 59 (0.102 g, 77%) as a white solid. LRMS 453.1 (M++H).

Preparation 40

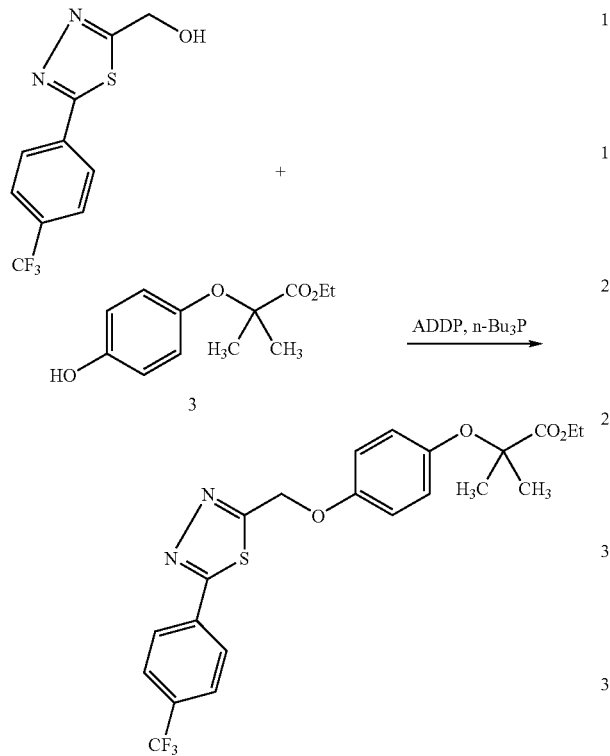

The reaction is run according to preparation 39. The reaction of Preparation 38 (0.125 g, 0.48 mmol) and phenol compound 3 (above) (0.112 g, 0.50 mmol) affords Preparation 40 (0.124 g, 55%) as a white foam. $^1$H NMR (CDCl$_3$) δ 8.08 (d, J=8.2 Hz, 2H), 7.74 (d, J=8.2 Hz, 2 H), 6.89 (m, 2 H), 6.75 (m, 2 H), 5.47 (s, 2 H), 4.23 (q, J=7.2 Hz, 2 H), 1.52 (s, 6 H), 1.27 (t, J=7.2 Hz, 3 H).

EXAMPLE 64

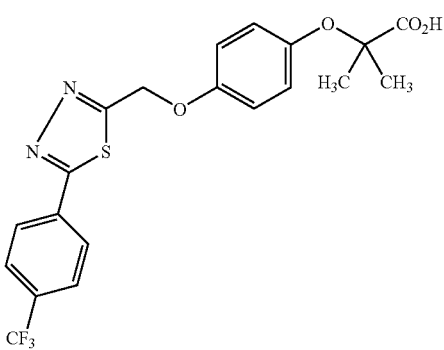

The reaction is run according to that for example 63. Hydrolysis of preparation 40 (0.124 g, 0.27 mmol) affords example 60 (0.082 g, 69%) as a white foam. LRMS 439.1 (M++H).

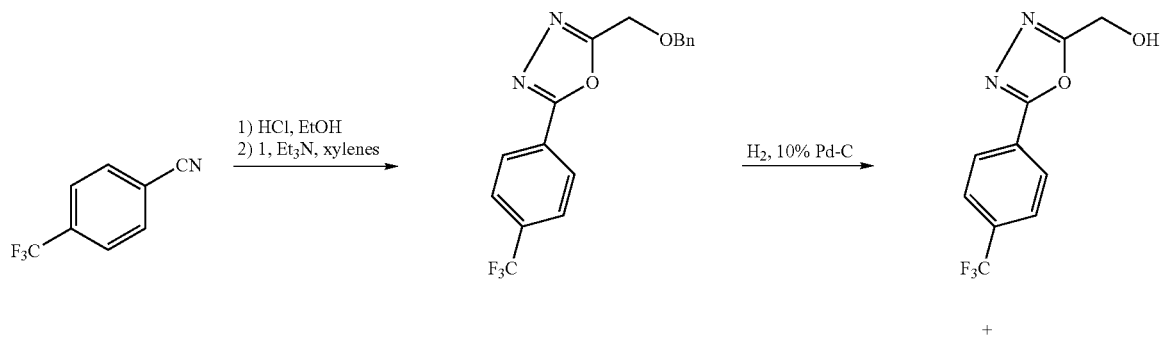

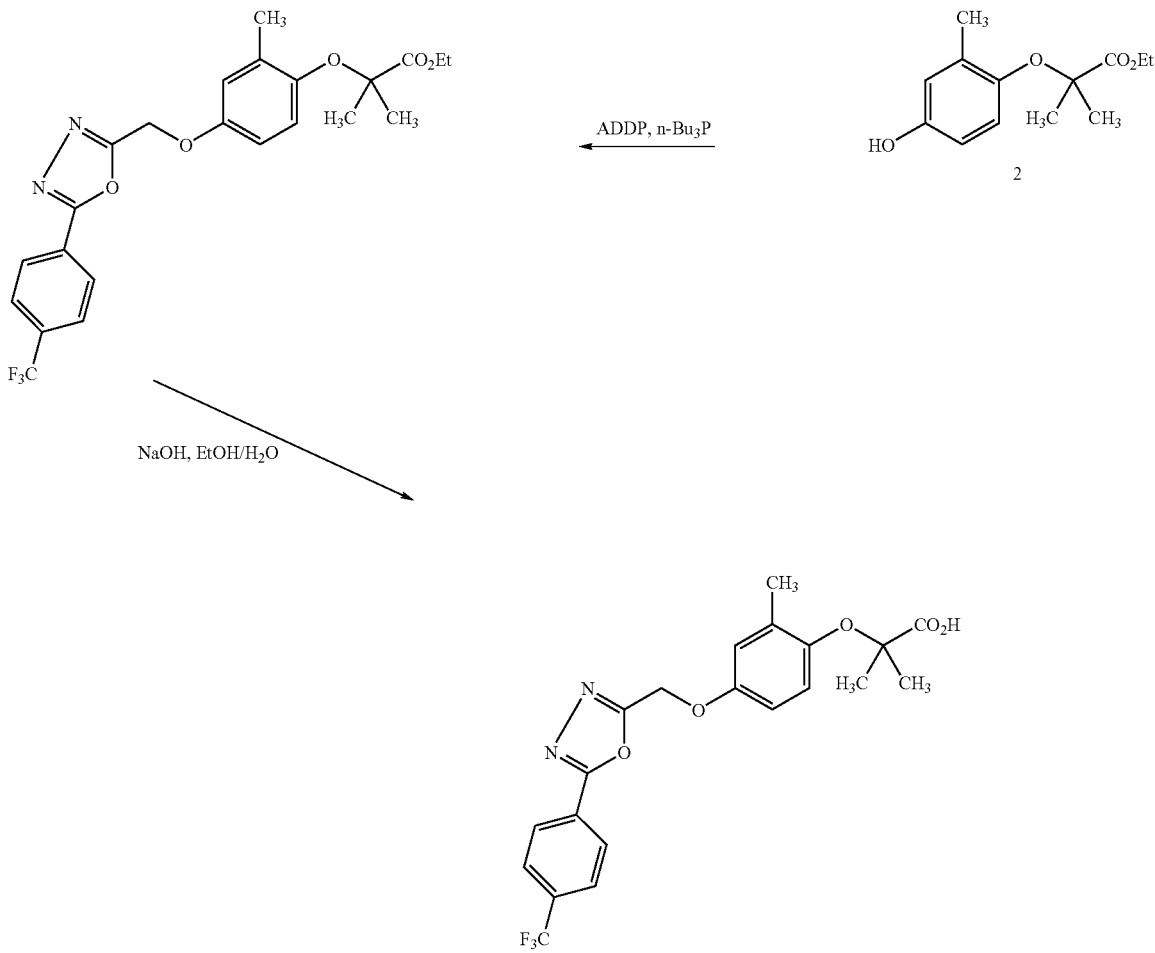

Preparation 41

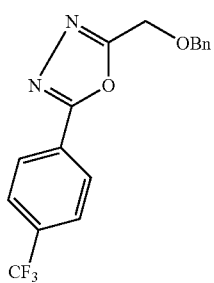

Bubble HCl (g) through a 0° C. solution of p-trifluoromethylbenzonitrile (5.50 g, 32.1 mmol) in EtOH (9.4 mL, 161 mmol) and toluene (50 mL) for 30 min. Remove the cooling bath and maintain the solution at room temperature for 16 h. Concentration of the mixture affords the intermediate imidate salt, which is added to o-xylenes (165 mL). Add the acyl hydrazine compound 1 (procedure for preparation 36) (5.78 g, 32.1 mmol) as a solution in o-xylenes (10 mL). Add $Et_3N$ (4.47 mL, 32.1 mmol) dropwise over 30 min, stir the solution for 2 hours, heat to reflux for 2.5 hours, cool to room temperature and maintain for 16 hours. Pour the solution into ½ satd. $NaHCO_3$ (250 mL) and extract with EtOAc (2×200 mL). Wash the combined organic extracts with brine (250 mL), dry over $Na_2SO_4$, filter, and concentrate. Purification of the crude product by column chromatography (0% to 15% to 20% to 25% to 35% EtOAc/hexanes) affords preparation 41 (0.53 g, 5%) as a white solid. $^1$H NMR ($CDCl_3$) δ 7.79 (d, J=8.0 Hz, 2H), 7.72 (d, J=8.0 Hz, 2 H), 7.30-7.40 (m, 5 H), 4.83 (s, 2 H), 4.70 (s, 2 H).

Preparation 42

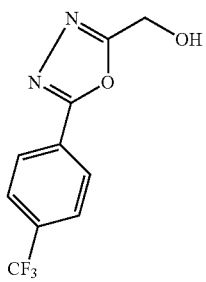

Expose a 40° C. solution of Preparation 41 (0.53 g, 1.59 mmol) and 10% Pd—C (0.10 g) in MeOH (30 mL) and THF (10 mL) to 40 psi H2 (g) for 24 h. Flushing of the mixture with N2 (g) followed by filtration through celite provides a clear solution, which is concentrated to afford preparation 42 (0.24 g, 62%) as a white solid. $^1$H NMR (CDCl$_3$) δ 8.18 (d, J=8.0 Hz, 2 H), 7.70 (d, J=8.0 Hz, 2 H), 5.00 (s, 2 H).

Preparation 43

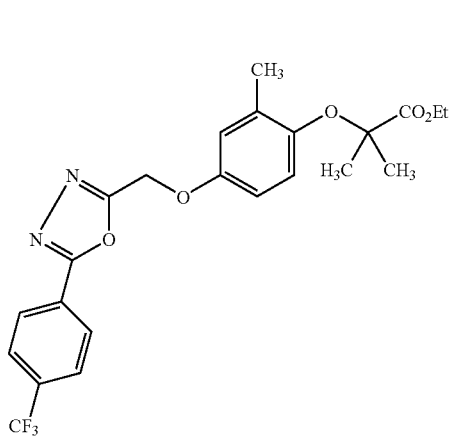

Preparation 43 is produced from preparation 42 (0.050 g, 0.20 mmol) and phenol 2 (0.051 g, 0.21 mmol) according to Preparation 39, affording preparation 43 (0.072 g, 76%) as a clear oil. $^1$H NMR (CDCl$_3$) δ 8.20 (d, J=8.4 Hz, 2H), 7.78 (d, J=8.4 Hz, 2 H), 6.85 (s, 1 H), 6.68 (m, 2 H), 5.27 (s, 2 H), 4.25 (q, J=7.2 Hz, 2H), 2.22 (s, 3 H), 1.54 (s, 6H), 1.28 (t, J=7.2 Hz, 3H).

Example 65

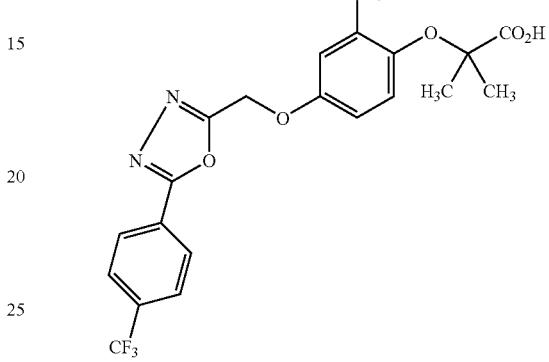

Example 65 is produced from preparation 43 according to the procedure for making example 63, affording example 65 (0.070 g, >95%) as a white solid. LRMS 455.1 (M++H).

Prepare Example 66 by a method according to Scheme 4 and prepare Example 67 by a method according to Scheme 2.

| Example | Structure | LC/MS [M + 1] |
|---|---|---|
| 66 | 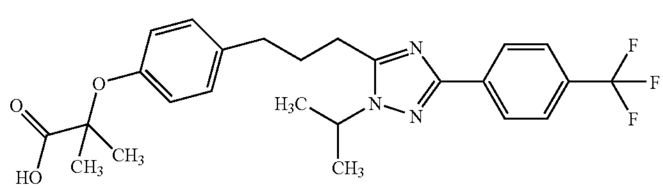 | 476.2 |
| 67 | 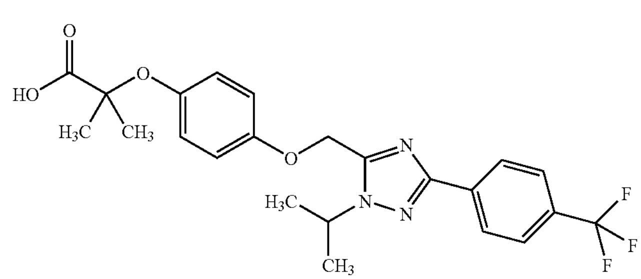 | 478.3 |

Prepare Examples 68-73 by the method described in Scheme 2 and prepare Examples 74-76 by the method described in Scheme 6a and/or 6b.
| Example | Structure | LC/MS [M + 1] |
|---|---|---|
| 68 | 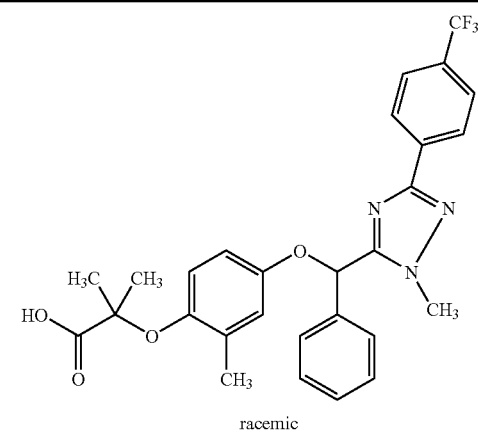 racemic | 526.2 |
| 71 | 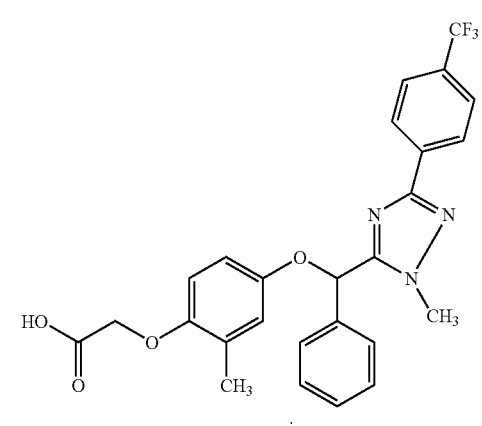 racemic | 498.1 |
| 74 | 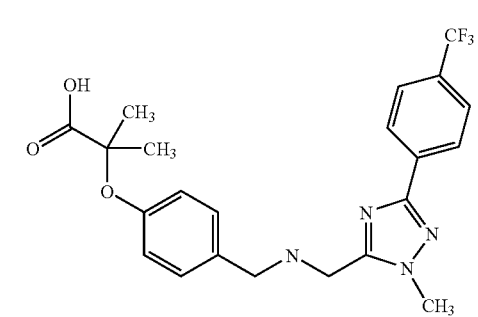 | 449.1 |
| 75 | 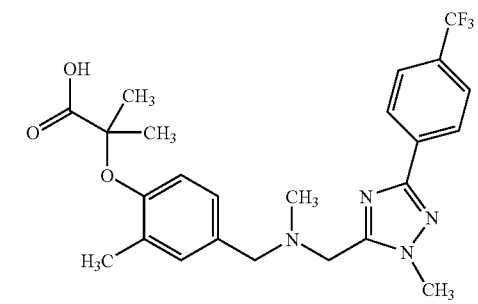 | 477.2 |

-continued

| Example | Structure | LC/MS [M + 1] |
|---|---|---|
| 76 | 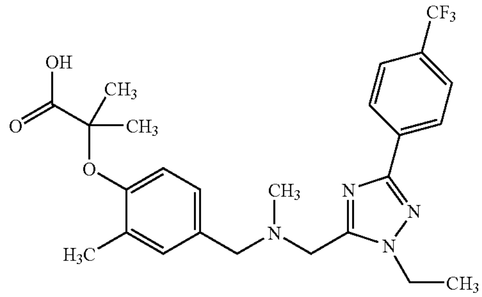 | 491.2 |

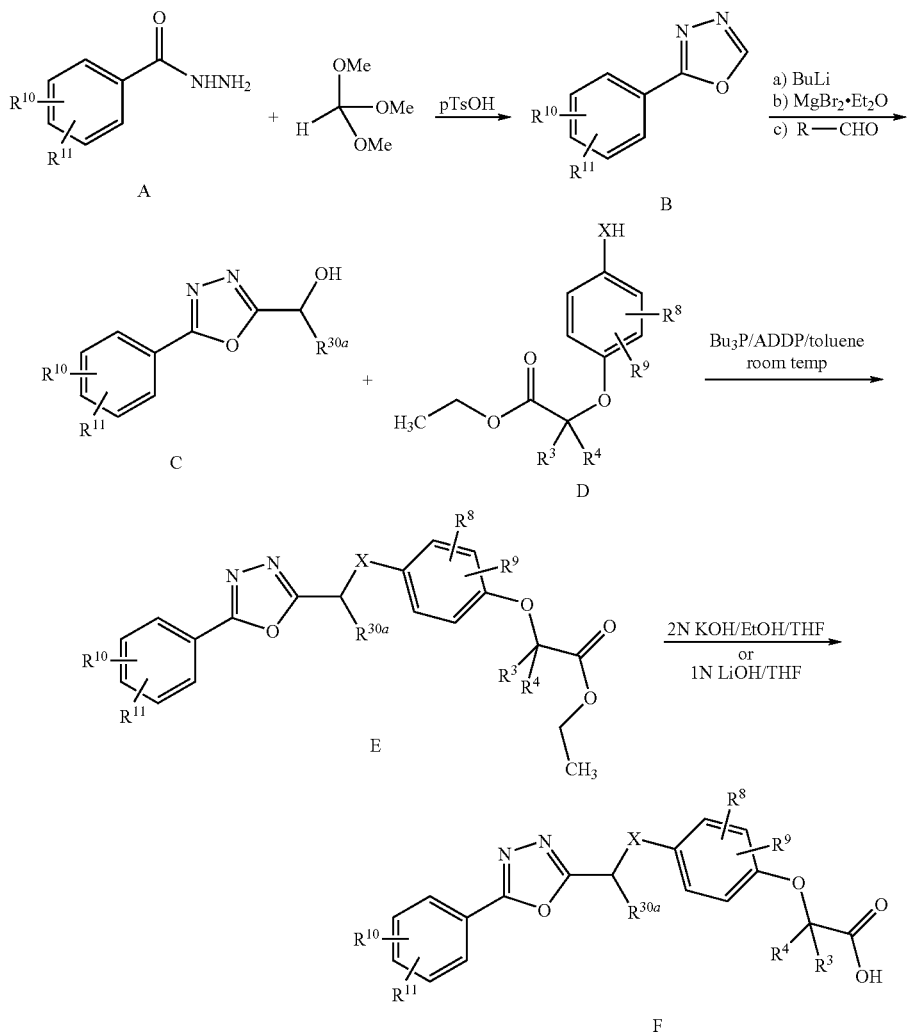

Scheme 11

General Procedure for Scheme 11

Suspend the hydrazide compound A (100 mmol) in trimethylortoformate (150 mmol) and p-toluenesulfonic acid monohydrate (1.5 mmol) to a round bottomed flask equipped with a standard distillation apparatus. Heat to 90° C. until formation of a precipitate is observed, then to 120° C. Distill the methanol. Follow the reaction by HPLC and TLC (Hex/

AcOEt 1:1). Dissolve the yellow oil in AcOEt and wash with water, brine, dry with MgSO₄ and concentrate in vacuum. Purify the crude by SiO₂ chromatography (Hex/AcOEt 9:1 to 7:3) to obtain a compound of formula B of Scheme 11.

Add nBuLi (1.6 M in hexane) dropwise (10 mmol) under N₂ atmosphere to a cooled (−78° C.) solution of the oxadiazole compound B (10 mmol) in THF (33 mL). After 40 min, add MgBr₂.Et₂O (10 mmol), warm the cooling bath to −45° C. and stir the resulting slurry at −45° C. for additional 1.5 h. Add the aldehyde (9 mmol) in THF (11 mL), raise the reaction temperature to −20° C. and stir for additional 2.5 h at this temperature. Follow the reaction by HLPC and TLC (Hex/AcOEt 8:2). Quench the crude material with a NH₄Cl solution and add AcOEt. Extract the aqueous layer twice with AcOEt. Separate the organic layer, wash it with water, brine, dry with MgSO₄, filter and concentrate in vacuum. Purify the crude material by SiO₂ chromatography (Hex/AcOEt 95:5 to 85:15) to obtain a compound of formula C of Scheme 11.

Mitsounobu reaction: Add to a solution of oxadiazole C (1.0 mmol) and the phenol (compound D) (2 mmol) in toluene (20 mL), degassed several times, Bu₃P (2.0 mmol) and ADDP (2.0 mmol) to 0° C. Stir the mixture at room temperature overnight. Follow the reaction by TLC. Remove the solvent under vacuum, triturate the residue with diethyl ether and filter off the precipitate obtained. Wash the filtrate with a 2N NaOH solution, water, brine, dry over MgSO4, and concentrate in vacuum. Purify the crude by SiO₂ chromatography (Hexane/AcOEt 95:5 to 85:15) to obtain compound E of Scheme 11.

Hydrolysis: Add a 2 N KOH solution (1.5 mL) to a solution of oxadiazole C (1.0 mmol) in EtOH/THF mixture (1:1) (40 mL) and stir the mixture at room temperature overnight. Follow the reaction by TLC (Hex/AcOEt 1:1) and HPLC. Add AcOEt and water and adjust the pH to 6 by addition a 6 N HCl solution. Separate the two phases, extract the aqueous layer twice with AcOEt, wash the organic layer with water, brine, dry over MgSO₄, filter and concentrate in vacuum. Purify the crude by ISCO (Hex-TFA 0.05%/acetone 9:1 to 85:15) to obtain the acid compound F of Scheme 11.

Preparation of Head H2

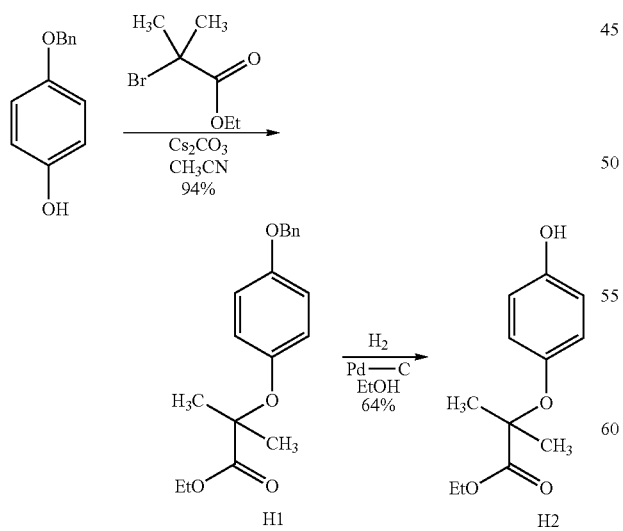

Dissolve the p-benzyloxyphenol (300 mmol) in CH₃CN (750 mL), add Cs₂CO₃ (360 mmol) portionwise, followed by the bromoderivative. Reflux the resulting mixture overnight. Cool, filter through a plug of Celite, and concentrate in vacuum. Purify by SiO₂ chromatography (Hex/AcOEt 8:2) to obtain the compound H1 in 94% yield.

Add Pd—C (10% in weight) to a solution of H1 (282 mmol) in EtOH (940 mL). Stir the mixture under H₂ atmosphere at room temperature overnight. Filter through a plug of Celite, remove the solvent and purify by Biotage (Hex/AcOEt 7:3) to obtain the compound H2 in 64% yield.

Preparation of Head H4

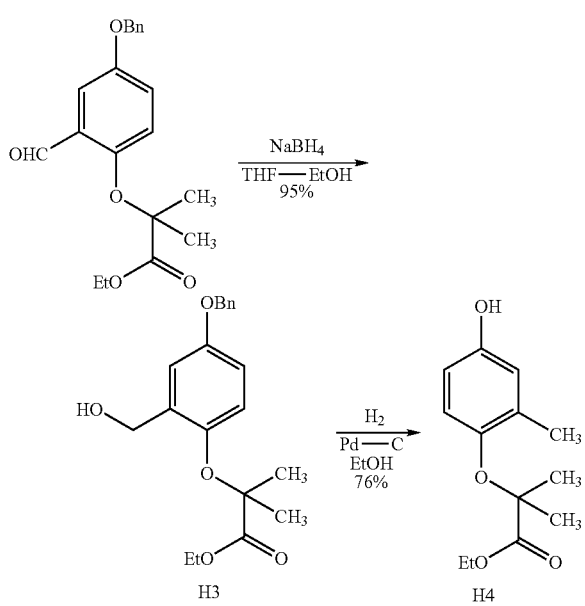

Dissolve the starting aldehyde (45 mmol) in THF:EtOH (95:5 mL), cool to 0° C., and add NaBH₄ portionwise until the starting material is not detected by TLC. Quench at 0° C. with a 1N HCl and add AcOEt. Adjust the pH to 6. Separate the two phases, extract twice with AcOEt. Wash with water, brine, dry over MgSO₄ filter and concentrate under vacuum. Purify by SiO₂ chromatography to obtain the alcohol H3 in 95% yield.

Add Pd—C (10% in weight) to a solution of H3 (42.7 mmol) in EtOH (430 mL). Stir the mixture under H₂ atmosphere at room temperature for 6 h. Filter through a plug of Celite, remove the solvent and purify by SiO₂ chromatography (Hex/AcOEt 7:3) to obtain the compound H4 in 76% yield.

Preparation of Head H7

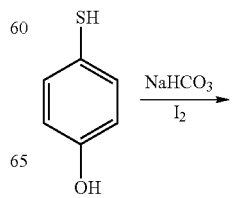

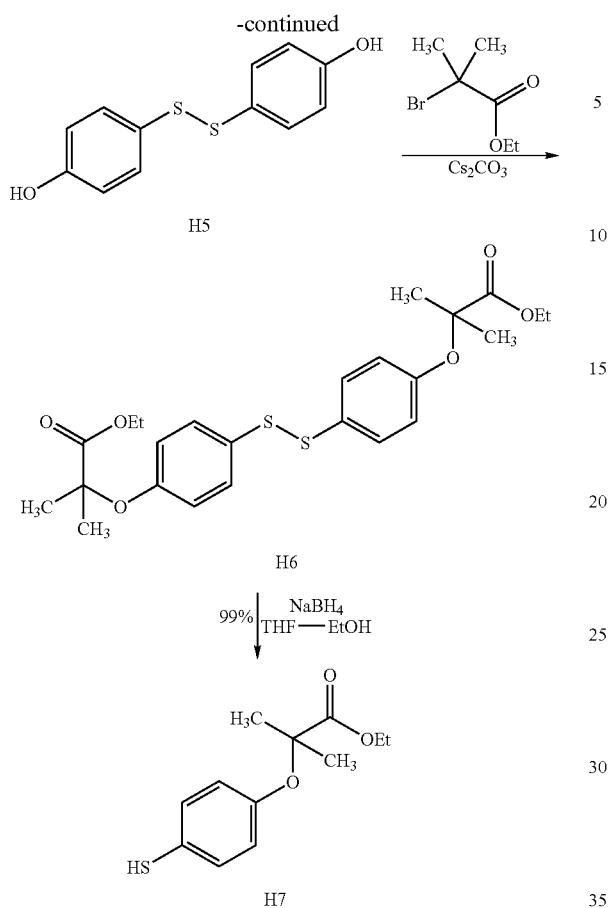

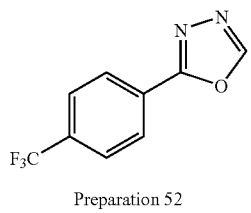

Preparation 52

Suspend the hydrazide (5 g) in trimethylortoformate (4.0 ml) and p-toluenesulfonic acid monohydrate (47 mg) to a round bottomed flask equipped with a standard distillation apparatus. Heat to 90° C. until formation of a precipitate is observed, then to 120° C. Distill the methanol to obtain a yellow oil. Dissolve the yellow oil in AcOEt and wash with water, brine, dry with MgSO₄ and concentrate in vacuum. Purify the crude by SiO₂ chromatography (Hex/AcOEt 9:1 to 7:3) to obtain preparation 52 as a white solid. (95%).

Preparation 53

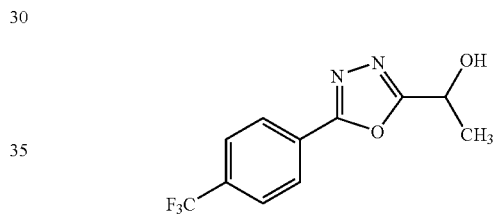

Dissolve the thiol (100 mmol) in MeOH (170 mL), cool to 0° C. and add I₂ (0.5 mmol) and NaHCO₃ (2.8 mmol) portionwise. Stir the resulting mixture at room temperature overnight. Remove the solvent under vacuum and purify the residue by SiO₂ chromatography to obtain the compound H5 in 83% yield.

Dissolve the disulfide H5 (70 mmol) in CH₃CN (110 mL), add Cs₂CO₃ (3.5 mmol), stir for 10 minutes and then add the bromoderivative (210 mmol). Reflux overnight. Follow the reaction by TLC (Hexane/AcOEt 7:3). Cool to room temperature, filter through a plug of Celite, concentrate in vacuum and purify the residue by SiO₂ chromatography (Hexane to Hexane/AcOEt 4:1) to obtain the compound H6 in 51% yield.

Dissolve H6 (6 mmol) in THF:EtOH (16:5 mL), add NaBH₄ portionwise at 0° C. until starting material was not detected. Quench with a 1N HCl solution to 0° C. and add AcOEt. Adjust the pH to 4. Separate the two phases, extract twice with AcOEt. Wash with water, brine, dry over MgSO₄, filter and concentrate. Purify by SiO₂ chromatography (Hex to Hex/AcOEt95:5) to obtain H7 in 99% yield.

Preparation 52

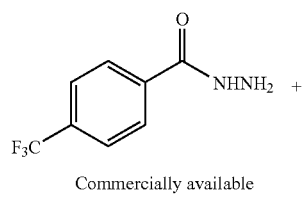

Commercially available

Add nBuLi (1.51 ml, 1.7M in pentane) dropwise, under N₂ atmosphere to a cooled (−78° C.) solution of preparation 52 (500 mg) in THF (20 mL). After 40 min, add MgBr₂.Et₂O (10 mmol), warm the cooling bath to −45° C. and stir the resulting slurry at −45° C. for additional 1.5 h. Add aectaldehyde (0.157 ml) in THF (10 mL), raise the reaction's temperature to −20° C. and stir for additional 2.5 h at this temperature. Quench the crude material with a NH₄Cl solution and add AcOEt. Extract the aqueous layer twice with AcOEt. Separate the organic layer, wash it with water, brine, dry with MgSO₄, filter and concentrate in vacuum. Purify the crude material by SiO₂ chromatography (Hex/AcOEt 95:5 to 85:15) to obtain preparation 53. (22%)

Preparation 54

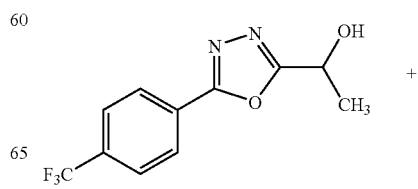

+

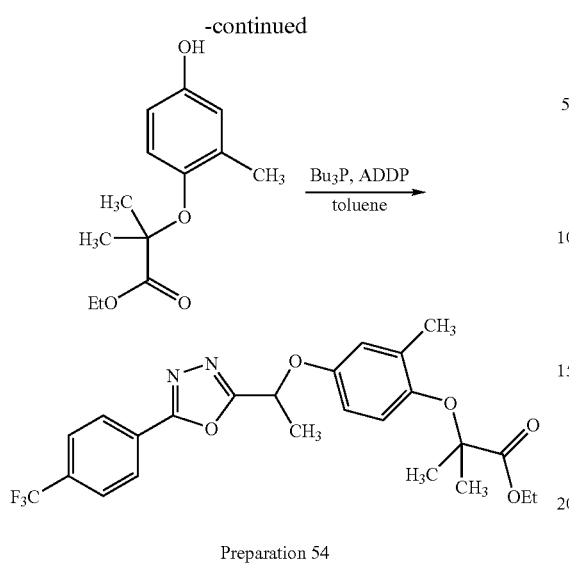

Preparation 54

Mitsounobu reaction: Add to a solution of preparation 53 (24 mg) and the phenol (26.5 mg) in toluene (2 mL), degassed several times, Bu₃P (0.035 ml) and ADDP (35 mg) to 0° C. Stir the mixture at room temperature overnight. Remove the solvent under vacuum, triturate the residue with diethyl ether and filter off the precipitate obtained. Wash the filtrate with a 2N NaOH solution, water, brine, dry over MgSO4, and concentrate in vacuum. Purify the crude by SiO₂ chromatography (Hexane/AcOEt 95:5 to 85:15) to obtain preparation 54. (55%).

EXAMPLE 77

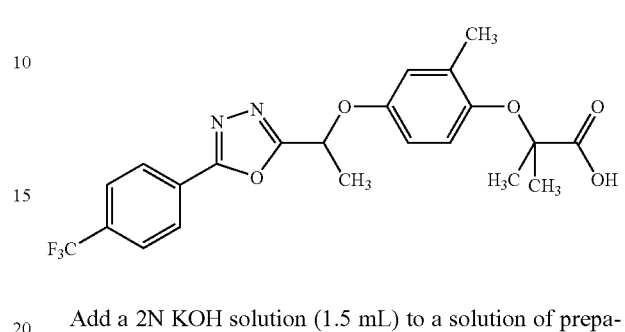

Add a 2N KOH solution (1.5 mL) to a solution of preparation 54 (24 mg) in EtOH/THF mixture (1:1) (4 mL) and stir the mixture at room temperature overnight. Add AcOEt and water and adjust the pH to 6 by addition a 1N HCl solution. Separate the two phases, extract the aqueous layer twice with AcOEt, wash the organic layer with water, brine, dry over MgSO₄, filter and concentrate in vacuum. Purify the crude by Purify the crude by SiO₂ chromatography (Hexane/AcOEt 95:5 to 85:15) to obtain example 77. (90%).

Prepare Examples 78, 81, 84, 85, and 88-90 using a similar procedure to prepare example 77.

| Example | Structure | LC/MS [M + 1] |
|---|---|---|
| 77 | racemic | 451 |
| 78 | racemic | 478.5 |
| 81 | racemic | 492.5 |

-continued

| Example | Structure | LC/MS [M + 1] |
|---------|-----------|---------------|
| 84 | racemic | 494.5 |
| 85 | racemic | 518.4 |
| 88 | racemic | 532.4 |
| 89 | racemic | 534.5 |
| 90 | racemic | 512.5 |

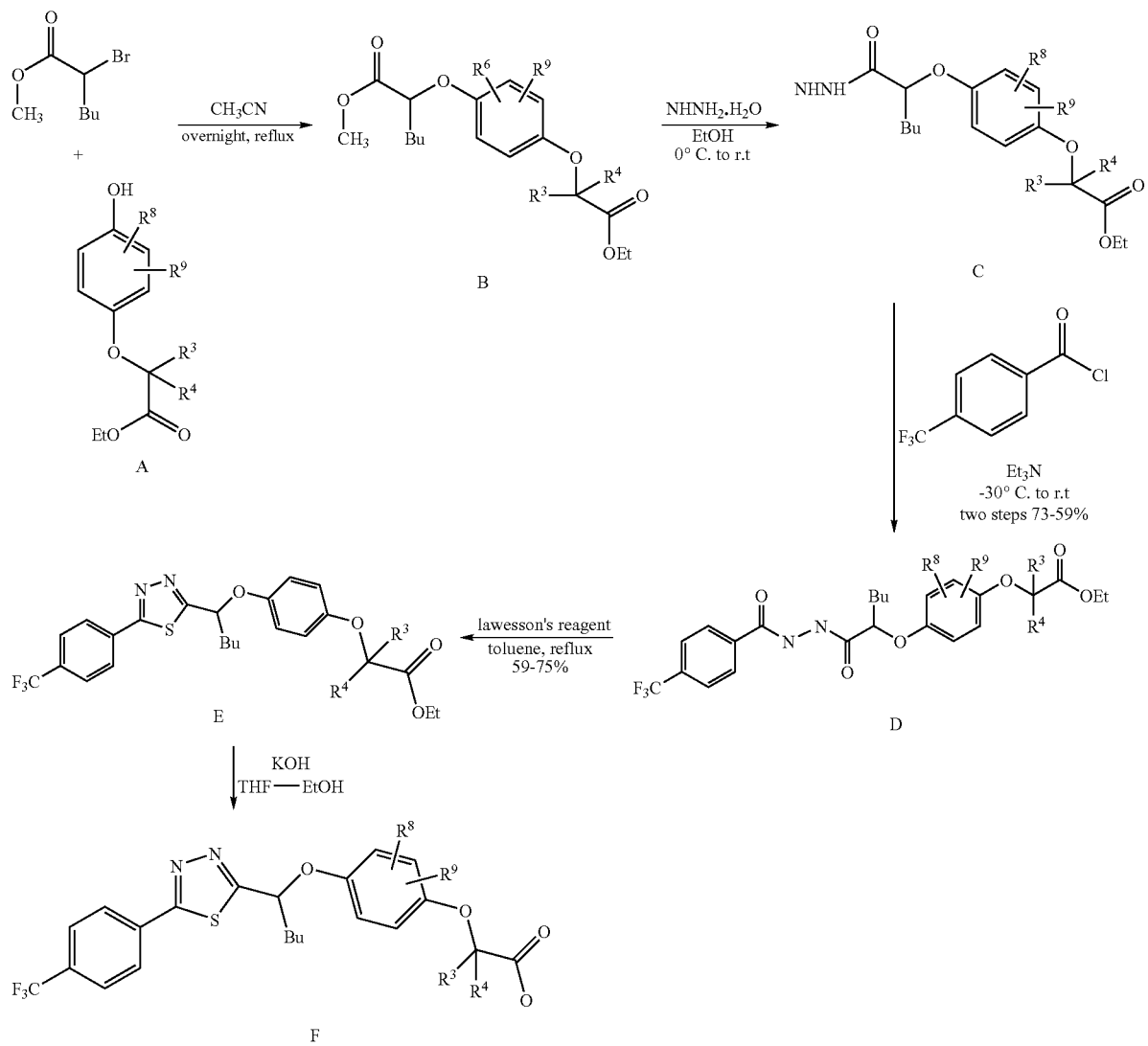

Scheme 12

General Procedure for Scheme 12

Add the commercial ester starting material (10 mmol) to a suspension of the phenol A (10 mmol) and the $K_2CO_3$ in $CH_3CN$ (10 mL). Reflux the mixture overnight. Follow the reaction by TLC (Hexane/AcOEt 9:1). Cool, filter through a plug of Celite and remove the solvent under vacuum. Purify the crude material by $SiO_2$ chromatography (Hexane to Hex/AcOEt 9:1) to obtain a compound of formula B of Scheme 12.

Dissolve the methyl ester B (10 mmol) in EtOH (12.5 mL). Then, add hydrazine monohydrate (40 mmol). Stir the mixture at room temperature overnight. Follow the reaction by TLC (Hexane/AcOEt 9:1). Remove the solvent under vacuum. Dissolve the residue in AcOEt and wash with water. Dry the organic layer over $MgSO_4$ and concentrate. Use the crude material without further purification.

Dissolve the hydrazide C (10 mmol) in THF (25 mL). Add $Et_3N$ at 0° C. and stir the resulting solution for 5 min, then add the acid chloride (11 mmol) at −30° C. dropwise. Stir the mixture at this temperature for 45 min and then at room temperature overnight. Follow the reaction by HPLC and TLC (Hex/AcOEt 1:1). Quench the crude material with water and add AcOEt. Separate the organic layer, dry with $MgSO_4$, and concentrate in vacuum. Purify the crude material by $SiO_2$ chromatography (Hex/AcOEt 9:1 to 7:3) to obtain a compound of formula D of Scheme 12.

Dissolve the compound D (10 mmol) in toluene (100 mL), add the Lawesson's reagent (20.0 mmol). Reflux the mixture for 4 h. Follow the reaction by TLC (Hexane/AcOEt 4:1). Remove the solvent under vacuum. Purify the residue by $SiO_2$ chromatography (Hex to Hex/AcOEt 85:15) to obtain a compound of formula E in Scheme 12.

Add 2N KOH solution (1.5 mL) to a solution of thiodiazole E (1.0 mmol) in EtOH/THF mixture (1:1) (40 mL) and stir the mixture at room temperature overnight. Follow the reaction by TLC (Hex/AcOEt 1:1) and HPLC. Add AcOEt and water and adjust the pH to 6 by addition a 6 N HCl solution. Separate the two phases, extract the aqueous layer twice with AcOEt, wash the organic layer with water, brine, dry over $MgSO_4$, filter and concentrate in vacuum. Purify the crude by ISCO (Hex-TFA 0.05%/acetone 9:1 to 85:15) to obtain the acid F of Scheme 12.

EXPERIMENTAL PROCEDURE FOR EXAMPLE 91

Preparation 55

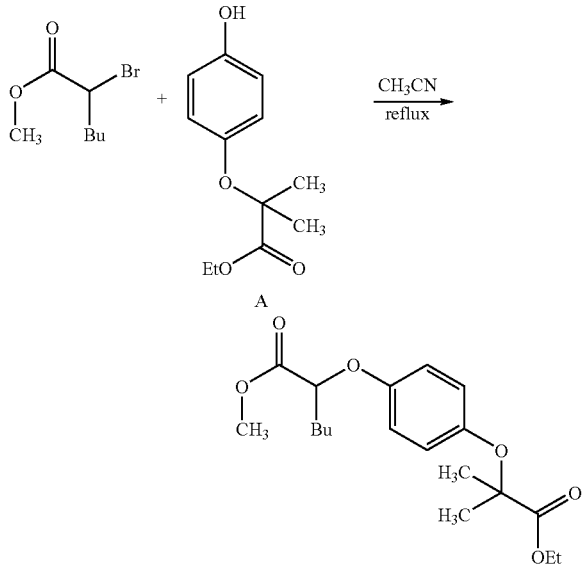

Preparation 55

Add the commercial starting material (167 mg) to a suspension of the phenol A (224 mg) and the K₂CO₃ in CH₃CN (10 mL). Reflux the mixture overnight. Cool, filter through a plug of Celite and remove the solvent under vacuum. Purify the crude material by SiO₂ chromatography (Hexane to Hex/AcOEt 9:1) to obtain preparation 55 in a yield 95%.

Preparation 56

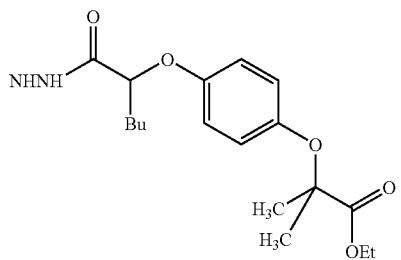

Dissolve the preparation 55 (300 mg) in EtOH (12.5 mL). Then, add hydrazine monohydrate (190 mg). Stir the mixture at room temperature overnight. Remove the solvent under vacuum, dissolve the residue in AcOEt and wash with water. Dry the organic layer over MgSO₄ and concentrate. Use the crude material without further purification.

Preparation 57

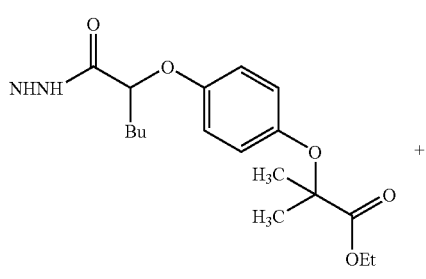

Preparation 56

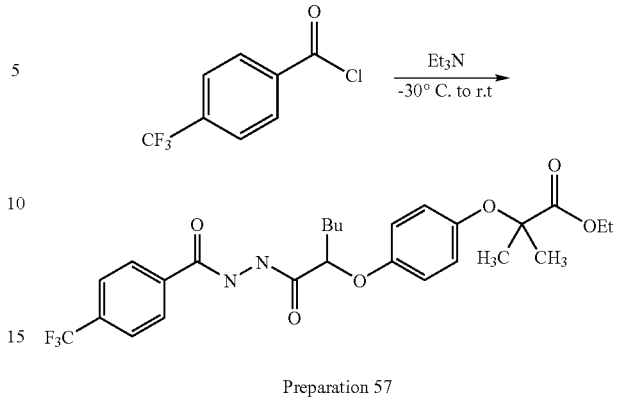

Preparation 57

Dissolve preparation 56 (300 mg) in THF (25 mL). Add Et₃N at 0° C. and stir the resulting solution for 5 min, then add the commercially available acid chloride (160 mg) at −30° C. dropwise. Stir the mixture at this temperature for 45 min and then at room temperature overnight. Quench the crude material with water and add AcOEt. Separate the organic layer, dry with MgSO₄, and concentrate in vacuum. Purify the crude material by SiO₂ chromatography (Hex/AcOEt 9:1 to 7.3) to obtain preparation 57 which yields 60% for the two steps.

Preparation 58

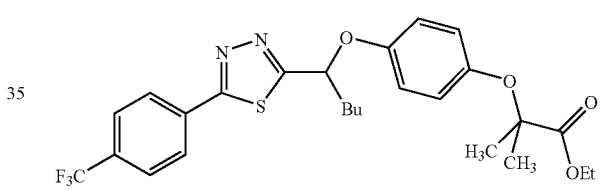

Dissolve preparation 57 (127 mg) in toluene (5 mL) and add the Lawesson's reagent (134 mg). Reflux the mixture for 4 h. Remove the solvent under vacuum and purify the residue by SiO₂ chromatography (Hex to Hex/AcOEt 85:15) to obtain preparation 58 in 60% yield.

EXAMPLE 91

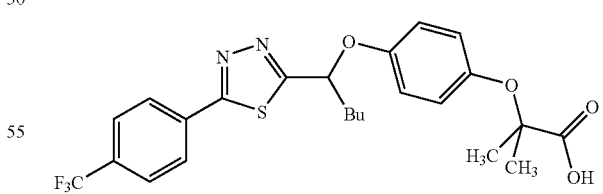

Add a 2 N KOH solution (1.5 mL) to a solution of preparation 58 (24 mg) in EtOH/THF mixture (1:1) (4 mL) and stir the mixture at room temperature overnight. Add AcOEt and water and adjust the pH to 6 by addition a 1N HCl solution. Separate the two phases, extract the aqueous layer twice with AcOEt, wash the organic layer with water, brine, dry over MgSO₄, filter and concentrate in vacuum. Purify the crude by SiO₂ chromatography to obtain example 91. (90%).

Prepare Example 94 using a similar procedure to prepare example 91.
| Example | Structure | LC/MS [M + 1] |
|---|---|---|
| 91 | racemic | 494.5 |
| 94 | racemic | 508.6 |
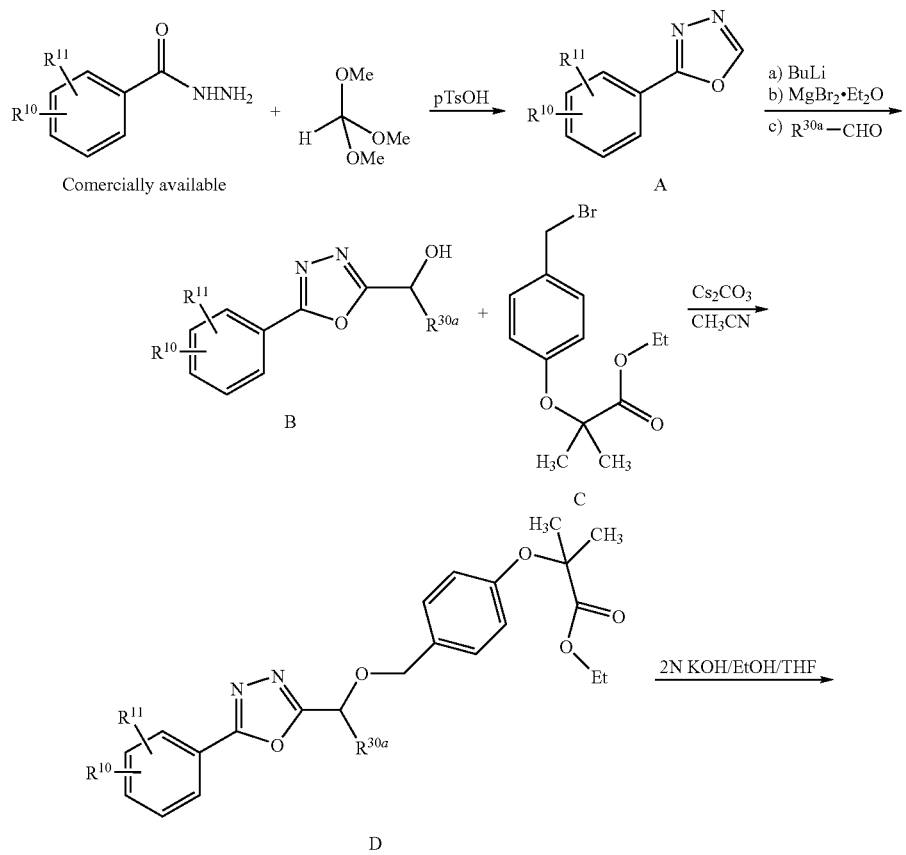
Scheme 13

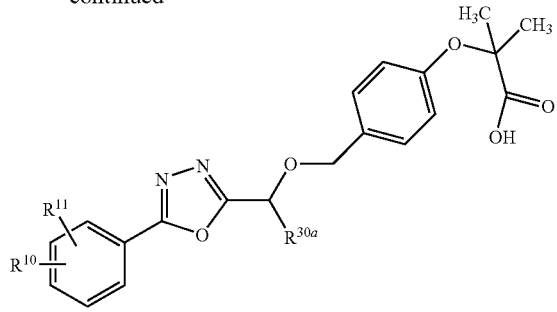

E

EXPERIMENTAL PROCEDURE FOR SCHEME 13

Add the hydrazide (100 mmol), trimethylortoformate (150 mmol) and p-toluenesulfonic acid monohydrate (1.5 mmol) to a round bottomed flask-equipped with a standard distillation apparatus. Heat to 90° C. until a precipitate is obtained, then heat to 120° C. Distill the methanol to obtain an oil. Follow the reaction by HPLC and THC (Hex/AcOEt 1:1). Dissolve the oil in AcOEt and wash with water, brine, dry with $MgSO_4$, and concentrate in vacuum. Purify the crude by $SiO_2$ chromatography (Hex/AcOEt 9:1 to 7:3) to obtain an oxadiazole compound of formula A of Scheme 13.

Add nBuLi (1.6M in hexane) dropwise (10 mmol) under $N_2$ atmosphere to a cooled (−78° C.) solution of the oxadiazole (10 mmol) in THF (33 mL). After 40 min, add $MgBr_2.Et_2O$ (10 mmol), warm the cooling bath to −45° C. and stir the resulting slurry at −45° C. for additional 1.5 h. Add the aldehyde (9 mmol) in THF (11 mL), raise the reaction's temperature to −20° C. and stir for additional 2.5 h at this temperature. Follow the reaction by HLPC and TLC (Hex/AcOEt 8:2). Quench the crude material with a $NH_4Cl$ solution and add AcOEt. Extract the aqueous layer twice with AcOEt. Separate the organic layer, wash it with water, brine, dry with $MgSO_4$, filter and concentrate in vacuum. Purify the crude material by $SiO_2$ chromatography (Hex/AcOEt 95:5 to 85:15) to obtain a compound of formula B of Scheme 13.

To a solution of oxadiazole B (1.0 mmol) and the bromoderivative C (1.1 mmol) in $CH_3CN$ (2.5 mL), add $Cs_2CO_3$ (1.3 mmol), and stir at room temperature the resulting mixture overnight. Follow the reaction by TLC (Hexane/AcOEt 4:1). Filter through a plug of Celite. Remove the solvent under vacuum. Purify the crude by $SiO_2$ chromatography (Hexane/AcOEt 95:5 to 85:15) to obtain compound D of Scheme 13.

Add 2 N KOH solution (1.5 mL) to a solution of oxadiazole D (1.0 mmol) in EtOH/THF mixture (1:1) (40 mL) and stir the mixture at room temperature overnight. Follow the reaction by TLC (Hex/AcOEt 1:1) and HPLC. Add AcOEt and water and adjust the pH to 6 by addition a 6N HCl solution. Separate the two phases, extract the aqueous layer twice with AcOEt, wash the organic layer with water, brine, dry over $MgSO_4$, filter and concentrate in vacuum. Purify the crude by ISCO (Hex-TFA 0.05%/acetone 9:1 to 85:15) to obtain the acid E of Scheme 13.

Preparation of the Bromoderivative

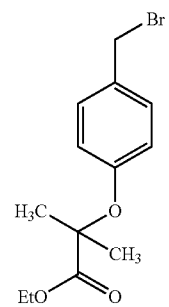

Preparation of Head H9

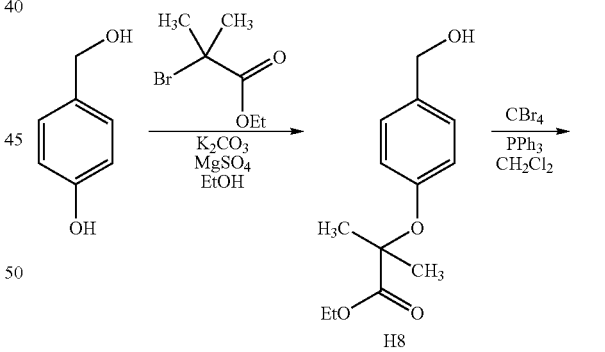

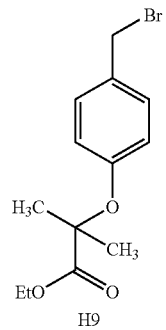

H9

Dissolve the phenol (154 mmol) in EtOH (513 mL), add K$_2$CO$_3$ (600 mmol) and MgSO$_4$ and then, the bromoderivative (231 mmol). Reflux the resulting mixture overnight. Cool, filter through a plug of Celite, concentrate in vacuum. Purify by SiO$_2$ chromatography (Hex/AcOEt 8:2) to obtain the compound H8 in 53% yield.

Dissolve H8 (13 mmol) in CH$_2$Cl$_2$ (130 mL) at 0 20 C., add CBr$_4$ and then PPh$_3$ portionwise. Stir the mixture at 0° C. for 2 hours. Follow the reaction by TLC (Hex/AcOEt 4:1). Remove the solvent. Purify the residue by SiO$_2$ chromatography (Hexane/AcOEt 9:1) to obtain H9 in 95% yield.

EXPERIMENTAL PROCEDURE FOR EXAMPLE 97

Preparation 59

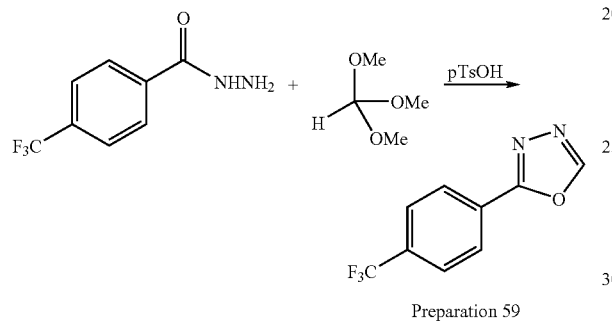

Preparation 59

Suspend the hydrazide (5 g) in trimethylortoformate (4.0 ml) and p-toluenesulfonic acid monohydrate (47 mg) to a round bottomed flask equipped with a standard distillation apparatus. Heat to 90° C. until formation of a precipitate is observed, then to 120° C. Distill the methanol to obtain a yellow oil. Dissolve the yellow oil in AcOEt and wash with water, brine, dry with MgSO$_4$ and concentrate in vacuum. Purify the crude by SiO$_2$ chromatography (Hex/AcOEt 9:1 to 7:3) to obtain preparation 59 as a white solid. (95%).

Preparation 60

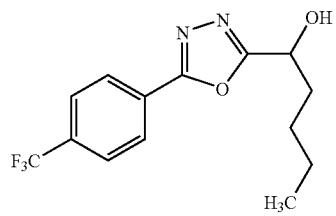

Add nBuLi (1.51 ml, 1.7M in pentane) dropwise, under N$_2$ atmosphere to a cooled (−78° C.) solution of the oxadiazole (500 mg) in THF (20 mL). After 40 min, add MgBr$_2$.Et$_2$O (10 mmol), warm the cooling bath to −45° C. and stir the resulting slurry at −45° C. for additional 1.5 h. Add butyraldehyde (0.157 ml) in THF (10 mL), raise the reaction's temperature to −20° C. and stir for additional 2.5 h at this temperature. Quench the crude material with a NH$_4$Cl solution and add AcOEt. Extract the aqueous layer twice with AcOEt. Separate the organic layer, wash it with water, brine, dry with MgSO$_4$, filter and concentrate in vacuum. Purify the crude material by SiO$_2$ chromatography (Hex/AcOEt 95:5 to 85:15) to obtain preparation 60. (25%).

Preparation 61

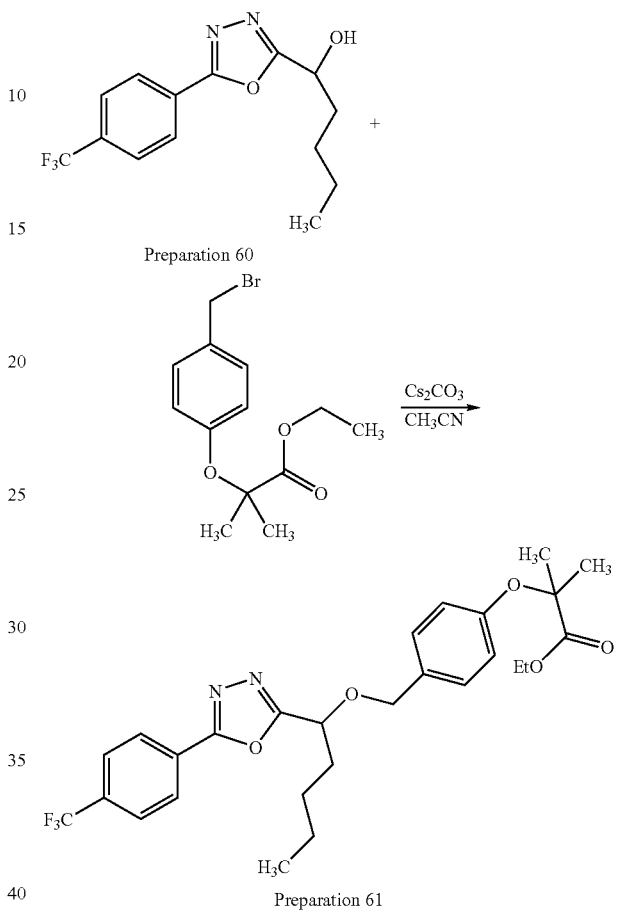

Preparation 61

To a solution of preparation 60 (80 mg) and the bromoderivative (217 mg) in CH$_3$CN (5 mL), add Cs$_2$CO$_3$ (213 mg), and stir at room temperature the resulting mixture overnight. Filter through a plug of Celite. Remove the solvent under vacuum. Purify the crude by SiO$_2$ chromatography (Hexane/AcOEt 95:5 to 85:15) to obtain preparation 61 in yield 90%.

EXAMPLE 97

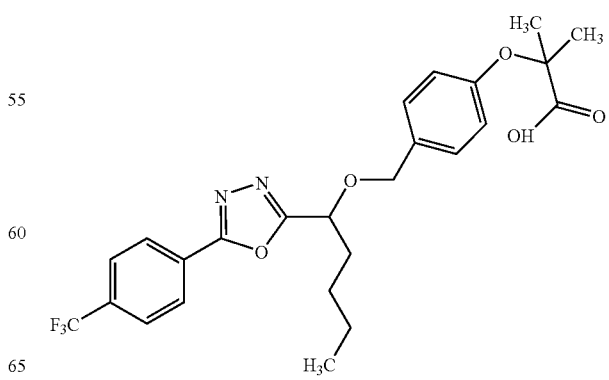

Add a 2N KOH solution (1.5 mL) to a solution of preparation 61 (24 mg) in EtOH/THF mixture (1:1) (4 mL) and stir the mixture at room temperature overnight. Add AcOEt and water and adjust the pH to 6 by addition a 1 N HCl solution. Separate the two phases, extract the aqueous layer twice with AcOEt, wash the organic layer with water, brine, dry over MgSO$_4$, filter and concentrate in vacuum. Purify the crude by Purify the crude by SiO$_2$ chromatography to obtain example 97. (85%).

Prepare Example 100 using a similar procedure to prepare example 97.

-continued

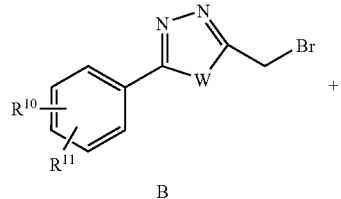

B

| Example | Structure | LC/MS [M + 1] |
|---|---|---|
| 97 | racemic | 492.5 |
| 100 | racemic | 512.5 |

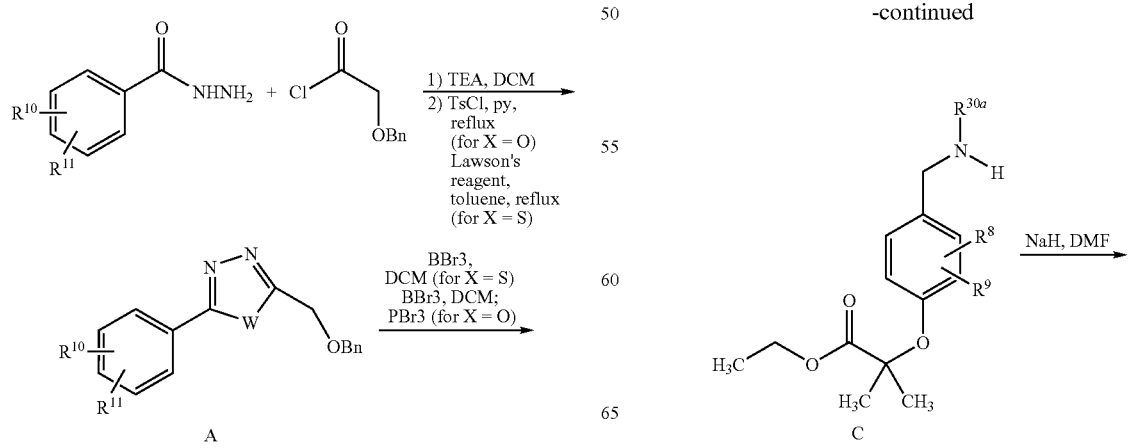

-continued

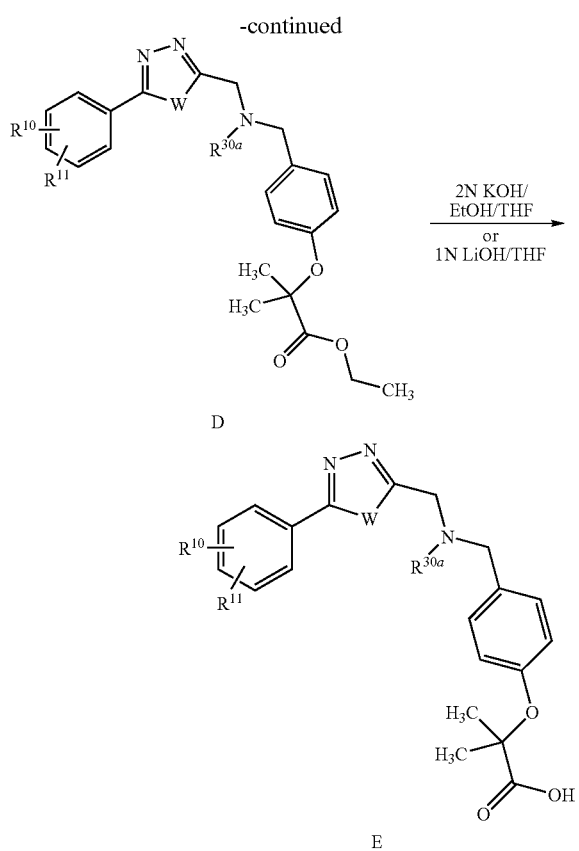

EXPERIMENTAL PROCEDURE FOR SCHEME 14

For W=O:

Slurry the commercially available hydrazide (1 eq) in DCM and then add the acid chloride (1.1 eq) followed by the triethyl amine (2 eq). Stir under nitrogen at room temperature for 12 hrs. Then quench the reaction with 1 N HCl and extract with DCM. Dry the organic layer over $MgSO_4$ and evaporate. Recrystalize the solid recrystalized from EtOAc.

Dissolve this material in pyridine and add tosyl chloride (1.5 eq.) and reflux the mixture refluxed for 18 hrs. Cool the reaction, dilute with ethyl acetate, and wash with 1 N HCl, sat. bicarb, and water. Dry the organics over $MgSO_4$ and evaporate. Purify the residue via column chromatography (20% ethyl acetate in hexanes) to obtain the compound of formula A in scheme 14.

Dissolve this material in DCM and cool to 0° C. Add $BBr_3$ (3 eq) over 10min. Allow the reaction to warm to room temperature over 2 hrs. Dilute the reaction with ethyl acetate and wash with sat. bicarb. and 1N HCl. Dry the organic over $MgSO_4$ and evaporate.

Dissolve the solid in DCM and add $PBr_3$ (1.2 eq). Stir this at room temperature for 2 hrs, wash with water, dry the organics over $MgSO_4$, and evaporate to give compound of formula B or scheme 14 without purification.

For W=S:

Slurry the hydrazide (1 eq) in DCM and add the acid chloride (1. 1 eq) followed by the triethyl amine (2 eq). Stir this under nitrogen at room temperature for 12 hrs. Quench the reaction with 1N HCl and extract with DCM. Dry the organic layer over $MgSO_4$ and evaporate. Recrystalize the solid from EtOAc.

Dissolve this material in pyridine, add tosyl chloride (1.5 eq.), and reflux the mixture for 18 hrs. Cool the reaction, dilute with ethyl acetate, and wash with 1N HCl, sat. bicarb, and water. Dry the organics over $MgSO_4$ and evaporate. Purify the residue via column chromatography (20% ethyl acetate in hexanes) to obtain the compound of formula A of scheme 14.

Dissolve the material in DCM and cool to 0° C. Add $BBr_3$ (3 eq) over 10 min. Then, allow the reaction to warm to room temperature over 2 hrs. Dilute the reaction with ethyl acetate and wash with sat. bicarb. and 1N HCl. Dry the organic over $MgSO_4$ and evaporate.

Synthesis of Compound D:

Dissolve the appropriate amine headpiece (compound of formula C) in DMP and cool to 0° C. Add to this NaH (1 eq) and stir for 30 min. Add compound B (0.9 eq) and allow the reaction to slowly warm to room temperature. After complete comsumption of the starting material, quench the reaction with sat. ammonium chloride and extract with ethyl acetate. Dry the organic over $MgSO_4$ and evaporate. Purify the residue via column chromatography (20% ethyl acetate in hexanes) to give the compound of formula D of scheme 14.

Synthesis of Compound E:

Add 1 N NaOH solution (1.5 mL) to a solution of compound of formula D (1.0 mmol) in MeOH/THF mixture (1:1) (40 mL) and stir the mixture at room temperature overnight. Follow the reaction by TLC (Hex/AcOEt 1:1) and HPLC. Add AcOEt and water and adjust the pH to 6 by addition a 1 N HCl solution. Separate the two phases, extract the aqueous layer twice with AcOEt, wash the organic layer with water, brine, dry over $MgSO_4$, filter and concentrate in vacuum. This residue is then purified via column chromatography (30% ethyl acetate in hexanes) to give the product E.

EXPERIMENTAL PROCEDURE FOR EXAMPLE 104

Preparation 62

Slurry 4-trifluoromethylbenzhydrazine (1 g) in DCM (25 ml) and add to this mixture the benzyloxyacetyl chloride (0.837 ml), followed by the triethyl amine (1.37 ml). Stir this under nitrogen at room temperature for 12 hrs. Then, quench the reaction with 1 N HCl and extract with DCM. Dry the organic layer over $MgSO_4$ and evaporate. Recrystalize the solid from EtOAc. (93%).

Dissolve this material in toluene and add Lawsen's reagent (3 g) and reflux the mixture for 18 hrs. Then, cool the reaction and dilute with ethyl acetate and wash with 1 N HCl, sat. bicarb, and water. Dry the organics over $MgSO_4$ and evaporate. Purify this residue via column chromatography (20% ethyl acetate in hexanes) to give preparation 62 as a pale yellow solid. (80%).

Preparation 63

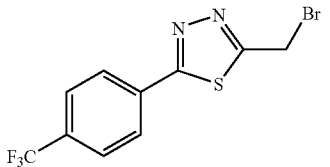

Dissolve preparation 62 (100 mg) in DCM (5 ml) and cool to 0° C. Add to this BBr₃ (0.788 ml)) over 10 min. Allow the reaction to warm to room temperature over 2 hrs. Dilute the reaction with ethyl acetate and wash with sat. bicarb. and 1 N HCl. Dry the organic over MgSO₄ and evaporate to give preparation 63 as an off white solid. (98%)

Preparation 64

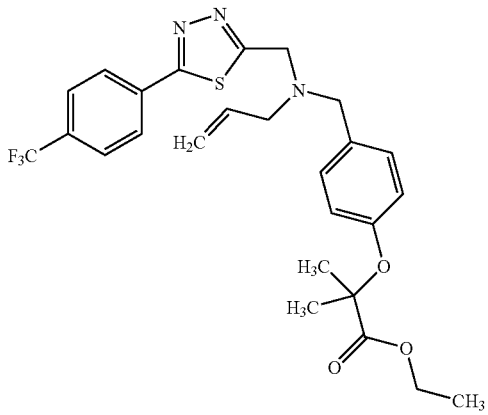

Dissolve the headpiece (429 mg) in acetonitrile (20 ml) and cool to 0° C. Add to this CsCO₃ (1 g), and preparation 63 (500 mg) and allow the reaction to slowly warm to room temperature. After complete comsumption of the starting material, quench the reaction with sat. ammonium chloride and extract with ethyl acetate. Dry the organic over MgSO₄ and evaporate. Purify the residue via column chromatography (20% ethyl acetate in hexanes) to give preparation 64. (62%)

EXAMPLE 104

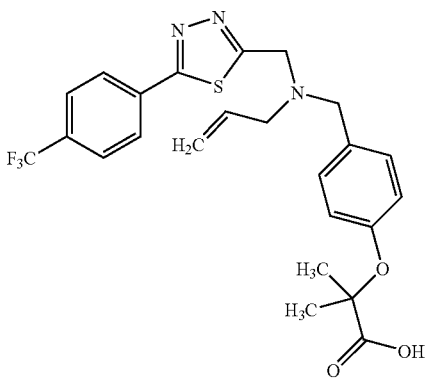

Add a 2N KOH solution (1.5 mL) to a solution of preparation 64 (24 mg) in EtOH/THF mixture (1:1) (4 mL) and stir the mixture at room temperature overnight. Add AcOEt and water and adjust the pH to 6 by addition a 1N HCl solution. Separate the two phases, extract the aqueous layer twice-with AcOEt, wash the organic layer with water, brine, dry over MgSO₄, filter and concentrate in vacuum. Purify the crude by SiO₂ chromatography (Hexane/AcOEt 95:5 to 85:15) to give the example 104. (80%).

Prepare Examples 105-112 using a similar procedure to prepare example 104.

| Example | Structure | LC/MS [M + 1] |
|---|---|---|
| 104 | 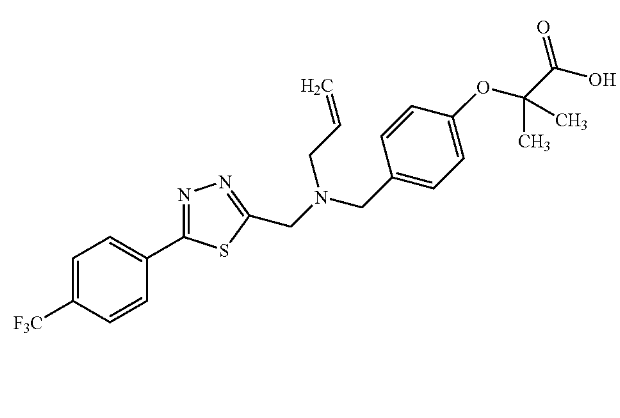 | 492 |

| Example | Structure | LC/MS [M + 1] |
|---|---|---|
| 105 | 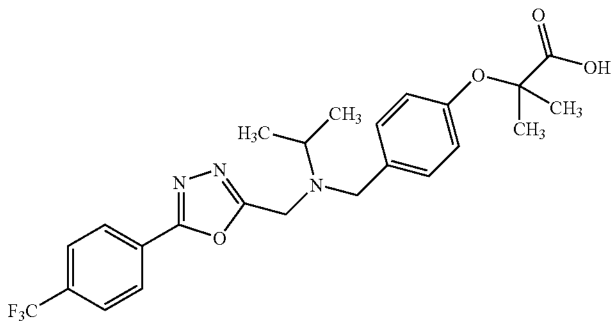 | 476 |
| 106 | 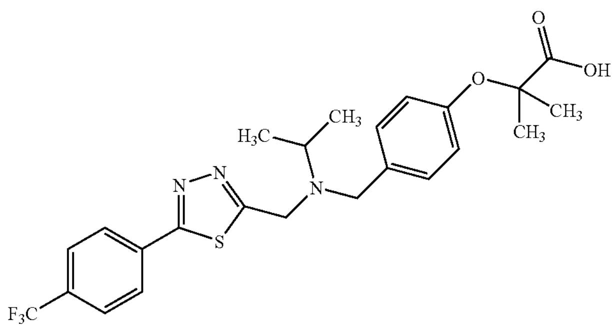 | 492 |
| 107 | 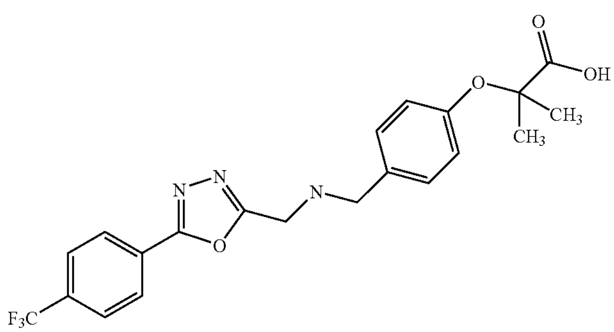 | 452 |
| 108 | 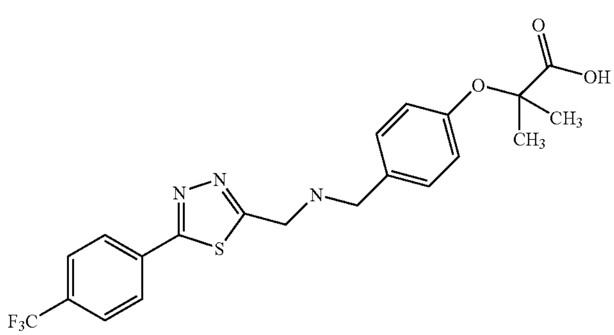 | 450 |

| Example | Structure | LC/MS [M + 1] |
|---|---|---|
| 109 | 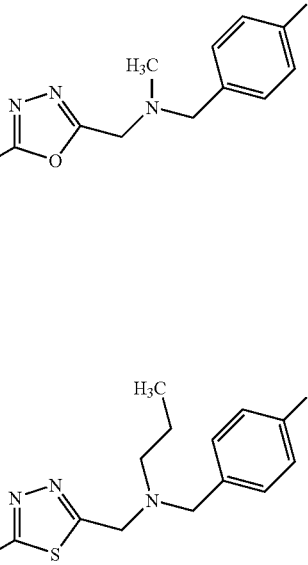 | 448 |
| 110 | 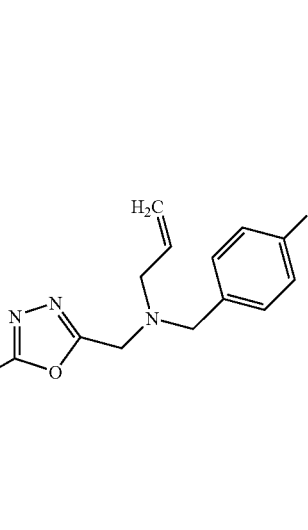 | 494 |
| 111 | 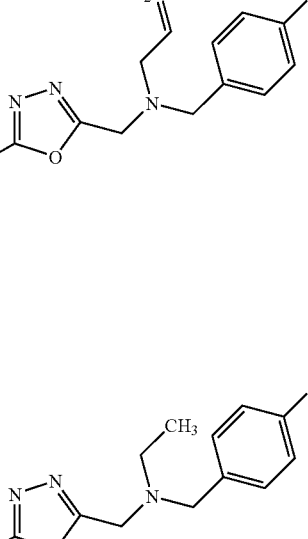 | 476 |
| 112 | 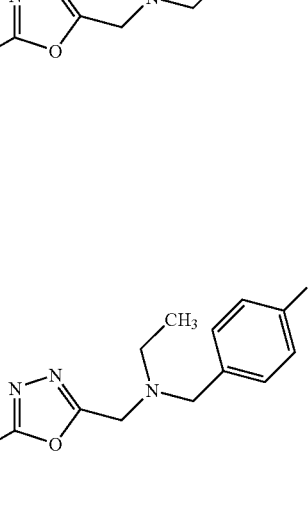 | 464 |

EXAMPLE 113

Lysine Salt of Example 3C

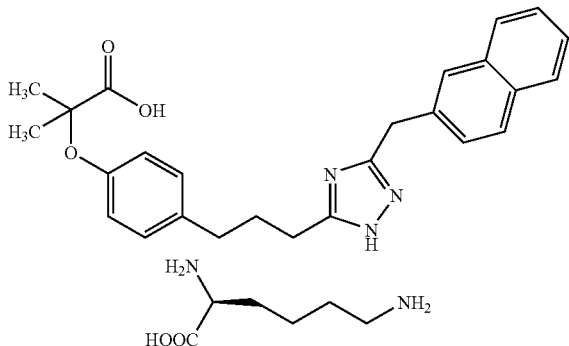

Add 7 mL of MeOH to a vial containing 203 mg of Example 3c and heat to approximately 60° C. Then, add 0.5 mL of L-lysine (in water) at a 1 molar equivalence. Cool to room temperature. Evaporate to dryness under nitrogen. Add 7 mL of isopropyl alcohol which results in a solid suspension. Heat the vial to approximately 80° C. Add water until soluble (2 mL total). Allow the vial to cool to room temperature overnight and the isolate the solid by vacuum filtration. Thermal: Onset 227.8° C.

EXAMPLE 114

Slurry Example 3C (2.00 g, 0.00455 m) in 20.0 mL IPA and heat to 70° C. Filter the hot cloudy/hazy solution and rinse with 1.5 mL EPA, and heat the resulting filtrate to 70° C. In a separate vessel, slurry L-lysine (681 mg, 0.00466 m, 1.0 eq.; Aldrich 97%) in water (2.00 mL) and heat briefly at 50° C. in a water bath to dissolve to a clear solution. Add the solution of L-lysine dropwise to the free acid solution at 70° C. over 35 minutes. Stir the thick slurry for an additional 5 hours at 70° C., then remove from heat and allow to cool down to room temperature for 1 hour. Further cool the resulting slurry in an ice bath for one hour, filter, rinse with cold IPA, and dry under vacuum/40° C. overnight to give the L-lysine salt of Example 3C as a white crystalline solid (2.44 g, 91 weight% yield). Thermal: Onset 227.6° C.

EXAMPLE 115

Slurry Example 114 (0.50 g, 0.00087 m) in MeOH (13 mL) and water (3.0 mL) and heat to 60° C. Concentrate the solution under vacuum and which results in removal of approximately 6.0 g weight solvent. Heat the solution at 60° C. and add IPA (10 mL) dropwise over 10 minutes, maintaining the temperature at 60° C. during the addition. Concentrate the solution again which results in removal of approximately 8.4 g solvent. Then, add additional IPA (10 mL) dropwise over 10 minutes at 60° C. Concentrate the slurry under vacuum which results in removal of approximately 4.9 g solvent, and add a final amount of IPA (5 mL) (hot) over 5 minutes. Heat the slurry briefly at 60° C., allow to cool to room temperature, then cool with an ice bath for 1 hour. Filter, rinse with IPA, and dry overnight under vacuum at 40° C. to obtain a white crystalline product (404 mg; HPLC: 97.4 area %, 81 weight % yield, 86.6 HPLC area % corrected yield). Thermal: Onset 220.19° C.

EXAMPLE 116

Slurry the HCl salt of Example 3C (2.00 g, 0.0043 m) (the free base form could probably be used) in water (15 mL), $CH_2Cl_2$ (15 mL) and MeOH (5 mL). Add 5 N NaOH (1.80 mL, 2.1 eq.) until pH=11. Separate the layers and extract the aqueous layer with additional $CH_2Cl_2$ (15 mL). Combine and discard the organic layers. Add fresh $CH_2Cl_2$ (15 mL) to the aqueous, and add 1 N HCl (15 mL) with vigorous stirring. Separate the layers, extract the aqueous layer with additional $CH_2Cl_2$ (15 mL) and combine the organic layers. Add EtOAc (5 mL) and MeOH (5 mL) to the cloudy organic layer to prevent inadvertent premature crystallization of the HCl salt, then dry the organic layer with $Na_2SO_4$, filter, rinse, and concentrate under vacuum to a weight of 11 g milky solution. Seed the solution with starting material and stir at room temperature as the product crystallizes. Filter and rinse with $CH_2Cl_2$ then dry overnight under vacuum/room temperature to yield white birefringent solid (669 mg, 33 wt % yield, 38% yield HPLC corrected, HPLC: 98.1 area % pure). Thermal: Onset 162.44° C.

Separation of Racemic Mixtures

Isomers of racemic mixtures of examples were separated by HPLC.

| Racemic Example | HPLC conditions | Retention Time (min) Isomer 1 Example | Retention Time (min) Isomer 2 Example |
|---|---|---|---|
| 68 | Chiralpak AD(250 × 4.6 mm), hexane-TFA (0.05%)(A)/IPA(B) Gradient - 20 to 60% B in 15 min | 6.7 Example 69 | 9.0 Example 70 |
| 71 | Chiralpak AD(250 × 4.6 mm), hexane-TFA (0.05%)(A)/IPA(B) Gradient - 20 to 60% B in 15 min | 9.9 Example 72 | 17.1 Example 73 |
| 78 | Chiralpak AD(250 × 20 mm), hexane(A)/IPA(B) 70/30 Isocratic mode | 7.2 Example 79 | 11.4 Example 80 |
| 81 | Chiralpak AD(250 × 4.6 mm), hexane-TFA (0.05%)(A)/IPA(B) 75/25 Isocratic mode | 8.1 Example 82 | 10.4 Example 83 |
| 85 | Chiralpak AD(250 × 4.6 mm), hexane-TFA (0.05%)(A)/IPA(B) 75/25 Isocratic mode | 7.2 Example 86 | 12.3 Example 87 |
| 91 | Chiralpak AD(250 × 4.6 mm), hexane-TFA (0.05%)(A)/ Ethanol(B) 75/25 Gradient mode | 11.5 Example 92 | 18.1 Example 93 |
| 94 | Chiralpak AD(250 × 20 mm), hexane(A)/IPA(B) 70/30 Isocratic mode | 10.5 Example 95 | 15.5 Example 96 |
| 97 | Chiralpak AD(250 × 4.6 mm), hexane-TFA (0.05%)(A)/IPA(B) 95/5 Isocratic mode | 15.7 Example 98 | 18.7 Example 99 |
| 100 | Chiralpak OD(250 × 4.6 mm), hexane-TFA (0.05%)(A)/IPA(B) 75/25 Isocratic mode | 8.7 Example 101 | 11.3 Example 102 |

Biological Assays

Binding and Cotransfection Studies

The in vitro potency of compounds in modulating PPARα receptors are determined by the procedures detailed below.

DNA-dependent binding (ABCD binding) is carried out using SPA technology with PPAR receptors. Tritium-labeled PPARα agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 µM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values for compounds of the invention which are especially useful for modulating a PPAR receptor, are ≦100 nM and ≧50%, respectively.

Evaluation of Triglyceride Reduction and HDL Cholesterol Elevation in HuapoAI Transgenic Mice Compounds of the present invention are studied for effects upon HDL and triglyceride levels in human apoAI mice. For each compound tested, seven to eight week old male mice, transgenic for human apoAI (C57BL/6-tgn(apoa1m)1 rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with $CO_2$ and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured colorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542,1983; Allain C. C. et al., Clin Chem 20:470-475,1974. Commercially available standards for triglycerides and total cholesterol, respectively, commercial quality control plasma, and samples are measured in duplicate using 200 µl of reagent. An additional aliquot of sample, added to a well containing 200 µl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol. is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg-dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLC levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects upon plasma glucose associated with administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, C57B1 Ks/j-m +/+Lepr(db), Jackson Laboratory, Bar Harbor, Me. ] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 μl/well) are measured in duplicate using 200 μl of reagent. An additional aliquot of sample, pipetted to a third well and diluted in 200 μl water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealing a significant reduction in respiratory quotient (RQ) in treated animals during the dark cycle [0.864±0.013 (Control) vs. 0.803±0.007 (Treated); $p < 0.001$] is indicative of an increased utilization of fat during the animals' active (dark) cycle and can be used to selected especially desired compounds of this invention. Additionally, treated animals displaying significantly higher rates of energy expenditure than control animals suggest such compounds of this invention can be especially desired.

Male KK/$A^y$ Mice

Male KK/$A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-Cholesterol Total-Cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster received once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 μl) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 μl of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. Especially desired compounds are markedly more potent than fenofibrate in LDL-lowering efficacy. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On-the last ($14^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 µl of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples. Compounds that lower fibrinogen level greater than vehicle can be especially desired.

Cholesterol and triglyceride lowering effects of compounds of this invention are also studied in Zucker rats.

Method to Elucidate the Anti-Body Weight Gain and Anti-Appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat received once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored. Using this assay, compounds of this invention are identified to determine which can be associated with a significant weight reduction.

Method to Elucidate the Activation of the PPAR Delta Receptor in vivo

This method is particularly useful for measuring the in vivo PPARdelta receptor activation of compounds of this invention that are determined to possess significant in vitro activity for that receptor isoform over the PPAR gamma isoform.

Male PPARa null mice (129s4 SvJae-PPARa<tm1Gonz> mice; Jackson Laboratories) of 8-9 weeks of age are maintained on Purina 5001 chow with water ad libitum for at least one week prior to use. Feed and water are provided ad libitum throughout the course of the experiment. Using the GroupOptimizeV211.xls program, mice are randomized into treatment groups of five animals each based on their body weight.

Compounds of this invention are suspended in an aqueous vehicle of 1% (w/v) carboxymethylcellulose and 0.25% Tween 80 such that each mouse receives once a day approx. 0.2 ml of the solution by gavage at doses ranging from 0.2 to 20 mg/kg body weight. A control group of mice is included in each experiment whereby they are dosed in parallel with vehicle alone. Dosing is performed daily in the early morning for 7 days.

On the last day of dosing, mice are euthanized by $CO_2$ asphyxiation 3 hours after the final dose. Blood samples are collected by heart draw into EDTA-containing microfuge tubes and chilled on ice. Liver samples are collected by necropsy and are flash-frozen in liquid nitrogen and stored at −80 degrees Celsius. For RNA isolation from liver, five to ten mg of frozen liver is placed in 700 µof 1× Nucleic Acid Lysis Solution (Applied Biosystems Inc., Foster City, Calif.) and homogenized using a hand-held tissue macerator (Biospec Products Inc., Bartlesville, Okla.). The homogenate is filtered through an ABI Tissue pre-filter (Applied Biosystems Inc., Foster City, Calif.) and collected in a deep well plate on an ABI 6100 Nucleic Acid prep station (Applied Biosystems Inc., Foster City, Calif.). The filtered homogenate is then loaded onto an RNA isolation plate and the RNA Tissue-Filter-DNA method is run on the ABI 6100. The isolated RNA is eluted in 150 µl of RNase free water. For quality assessment, 9 µl of the isolated RNA solution is loaded onto a 1% TBE agarose gel, and the RNA is visualized by ethidium bromide fluorescence.

Complementary DNA (cDNA) is synthesized using the ABI High Capacity Archive Kit (Applied Biosystems Inc., Foster City, Calif.). Briefly, a 2× reverse transcriptase Master Mix is prepared according to the manufacturer's protocol for the appropriate number of samples (RT Buffer, dNTP, Random Primers, MultiScribe RT (50U/µl), RNase free water). For each reaction, 50 µl of 2× RT Master Mix is added to 50 µl of isolated RNA in a PCR tube that is incubated in a thermocycler (25° C. for 10 minutes followed by 37° C. for 2 hours). The resultant cDNA preparation is diluted 1:100 in dH2O for analysis by real-time PCR. Also, a standard curve of cDNA is diluted 1:20, 1:100, 1:400, 1:2000, 1:10,000 for use in final quantitation.

A real-time PCR Master Mix for mouse Cyp4A1 gene expression is mixed to contain:

1× Taqman Universal PCR Master Mix (Applied Biosystems Inc., Foster City, Calif.)

6 micromolar final concentration Forward primer; Qiagen/Operon Technologies, Alameda, Calif.)

6 micromolar final concentration Reverse primer (Qiagen/Operon Technologies, Alameda, Calif.)

0.15 micromolar final concentration Probe (5' 6-FAM and 3' Tamra-Q; Qiagen/Operon Technologies, Alameda, Calif.)

RNase free water to 10 microliters

A real-time PCR Master Mix for the 18S ribosomal RNA control gene expression is mixed to contain 1× Taqman Universal PCR Master Mix (Applied Biosystems Inc., Foster City, Calif.)

0.34 micromolar Probe/Primer TaqMan® Ribosomal RNA Control Reagents #4308329 Applied Biosystems Inc., Foster City, Calif.)

RNase free water to 10 microliters

For the real-time PCR analysis, 6 ul of the respective Master Mix solution (either Cyp4A1 or 18S) and 4 ul either of diluted cDNA or of Standard Curve samples is added to individual wells of a 384-well plate (n=2 for Standards; n=4 for unknowns). Reactions are performed using the ABI 7900 HT standard universal RT-PCR cycling protocol. Data are analyzed using SDS 2.1 (Applied Biosystems Inc., Foster City, Calif.). Average quantity and standard deviation are calculated automatically for each individual sample, according to the standard curve values. Using Microsoft Excel 2000, mean values for each group of five individual mice is calculated. The mean value of each compound-treated group is divided by the mean value of the vehicle-treated group. The fold induction over the vehicle group is determined by assigning the vehicle group to the value of 1.0, and the fold change of the mean value for each group is expressed as fold-induction versus vehicle (1.0). Data are plotted using Jandel SigmaPlot 8.0.

Monkey Studies

Efficacy Studies

Compounds of the invention may be examined in a dyslipidemic rhesus monkey model. After an oral dose-escalation study for 28 days in obese, non-diabetic rhesus monkeys a determination of HDL-c elevation is made with each dose and compared with pretreatment levels. LDL cholesterol is also determined with each dose. C-reactive protein levels are measured and compared to pretreatment levels.

Compound of Formula 1 may be shown to elevate plasma HDL-cholesterol levels in an African Green Monkey model in a manner similar to that described above in rhesus monkeys.

Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to Measured, for Example:
Body weight
Total plasma cholesterol
HDL
LDL
Triglycerides
Insulin
Glucose
PK parameters at week 4, 7, and 10 (plasma drug concentration at last week of each dose)
ApoAI
ApoAII
ApoB
ApoCIII
Liver enzymes (SGPT, SGOT, □GT)
Complete blood count Additionally, other measures may be made, as appropriate, and consistent with the stated study design.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound wherein the compound is of the Formula Ic:

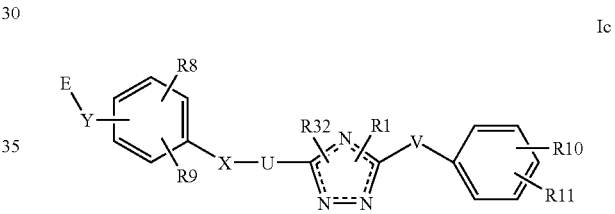

and stereoisomers, or pharmaceutically acceptable salts thereof, wherein:

(a) R1 is hydrogen;

(b) R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) V is selected from the group consisting of $C_0$-$C_8$ alkyl;

(d) X is selected from the group consisting of a single bond;

(e) U is an aliphatic linker wherein one carbon atom of the aliphatic linker is substituted with from one to four substituents each independently selected from R30;

(f) Y is selected from the group consisting of $CH_2$, O, S;

(g) E is C(R3)(R4)A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each R⁷ is independently selected from the group consisting of hydrogen, $C_1$-$C_6$ haloalkyl, aryl $C_0$-$C_4$ alkyl and $C_1$-$C_6$ alkyl;

(iii) R3 is $C_1$-$C_2$ alkyl; and (iv) R4 is methyl optionally substituted with from one to three substituents each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkylenyl, $C_1$-$C_6$ alkyl-COOR12", $C_0$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl, C3-C6 cycloalkylaryl-$C_{0-2}$-alkyl, aryloxy, C(O)R13', COOR14', OC(O)R15', OS(O)₂R16', N(R17')₂, NR18'C(O)R19', NR20'SO₂R21', SR22', S(O)R23', S(O)₂R24', and S(O)₂N(R25')₂; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28; and wherein R10 and R11 optionally combine to form a 5 to 6 membered fused bicyclic ring with the phenyl to which they are bound;

(k) R12', R12", R13', R14', R15', R16', R17', R18', R19', R20', R21', R22, R23', R24', and R25' are each independently selected from the group consisting of hydrogen, $C_1$-$C_6$ alkyl and aryl;

(l) R30 is selected from the group consisting of $C_1$-$C_6$ alkyl, aryl-$C_{0-4}$-alkyl, aryl-$C_{1-4}$-heteroalkyl, and C3-C6 cycloalkylaryl-$C_{0-2}$-alkyl, and wherein $C_1$-$C_6$ alkyl, aryl-$C_{0-4}$-alkyl, aryl- $C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(m) R32 is selected from the group consisting of hydrogen, halo, $C_1$-$C_6$ alkyl, $C_1$-$C_6$ haloalkyl, and $C_1$-$C_6$ alkyloxo; and (n) ---- is optionally a bond to form a double bond at the indicated position.

2. A compound as claimed by claim 1 wherein Y is O.

3. A compound as claimed by claim 1 wherein Y is $CH_2$.

4. A compound as claimed by claim 1 wherein Y is S.

5. A compound as claimed by claim 1 wherein two of "----" in the five membered ring are each a bond to form double bonds at the designated locations.

6. A compound as claimed by claim 5 wherein A is COOH.

7. A compound as claimed by claim 5 wherein V is selected from the group consisting of $C_0$-$C_1$ alkyl.

8. A compound as claimed by claim 5 wherein U is $C_1$-$C_3$ alkyl.

9. A compound as claimed by claim 1, represented by the following Structural Formula VI:

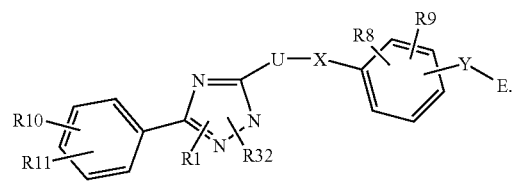

10. A compound as claimed by claim 1, represented by the following Structural Formula IX:

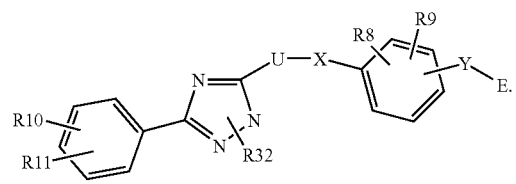

11. A compound as claimed by claim 1 wherein the compound is a compound of the formula:

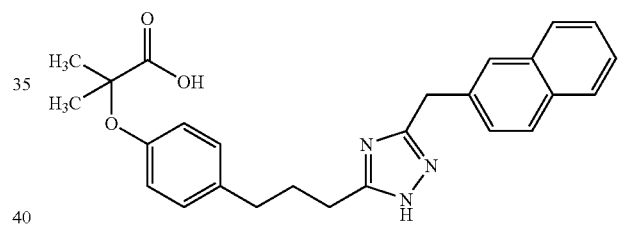

or a pharmaceutically acceptable salt thereof.

12. A compound as claimed by claim 1 wherein X is a bond.

13. A pharmaceutical composition, comprising as an active ingredient, at least one compound as claimed by claim 1 together with a pharmaceutically acceptable carrier or diluent.

14. A compound as claimed by claim 9 wherein the compound is selected from the group consisting of:

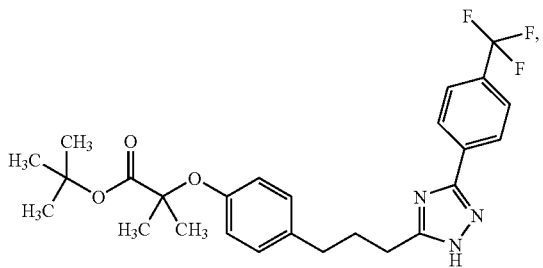

-continued

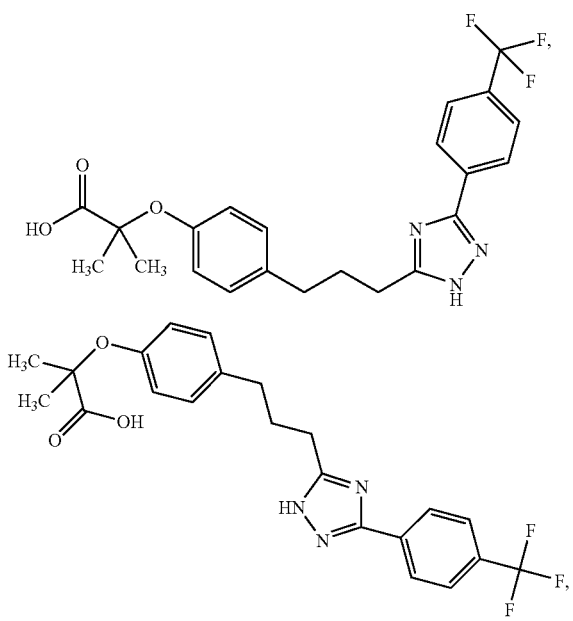

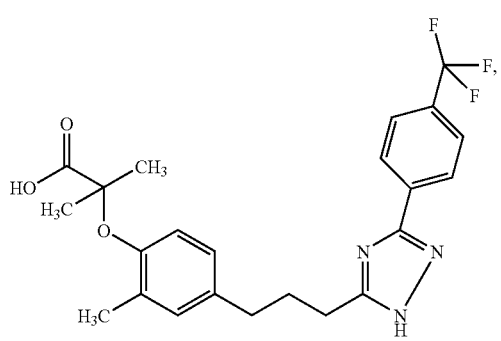

and

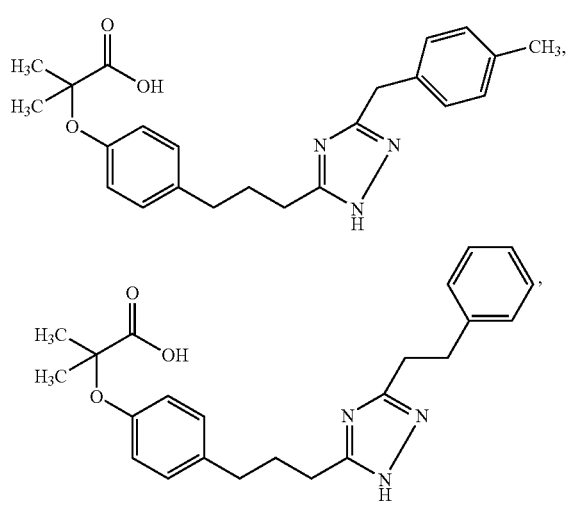

or pharmaceutically acceptable salt thereof.

15. A compound as claimed by claim 10 wherein the compound is selected from the group consisting of:

-continued

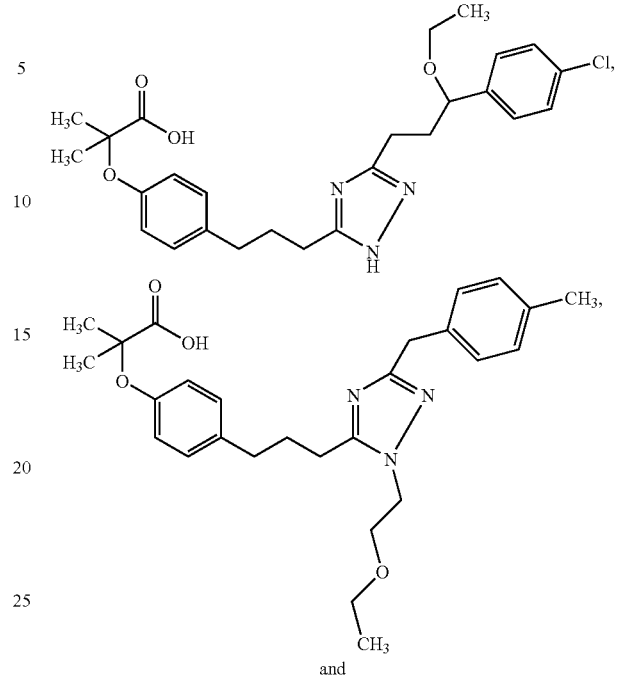

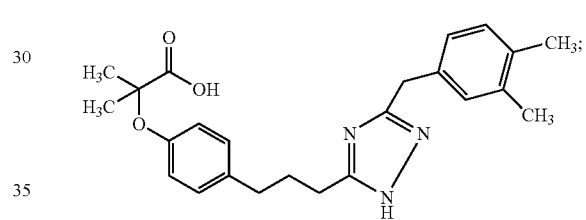

and

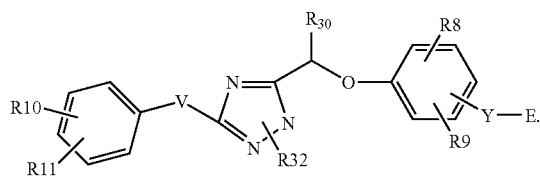

or a pharmaceutically salt thereof.

16. A compound as claimed by claim 1, of the structural formula:

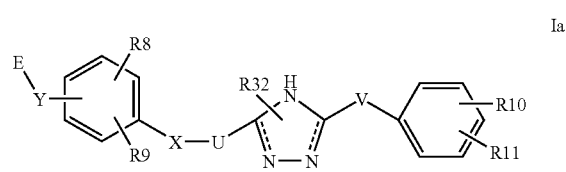

17. A compound as claimed by claim 1, of the Formula Ia:

Ia

E—Y—[R8/R9 phenyl]—X—U—[R32, H triazole]—V—[R10/R11 phenyl]

and stereoisomers, or pharmaceutically acceptable salts thereof,
wherein:
(a) R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(b) V is selected from the group consisting of $C_0$-$C_8$ alkyl;

(c) X is selected from the group consisting of a single bond;

(d) U is an aliphatic linker wherein one carbon atom of the aliphatic linker is optionally substituted with from one to two substituents each independently selected from R30;

(e) Y is selected from the group consisting of CH$_2$, O, and S;

(f) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
  (ii) each $R^7$ is independently selected from the group consisting of hydrogen, $C_1$-$C_6$haloalkyl, aryl $C_0$-$C_4$ alkyl and $C_1$-$C_6$ alkyl;
  (iii) R3 is $C_1$-$C_2$ alkyl; and
  (iv) R4 is methyl optionally substituted with from one to three substituents each independently selected from R26;

(g) R8 is selected from the group consisting of hydrogen, $C_1$-$C_4$ alkyl, $C_1$-$C_4$ alkylenyl, and halo;

(h) R9 is selected from the group consisting of hydrogen, $C_1$-$C_4$ alkyl, $C_1$-$C_4$ alkylenyl, halo, aryl-$C_0$-$C_4$ alkyl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(i) R10, R11 are each independently selected from the group consisting of hydrogen, hydroxy, cyano, nitro, halo, oxo, $C_1$-$C_6$ alkyl, $C_1$-$C_6$ alkylenyl, $C_1$-$C_6$ alkyl-COOR12", $C_0$-$C_6$ alkoxy, $C_1$-$C_6$haloalkyl, $C_1$-$C_6$ haloalkyloxy, $C_3$-$C_7$ cycloalkyl, aryl-$C_{0-4}$-alkyl, aryl-$C_{1-4}$-heteroalkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28; and wherein R10 and R11 optionally combine to form a 5 to 6 membered fused bicyclic ring with the phenyl to which they are bound;

(j) R12', R12', R13', R14', R15', R16', R17', R18', R19', R20', R21', R22', R23', R24', and R25'are each independently selected from the group consisting of hydrogen, $C_1$-$C_6$ alkyl and aryl;

(k) R30 is selected from the group consisting of $C_1$-$C_6$ alkyl, aryl-$C_{0-4}$-alkyl, aryl-$C_{1-4}$-heteroalkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(l) R32 is selected from the group consisting of hydrogen, halo, $C_1$-$C_6$ alkyl, $C_1$-$C_6$ haloalkyl, and $C_1$-$C_6$ alkyloxo; and (m) ---- is optionally a bond to form a double bond at the indicated position.

* * * * *